US005831053A

United States Patent [19]
Gleeson et al.

[11] Patent Number: 5,831,053
[45] Date of Patent: Nov. 3, 1998

[54] GENES WHICH INFLUENCE PICHIA PROTEOLYTIC ACTIVITY, AND USES THEREFOR

[75] Inventors: Martin A. Gleeson; Bradley D. Howard, both of San Diego, Calif.

[73] Assignee: Sibia Neurosciences, Inc., La Jolla, Calif.

[21] Appl. No.: 441,751

[22] Filed: May 16, 1995

Related U.S. Application Data

[62] Division of Ser. No. 245,756, May 16, 1994, Pat. No. 5,541,112, which is a division of Ser. No. 88,633, Jul. 6, 1993, Pat. No. 5,324,660, which is a continuation of Ser. No. 678,916, Apr. 1, 1991, abandoned.

[51] Int. Cl.$^6$ ............................. C07H 21/04; C12N 9/88
[52] U.S. Cl. .......................................... 536/23.2; 435/232
[58] Field of Search .......................... 536/23.2; 435/232, 435/320.1

[56] References Cited

U.S. PATENT DOCUMENTS

| | | | |
|---|---|---|---|
| 4,546,082 | 10/1985 | Kurjan et al. | 435/172.3 |
| 4,812,405 | 3/1989 | Lair et al. | 435/255 |
| 4,837,148 | 6/1989 | Cregg | 435/172.3 |
| 4,855,231 | 8/1989 | Sroman et al. | 435/68 |
| 4,870,008 | 9/1989 | Brake | 435/70 |
| 4,879,231 | 11/1989 | Stroman et al. | 435/172.3 |
| 4,882,279 | 11/1989 | Cregg | 435/172.3 |
| 4,885,242 | 12/1989 | Cregg | 435/68 |
| 4,895,800 | 1/1990 | Tschopp et al. | 435/69.3 |
| 4,929,555 | 5/1990 | Cregg et al. | 435/172.3 |
| 5,002,876 | 3/1991 | Sreekrishna et al. | 435/69.5 |
| 5,162,208 | 11/1992 | Lemoine et al. | 435/69.1 |
| 5,179,003 | 1/1993 | Wolf et al. | 435/69.1 |
| 5,231,010 | 7/1993 | Ebbers et al. | 435/69.2 |
| 5,231,178 | 7/1993 | Holtz et al. | 530/399 |
| 5,258,302 | 11/1993 | Vedvick et al. | 435/254.23 |
| 5,324,639 | 6/1994 | Brierley et al. | 435/69.4 |

FOREIGN PATENT DOCUMENTS

| | | |
|---|---|---|
| 0591524 | 4/1944 | European Pat. Off. |
| 0324274 | 7/1984 | European Pat. Off. |
| 0123228 | 10/1984 | European Pat. Off. |
| 0128733 | 12/1984 | European Pat. Off. |
| 0142268 | 5/1985 | European Pat. Off. |
| 0173378 | 3/1986 | European Pat. Off. |
| 0213593 | 3/1987 | European Pat. Off. |
| 0327797 | 8/1989 | European Pat. Off. |
| 0336056 | 10/1989 | European Pat. Off. |
| 0341215 | 11/1989 | European Pat. Off. |
| 0360411 | 3/1990 | European Pat. Off. |
| 0390676 | 10/1990 | European Pat. Off. |
| 2188933 | 10/1987 | United Kingdom . |
| 8403103 | 8/1984 | WIPO . |
| 8904320 | 5/1989 | WIPO . |
| 9000191 | 1/1990 | WIPO . |
| 9002810 | 3/1990 | WIPO . |
| 9003431 | 4/1990 | WIPO . |
| 9009434 | 8/1990 | WIPO . |
| 9009449 | 8/1990 | WIPO . |
| 9105057 | 4/1991 | WIPO . |
| 9204363 | 3/1992 | WIPO . |
| 9204441 | 3/1992 | WIPO . |
| 9213951 | 8/1992 | WIPO . |
| 9309233 | 5/1993 | WIPO . |

OTHER PUBLICATIONS

Gleeson et al., Isolation of *Candida tropicalis* auxotrophic mutants, *Appl. Environ. Microbiol.* 56:2562–2564 (1990).

Ammerer, et al., "PEP4 gene of Saccharomyces cerevisia encodes proteinase A, a vacuolar enzyme required for processing of vacuolar precursors," *Molec. Cell. Biol.* 6:2490–2499 (1986).

Amore, et al., *Gene*, 109:89–97 (1991).

Bayne, et al., "Expression, Purification and Characterization of Recombinant Human Insulin–Like Growth Factor I in Yeast," *Gene*, 66:235–244 (1988).

Boeke, et al., "A positive selection for mutants lacking orotidine–5'–phosphate decarboxylase activity in yeast: 5–fluoro–orotic acid resistance," *Mol. Gen. Genet.*, 197:345–346 (1984).

Brake, et al., "A functional prepro–α–factor gene in saccharomyces yeasts can contain three, four, or five repeats of the mature pheromone sequence," *Mol. Cell. Biol.*, 3(8):1400–1450 (1983).

Buckholz and Gleeson, "Yeast Systems for the Commercial Production of Heterologous Proteins," *Bio/Technology*, 9:1067–1072 (1991).

Chemical Abtrs., 106:48594f, citing Nelson et al., *J. Inst. Brew.*, 96:599–603 (1987).

Cregg, et al., "Pichia pastoris as a Host System for Transformations," *Mol. Cell. Biol.*, 5:3376–3385 (1985).

Cregg, et al., "High–level expression and efficient assembly of hepatitis B surface antigen in the methylotrophic yeast, pichia pastrosis," *Bio/Technology*, 5:479–485 (1987).

Cregg, "Genetics of Methylotrophic Yeasts," *Microbial Growth on $C_1$ Compounds: Proceedings of the 5th International Symposium*, pp. 158–167 (1987).

Cregg and Madden, "Development for Yeast Transformation Systems and Construction of Methanol–Utilization–Defective Mutants of *Pichia Pastori* by Gene Disruption," *Biological Research on Industrial Yeasts*, vol. II:pp. 1–18 (1987).

(List continued on next page.)

*Primary Examiner*—Robert A. Wax
*Assistant Examiner*—Elizabeth Slobodyansky
*Attorney, Agent, or Firm*—Stephanie L. Seidman; Brown, Martin, Haller & McClain

[57] ABSTRACT

The isolation and characterization of genes involved in proteolytic processing in species of the genus Pichia is described. The availability of such genes has enabled the generation of strains of Pichia which are deficient in proteolytic activity, which strains are useful as hosts for the expression of proteolytically sensitive recombinant products. The isolation and characterization of additional genes from species of the genus Pichia is also described, as well as uses therefore.

3 Claims, 15 Drawing Sheets

OTHER PUBLICATIONS

Cregg and Madden, "Development of the Methylotrophic Yeast, *Pichia Pastoris*, as a Host System for the Production of Foreign Proteins," *Developments in Industrial Microbiology*, 29:33–41 (1988).

Cregg, et al., "Expression of Foreign Genes in *Pichia Pastoris*," *Genetics and Molecular Biology of Industrial Microorganisms*, Hershberger, et al. (Eds.), *Amer. Soc. for Microbiol.*, Washington, D.C., pp. 343–351 (1989).

Digan, et al., "Secretion of heterologous proteins from the methylotrophic yeast, *Pichia pastoris*," *J. Industrial Microbiol.*, 29(Supp. 3):59–65 (1988).

Digan, et al., "Continuous Production of a Novel Lysozyme Via Secretion from the Yeast, *Pichia Pastoris*," *Bio/Technology*, 7(2):160–164 (1989).

Elliott, et al., "Yeast–Derived Recombinant Human Insulin–Like Growth Factor I: Production, Purification, and Structural Characterization," *J. of Protein Chemistry*, 9(1):95–104 (1990).

Ellis, et al., "Isolation of Alcohol Oxidase and Two Other Methanol Regulatable Genes from the Yeast *Pichia Pastoris*," *Molecular and Cellular Biology*, 5(5):1111–1121 (1985).

Ernst, "Improved Secretion of Heterologous Proteins by *Saccharomyces Cerevisae*: Effects of Promoter Substitution of Alpha–Factor Fusions," *DNA*, 5(6):483–491 (1986).

Gellisen, et al., "Heterologous Protein Production in Yeast," *Antonie van Leeuwenhoek*, 62:79–93 (1992).

Gleeson and Sudbery, "The Methylotrophic Yeasts," *Yeast*, 4:1–15 (1989).

Grinna and Tschopp, "Size distribution and general structural features of N–linked oligosaccharides from the methylotrophic yeast, *pichia pastoris*," *Yeast*, 5:107–115 (1989).

Ito, et al., "Transformation of intact yeasts cells treated with alkali cations or thio compounds," *Agric. Biol. Chem.*, 48(2):341–347 (1984).

Jones, et al., "PEP4 gene function is required for expression of several vacuolar hydroases in *Saccharomyces cerevisiae*," *Genetics* 102:665–677 (1982).

Komagata, "Systematics of Methylotrophic Yeasts," *Biology of Methylotrophs*, pp. 25–37 (1991).

Koutz, et al., "Structural comparison of the *pichia pastoris* alcohol oxidase genes," *Yeast*, 5:167–177 (1989).

Kurtzman, "Synony my of the Yeast Genera Hansenula and Pichia Demonstrated through Comparisons of Deoxyribonucleic Acid Relatedness," *Antonie van Leeuwenhoek*, 50:209–217 (1984).

Kushnirov et al., *Yeast*, 6:461–472 (1990).

Moehle et al., "Protease B of the Lysosomelike Vacuole of the Yeast *Saccharomyces cerevisiae* Is Homologous to the Subtilisin family of Serine Proteases," *Mol. Cell. Biol.*, 7:4390–4399 (1987).

Rose, et al., "Structure and function of the yeast URA3 gene: Expression in *Escherichia coli*," *Gene*, 29:113–124 (1984).

Rothman, et al., "Overproduction–induced mislocalization of a yeast vacuolar protein allows isolation of its structural gene," *Proc. Natl. Acad. Sci.* 83:3284–3252 (1986).

Rothstein, "One–step gene disruption in yeast," *Methods in Enzymology*, 101:202–211 (1983).

Shuster, "Regulated Transcriptional Systems for the Production of Proteins in Yeast: Regulation by Carbon Source," *Yeast Genetic Engineering*, pp. 83, 97–99, 108 (1989).

Strasser, et al., "Applications of Genetically Manipulated Yeasts," *Appl. Mol. Genet. Fungi*, 10:161–169 (1991).

Suzuki, et al., "Yeast mutants with enhanced ability to secrete human lysozyme: Isolation and identification of a protease–deficient mutant," *Mol. Gen. Genet.* 219:58–64 (1989).

Trimble, et al., "Structure of Oligosaccharides on Saccharomyces SUC2 Invertase Secreted by the Methylotrophic Yeast *Pichia Pastoris*," *J. of Biol. Chem.*, 206(34):22807–22815 (1991).

Tschopp, et al., "High–level secretion of glycosylated invertase in the methylotrophic yeast, *pichia pastoris*," *Bio/Technology*, 5:1305–1308 (1987).

Woolard, et al., "The PEP4 gene encodes an aspartyl protease implicated in the posttranslational regulation of *Saccharomyces cerevisae* vacuolar hydrolases," *Molec. Cell. Biol.* 6:2500–2510 (1986).

GENES WHICH INFLUENCE PICHIA PROTEOLYTIC ACTIVITY, AND USES THEREFOR

This is a divisional of application Ser. No. 08/245,756, filed May 16, 1994 now U.S. Pat. No. 5,541,112, which is a divisional of Ser. No. 08/088,633, filed Jul. 6, 1993, U.S. Pat. No. 5,324,660 which in turn is a continuation of application Ser. No. 07/678,916, filed Apr. 1, 1991, now abandoned.

This invention relates to recombinant DNA technology. In a particular aspect, the present invention relates to novel yeast strains produced employing recombinant techniques, and novel DNA sequences encoding proteins involved in proteolytic processing, as well as novel auxotrophic marker proteins. In another aspect, the present invention relates to methods of producing recombinant products, especially recombinant products which are susceptible to proteolytic degradation.

BACKGROUND OF THE INVENTION

Strains of the genus Pichia have been developed as an efficient expression system for the production of recombinant products. Unfortunately, however, some protein products which are desirably produced by recombinant means (e.g., IGF-1, EGF, GRF, and the like) are susceptible to degradation by proteases produced by the host organism. In such cases, even if high levels of the desired product are expressed, reduced product recoveries are sometimes realized due to degradation of the product in the presence of certain of the host strain's proteolytic enzymes. Product recovery is further complicated by the presence of various proteolysis degradation products.

It would be desirable, in view of the excellent performance of the Pichia-based expression system for the production of many recombinant products, to reduce or eliminate certain proteolytic activities of Pichia. This would reduce the likelihood of degradation of protease-sensitive products when produced in recombinant Pichia hosts. Reduced likelihood of degradation would result in an enhanced ability to express and recover such products in substantially intact form.

Various techniques can be applied in an effort to reduce or eliminate the problem of proteolytic degradation of recombinantly produced products. For example, one could modify the conditions under which recombinant strains are grown so as to inhibit protease activity. This could be accomplished, for example, by adjusting the pH of the medium sufficiently to inhibit the action of various proteases. This approach, however, may affect the ability of the host organism to express certain recombinant products (as well as the stability of the resulting product, once expressed). Moreover, this approach is limited only to its affect on extracellular proteolysis.

Alternatively, one could attempt to modify or eliminate some or all of the host organism's processing enzymes which are responsible for the proteolytic activity which degrades recombinantly produced, proteolytically sensitive products. Proteolytic processes in eukaryotic organisms are, however, quite complicated and involved. Thus, it is not possible to predict if elimination and/or modification of one or more of the enzyme(s) that are involved in proteolytic processing pathways will have an impact on the viability of the host cells, and/or the stability of the recombinantly produced products.

Some of the proteolytic activities of the yeast *S. cerevisiae* have been characterized. Proteinase A, for example, is encoded by the *S. cerevisiae* PEP4 gene. Proteinase A is a vacuolar, aspartyl protease capable of self-activation, as well as subsequent activation of additional vacuolar proteases, such as carboxypeptidase Y, and proteinase B. Although carboxypeptidase Y appears to be completely inactive prior to proteinase A-mediated proteolytic processing of the enzyme, proteinase B (encoded by the PRB-1 gene of *S. cerevisiae*) reportedly is approximately 50% bioactive in its precursor form (i.e., the form that exists prior to proteinase A-mediated processing of the enzyme).

*S. cerevisiae* and filamentous fungi deficient in proteolytic activity have previously been described. Such strains have been used for the recombinant expression of heterologous peptides. These organisms, however, differ substantially from the methylotrophic yeast, Pichia. For example, unlike Saccharomyces or Aspergillus, Pichia cells used for the recombinant expression of heterologous peptides are typically grown at high cell density. High cell density growth is made possible, at least in part, by selection of strains which minimize the occurrence of foaming during the fermentation process (which is accomplished by selecting for cells which produce large amounts of endo- and exo-proteases, which reduce foaming by reducing the size of proteins secreted into the media). Furthermore, while growth at high cell density enables the production of heterologous peptides in remarkably high yields, growth at high cell density also provides for a relatively high level of vacuolar proteases in the fermentation media (since ~1% of cells typically undergo lysis during yeast fermentation, the high cell density process is accompanied by the release of substantial quantities of cellular material into the media, including vacuolar proteases). Therefore, during the production of heterologous peptides in a high cell density process, some of the secreted, heterologous peptides produced by Pichia could be subjected to substantial proteolysis.

Furthermore, since there are numerous metabolic and physiological differences between Saccharomyces, Aspergillus, and Pichia, it cannot be expected that the proteolytic processing systems of these various organisms are necessarily similar. Indeed, very little is presently known regarding the types of proteolytic activities present in Pichia.

SUMMARY OF THE INVENTION

In accordance with the present invention, we have isolated and characterized genes involved in proteolytic processes of species of the genus Pichia. The availability of such genes has enabled the generation of strains of Pichia which are deficient in proteolytic activity, which strains are useful as hosts for the expression of proteolytically sensitive products.

We have found that strains of Pichia which have been modified so as to be defective in proteolytic activity, relative to wild-type Pichia cells, are excellent hosts for the expression of recombinant constructs encoding proteolytically sensitive products. The advantage of high levels of recombinant product expression possible with the powerful Pichia expression system, coupled with the low level of proteolytic activity in the invention host cells provides a highly efficient expression system for the production of proteolytically sensitive products.

In accordance with another embodiment of the present invention, we have isolated and characterized the gene which encodes the Pichia orotidine-5'-phosphate decarboxylase protein (i.e., the URA3 gene). The availability of this gene, in combination with strains of Pichia which are Ura⁻, provides a particularly useful selection system for use in producing recombinant strains of Pichia which are deficient in proteolytic activity. Such Ura⁻ strains are also useful as hosts for transformation with recombinant DNA constructs, which are then used for the recombinant expression of a variety of heterologous products.

DETAILED DESCRIPTION OF THE INVENTION

In accordance with the present invention, there is provided an isolated DNA fragment obtained from a strain of the genus Pichia which comprises a gene encoding a protein which, directly or indirectly, influences the proteolytic activity of said strain.

In accordance with another embodiment of the present invention, there is provided a method of producing modified strain(s) of the genus Pichia which are deficient in proteolytic activity, relative to host strain(s) of the same species which are not so modified, said method comprising:

contacting said host strain(s) with a modified form of the above-described gene, wherein said modification renders the gene incapable of producing functional product, or alters the ability of the gene product to influence proteolytic activity, wherein said contacting is carried out under conditions suitable for the site-directed integration of said modified form of the above-described gene into the genome of said host strain(s), wherein said site-directed integration occurs at the specific locus of said gene which encodes said protein which influences proteolytic activity.

In accordance with yet another embodiment of the present invention, there are provided strains of the genus Pichia which are deficient in proteolytic activity. Such strains can be produced in a variety of ways, with the above-described method being the presently preferred way of producing such strains.

In accordance with still another embodiment of the present invention, there is provided a method for the expression of proteolytically sensitive recombinant product(s), said method comprising expressing said proteolytically sensitive product(s) in the above-described Pichia cells which are deficient in proteolytic activity.

In accordance with a further embodiment of the present invention, there is provided an isolated DNA fragment obtained from a species of the genus Pichia which comprises the orotidine-5'-phosphate decarboxylase gene.

In accordance with a still further embodiment of the present invention, there is provided a yeast cell of the genus Pichia as a host capable of being transformed with recombinant DNA material, wherein said host is defective in the orotidine-5'-phosphate decarboxylase gene.

As employed herein, the term "proteolytic activity" refers to any one or more of the enzyme activities displayed by enzymes involved in the proteolytic pathway. Proteolytic activities include proteinase A activity, proteinase B activity, carboxypeptidase Y activity, carboxypeptidase S activity, aminopeptidase C activity, dipeptidyl aminopeptidase activity, proteinase D activity, proteinase E activity, and the like.

Figure 1:
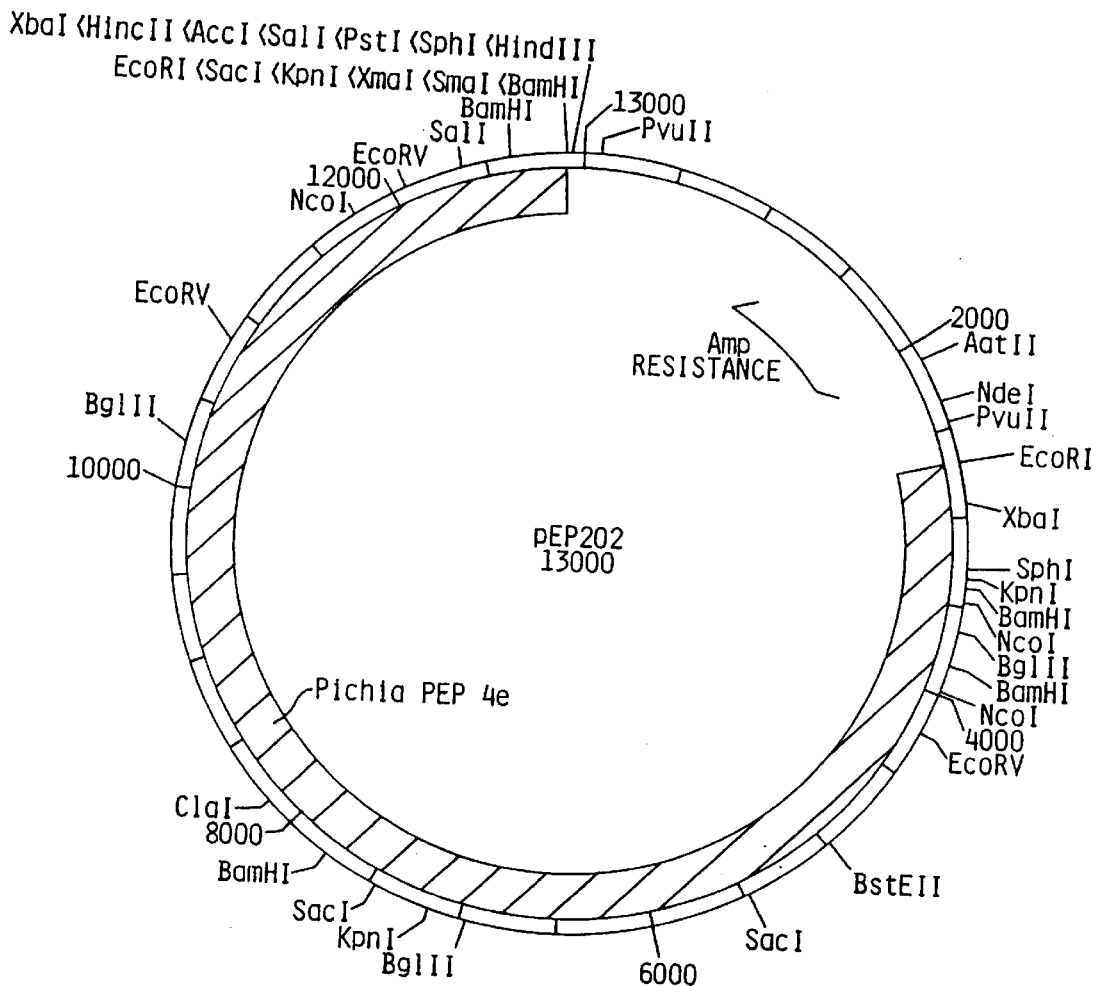
FIG. 1 is a restriction map of plasmid pEP202.

In accordance with one embodiment of the present invention, the Pichia gene that encodes a protein which, directly or indirectly, influences at least the carboxypeptidase Y activity of strains of the genus Pichia has been identified and isolated from a species of the genus Pichia. This gene is referred to herein, for convenience, as the Pichia PEP4 gene, based on the existence of some similarity between this gene and the *S. cerevisiae* PEP4 gene. It should be recognized, however, that the nucleotide sequences of the Pichia gene and the Saccharomyces gene differ substantially, as would be expected since the two species are substantially different. The novel Pichia PEP4 gene has the amino acid sequence encode by Sequence ID No. 1. A fragment containing sequences encoding this novel gene can be readily obtained for easy handling from a variety of sources. One such source is the approximately 10.6 kbp EcoRI fragment of plasmid pEP202 (see FIG. 1), or alternatively, the approximately 2.7 kbp EcoRI-SacI fragment of plasmid pEP301 (see FIG. 3). The proteinase A gene of the present invention can be further characterized by reference to the amino acid sequence set forth in Sequence ID No. 2. Any nucleic acid sequence which encodes substantially the same amino acid sequence as set forth in Sequence ID No. 2 can be employed in the practice of the present invention. An exemplary nucleic acid sequence which encodes the above-described amino acid sequence is set forth in Sequence ID No. 1.

The Pichia gene that encodes a protein which, directly or indirectly, influences the proteolytic activity of strains of the genus Pichia can be modified in a variety of ways, so as to render the gene incapable of producing functional product, or so as to alter the ability of the gene product to influence the proteolytic activity of said Pichia strain(s). Those of skill in the art recognize that there are many methods for the modification of the above-described gene. For example, the coding sequence can be mutated to modify the amino acid sequence of the protein encoded by the gene. Alternatively, various portions of the coding sequence can be deleted from the gene. The deletion need only be sufficient to render the expressed product (if it is still capable of being expressed) non-functional. Thus, a deletion of even one nucleotide, by throwing the remaining coding sequence out of reading frame, can render a product, if still capable of expression, non-functional. Of course, larger deletions can result in a complete lack of expression of product, or can cause a substantially modified product to be expressed, and such a product is likely to have very different proteolytic properties, if any, relative to product produced by intact gene. As yet another alternative, additional sequences can be inserted into the coding sequence to disrupt the reading frame of the gene of interest, which would cause a dramatically altered product to be expressed, or a complete lack of expression of the product.

A particularly convenient method for the modification of the Pichia gene that encodes a protein which, directly or indirectly, influences the proteolytic activity of strains of the genus Pichia is to insert an auxotrophic marker gene into said Pichia gene, thereby disrupting the Pichia gene. Such auxotrophic marker genes can be selected from the Pichia or Saccharomyces HIS4 gene, the Pichia or Saccharomyces ARG4 genes, the Pichia or Saccharomyces URA3 genes, and the like.

Strains of Pichia deficient in proteolytic activity can be prepared in a variety of ways. The presently preferred method involves modifying, in a suitable host, genes of the present invention (which genes, in their unmodified form, encode a product which, directly or indirectly, affect the proteolytic activity of strains of the genus Pichia). Alternatively, host strains can be subjected to random (i.e., non-selective) mutagenesis, then screened to select for mutants which are deficient in proteolytic activity. This is not presently preferred because random mutagenesis is a non-selective process, which requires extensive screening and selection in order to identify a well-characterized mutant. In addition, there is the possibility of producing strains which contain multiple defects, as opposed to strains containing a single, well defined defect.

When proteolytically deficient strains are produced by modifying the gene of the invention in a host, such modifying is carried out, for example, by introducing a modified gene under transformation conditions suitable for the site-directed integration of the modified gene into the genome of the host at the specific locus of such gene which encodes a protein which influences proteolytic activity (i.e., the target gene). Integration will replace or alter the host's endogenous gene. A convenient means to introduce the modified gene into the target locus of a yeast host is to include the modified gene in a linear DNA fragment having ends homologous to two separate portions of the intact gene within the host. This will direct, upon transformation, that homologous recombination occur at the specific locus of the gene whose expression product influences proteolytic activity.

When Pichia strains deficient in proteolytic activity are prepared by the preferred method described above (i.e., by introducing a modified gene of the invention into a suitable host by site-directed integration at the specific locus of the gene whose expression product influences proteolytic activity, thereby replacing all or a portion of the endogenous gene with all or a portion of the modified gene), the endogenous gene is said to be disrupted. As used herein, the term gene "disruption" refers to any manipulation of the target locus that ultimately results in the presence of a gene that does not yield a functional product, or that yields a product with altered function. Disruption can, therefore, result from the presence of added sequence (e.g., by the introduction of auxotrophic marker, or by the introduction of any sequence which causes a shift in the reading frame), the loss of nucleotides from the target gene (e.g., by deletion), or other mutations of the target gene. For the preferred method of preparing Pichia strains deficient in proteolytic activity, gene disruption is achieved by gene addition, gene replacement, or a combination of addition and replacement referred to herein as "pop-in-pop-out". In gene replacement, the endogenous target gene is physically removed from the target locus, and replaced with the modified gene. This is accomplished by transforming the host with a linear fragment having ends which are homologous to the 5' and 3' ends of the target gene, respectively. Gene addition involves adding the transforming DNA to the endogenous target gene. Depending on the manner in which the modified gene of the transforming DNA was altered, gene addition can result in the presence of either two non-functional copies of the target gene, or one functional and one non-functional copy of the target gene. Each of the two copies consists of a portion of the endogenous gene, and a portion of the transforming DNA. If a functional copy of the target gene remains after gene addition, it can then be removed by homologous recombination between the two copies of the target gene. The combination process of gene addition followed by homologous recombination constitutes the pop-in-pop-out process.

Methods of transforming yeast of the genus Pichia, as well as methods applicable for culturing such yeast cells, are known generally in the art.

According to the invention, constructs containing the above-described modified gene are transformed into Pichia cells either by the spheroplast technique, described by Cregg et al., in Mol. Cell, Biol. 5:3376 (1985) and U.S. Pat. No. 4,879,231, or by the whole-cell lithium chloride yeast transformation system [Ito et al., Agric. Biol. Chem. 48:341 (1984)], with modification necessary for adaptation to Pichia [See European Patent Application No. 312,934; also available as U.S. Pat. No. 4,929,535]. The whole-cell lithium chloride method is frequently more convenient in that it does not require the generation and maintenance of spheroplasts. However, for the purpose of the present invention, the spheroplast method is preferred because the spheroplast method is generally a more efficient means of transformation.

Those of skill in the art recognize that host Pichia strains for transformation with the above-described modified gene can be wild-type Pichia cells, which upon transformation with a defective gene from the proteolytic pathway, could be screened for reduced proteolytic activity. The host strains employed can have one or more defects therein, to assist in the identification and selection of desired transformants.

Preferred hosts employed for transformation with a modified form of the gene which encodes a protein which, directly or indirectly, influences the proteolytic activity of strains of Pichia, is a strain which is defective in at least one auxotrophic marker gene. The use of such host organisms is preferred because simultaneous transformation of such a host with the modified form of the invention gene and an auxotrophic marker gene enables rapid selection of strains which have incorporated the transforming DNA, and thus, should have a disrupted form of the gene which encodes a protein which directly or indirectly influences the proteolytic activity of the host.

Exemplary auxotrophic marker genes useful in the practice of the present invention (i.e., marker genes that are defective in the preferred host strains employed herein) include the histidinol dehydrogenase gene, the argininosuccinate lyase gene, or the orotidine-5'-phosphate decarboxylase gene, and the like. When employing such host strains in the transformation of Pichia, the above-described modified gene, contained in a linear DNA fragment, is preferably associated with an intact form of the auxotrophic marker gene for which the host strain is defective, e.g., the auxotrophic marker gene either is contained within the modified gene, or is located 5' or 3' of the modified gene on the transforming linear DNA fragment. Exemplary host strains contemplated for use in the practice of the present invention include the his4-defective Pichia strain, GS115 (ATCC 20864), the arg4-defective Pichia strain, GS190, the his4/ura3-defective Pichia strain, GS4-2, the his4/arg4-defective Pichia strain PPF1 (NRRL Y-18017; see U.S. Pat. No. 4,812,405), and the like. An exemplary fragment of DNA which contains the above-described modified gene having inserted therein a functional gene encoding histidinol dehydrogenase can be obtained from the approximately 5.3 kbp SacI-EcoRI fragment of plasmid pDR401. Another exemplary fragment of DNA which contains a modified form of the above-described gene (located 5' of a functional gene encoding orotidine-5'-phosphate decarboxylase) can be obtained from the approximately 5.0 kbp BglII fragment of plasmid pDR421.

A particularly advantageous application of the Pichia strains of the present invention (i.e., strains which are deficient in proteolytic activity) is the expression of proteolytically sensitive recombinant products, such as, for example, epidermal growth factor (EGF), growth hormone releasing factor (GRF), insulin-like growth factor-1 (IGF-1), and the like. When expressed in recombinant Pichia strains which are deficient in proteolytic activity, the resulting recombinant product is subjected to a reduced level of proteolytic activity, due to modifications in the proteolysis apparatus of the host organism. Such proteolytically deficient Pichia expression systems for the production of proteolytically sensitive products can be generated in a variety of ways. For example, Pichia host strains can be rendered proteolytically deficient, as described hereinabove, and then further transformed with DNA encoding a heterologous protein of interest (especially a proteolytically sensitive protein). Alternatively, a recombinant Pichia strain already bearing DNA encoding a heterologous protein of interest can thereafter be rendered proteolytically deficient, for example, as described hereinabove. As yet another alternative, a Pichia strain could be co-transformed with the above described modified gene and a DNA encoding a heterologous, proteolytically sensitive protein of interest.

The use of strains of the genus Pichia as host strains in the recombinant expression of peptide products has previously been described in great detail.

The presently preferred yeast species for use in the practice of the present invention is *Pichia pastoris*, a known industrial yeast strain that is capable of efficiently utilizing methanol as the sole carbon and energy source.

There are a number of methanol-responsive genes in methylotrophic yeast, the expression of each being controlled by methanol-responsive regulatory regions (also referred to as promoters). Any of such methanol-responsive promoters are suitable for use in the practice of the present invention. Examples of specific regulatory regions include the promoter for the primary alcohol oxidase gene from *Pichia pastoris* AOX1, the promoter for the secondary alcohol oxidase gene from *P. pastoris* AOX2 (*P. pastoris* is known to contain two functional alcohol oxidase genes: alcohol oxidase I (AOX1) and alcohol oxidase II (AOX2); the coding portions of the two AOX genes are closely homologous at both the DNA and the predicted amino acid sequence levels and share common restriction sites; the proteins expressed from the two genes have similar enzymatic properties but the promoter of the AOX1 gene is more efficient and gene products are frequently more highly expressed therefrom), the promoter for the dihydroxyacetone synthase gene from *P. pastoris* (DAS), the promoter for the P40 gene from *P. pastoris*, the promoter for the catalase gene from *P. pastoris*, the promoter for the formaldehyde dehydrogenase gene from *P. pastoris*, the promoter for the formate dehydrogenase gene from *P. pastoris*, and the like.

The presently preferred promoter region employed to drive expression of a gene encoding a proteolytically sensitive product, in *P. pastoris* hosts, is the promoter of the methanol-regulated primary alcohol oxidase gene of *P. pastoris*. The AOX1 gene, including its promoter, has been isolated and thoroughly characterized; see Ellis et al., *Mol. Cell. Biol.* 5:1111 (1985) and U.S. Pat. No. 4,855,231.

The presently preferred expression cassette used in transforming Pichia cells for the generation of recombinant protein-expressing strains comprises, in the reading frame direction of transcription, the following DNA sequences:

(i) a promoter region of a methanol-responsive gene of a methylotrophic yeast, (ii) a DNA sequence encoding a polypeptide consisting of:

(a) an optional secretion signal sequence, and (b) a heterologous protein of interest; and (iii) a transcription terminator functional in a methylotrophic yeast;

wherein said DNA sequences are operationally associated with one another for transcription of the sequences encoding said polypeptide. DNA sequences encoding a secretion signal sequence which are optionally contained in expression vectors used in the practice of the present invention include the DNA encoding the native secretion signal sequence associated with the proteolytically sensitive product, the DNA encoding the *S. cerevisiae* α-mating factor (αMF) leader sequence, (including a DNA sequence encoding the processing site, lys-arg), and the like.

The transcription terminator functional in a methylotrophic yeast used in accordance with the present invention has either (a) a subsegment which provides a polyadenylation signal and polyadenylation site in the transcript, and/or (b) a subsegment which provides a transcription termination signal for transcription from the promoter used in the expression cassette. The term "expression cassette" as used herein, and throughout the specification and claims, refers to a DNA sequence which includes sequences functional for the expression process. The entire transcription terminator is taken from a protein-encoding gene, which may be the same or different from the gene which is the source of the promoter.

In the DNA constructs of the present invention, used to transform hosts for recombinant expression of proteolytically sensitive products, the segments of the expression cassette(s) are said to be "operationally associated" with one another. The DNA sequence encoding proteolytically sensitive products is positioned and oriented functionally with respect to the promoter, the secretion signal sequence, if employed, and the transcription terminator. Thus, the polypeptide-encoding segment is transcribed, under regulation of the promoter region, into a transcript capable of providing, upon translation, the desired polypeptide. Appropriate reading frame positioning and orientation of the various segments of the expression cassette are within the knowledge of persons of ordinary skill in the art; further details are given in the Examples.

For the practice of the present invention it is preferred that hosts for the recombinant expression of proteolytically sensitive products be transformed with multiple copies of the above-described expression cassettes contained on one DNA fragment, preferably in a head-to-tail orientation.

In addition, when DNA constructs according to the invention are used to transform hosts for the recombinant expression of proteolytically sensitive products by site-directed integration, the expression cassette-containing construct is a linear DNA fragment that is directed to the desired locus of the host to effect integration of the DNA fragment therein. One-step gene integrations are usually successful if the DNA to be introduced has as little as 0.2 kb homology with the fragment locus of the target gene; it is however, preferable to maximize the degree of homology for efficiency.

The DNA constructs used according to the invention to transform hosts for the recombinant expression of proteolytically sensitive products optionally further comprise a selectable marker gene, in addition to one or more expression cassettes. For this purpose, any selectable marker gene functional in methylotrophic yeast may be employed, i.e., any gene which confers a phenotype upon methylotrophic yeast cells, thereby allowing them to be identified and selectively grown from among a vast majority of untransformed cells. Suitable selectable marker genes include, for example, selectable marker systems composed of an auxotrophic mutant P. pastoris host strain and a wild-type biosynthetic gene which complements the host's defect. For transformation of His4$^-$ P. pastoris strains, for example, the S. cerevisiae or P. pastoris HIS4 gene may be employed, or for transformation of Arg4$^-$ mutant P. pastoris strains, the S. cerevisiae ARG4 gene or the P. pastoris ARG4 gene may be employed, or for transformation of Ura3$^-$ mutant P. pastoris strains, the S. cerevisiae URA3 gene or the P. pastoris URA3 gene may be employed.

In addition, DNA constructs used to transform hosts for the recombinant expression of proteolytically sensitive products according to this aspect of the invention optionally further comprise selectable marker genes which are functional in bacteria. Thus, any gene can be used which confers a phenotype on bacteria that allows transformed bacterial cells to be identified and selectively grown from among a vast majority of untransformed cells. This additional selectable marker enables DNA of the invention to be transformed into bacteria such as E. coli for amplification. Suitable selectable marker genes include the ampicillin resistance gene (Amp$^r$), tetracycline resistance gene (Tc$^r$), and the like.

When it is contemplated to pass DNA of the invention though bacterial cells, it is desirable to include in the DNA construct a bacterial origin of replication, to ensure the maintenance of the invention DNA from generation to generation of the bacteria. Exemplary bacterial origins of replication include the fl-ori, colisin, col El, and the like.

The term "expression vector", as employed herein, is intended to include vectors capable of expressing DNA sequences contained therein, where such sequences are in operational association with other sequences capable of effecting their expression, i.e., promoter sequences. In general, expression vectors usually used in recombinant DNA technology are often in the form of "plasmids", i.e., circular, double-stranded DNA loops, which in their vector form are not bound to the chromosome. In the present specification the terms "vector" and "plasmid" are used interchangeably. However, the invention is intended to include other forms of expression vectors as well, which function equivalently.

Methods of transforming yeast of the genus Pichia, as well as methods applicable for culturing such yeast cells, are known generally in the art.

According to the invention, constructs containing the above-described modified gene and/or expression cassettes encoding the production of heterologous, proteolytically sensitive products are transformed into Pichia cells either by the spheroplast technique, or by the whole-cell lithium chloride yeast transformation system, as described above.

Transformed strains, which are of the desired phenotype and genotype, are grown in fermentors in either batch or continuous mode. For the large-scale production of recombinant DNA-based products in methylotrophic yeast, a three-stage, high cell-density fermentation system is the presently preferred fermentation protocol employed. In the first, or growth stage, expression hosts are cultured in defined minimal medium with an excess of a non-inducing carbon source (e.g., glycerol). When grown on such carbon sources, heterologous gene expression is completely repressed, which allows the generation of cell mass in the absence of heterologous protein expression. It is presently preferred, during this growth stage, that the pH of the medium be maintained at about 5, because the P. pastoris cells generally prefer a pH of about 5 for optimal growth. Next, a short period of non-inducing carbon source limitation growth is allowed to further increase cell mass and derepress the methanol-responsive promoter. The pH of the medium during this limitation growth period is maintained at an appropriate pH value (the actual pH employed is a function of the particular host strain used for expression and the specific product being expressed).

Subsequent to the period of growth under limiting conditions, methanol is added in the fermentor either on a continuous basis, with concurrent removal of product via the broth; or on a batch-wise basis wherein methanol is added at such a rate that the methanol content of the broth is maintained at a low level (referred to herein as "methanol excess fed-batch mode"). The addition of methanol induces the expression of the gene driven by a methanol-responsive promoter. This third stage is referred to as the production stage, because it is at this stage that the majority of the recombinant product is expressed. The pH of the medium during the production stage is maintained at an appropriate pH value (the actual pH employed is a function of the particular host strain used for expression and the specific product being expressed).

The term "culture" means a propagation of cells in a medium conducive to their growth, and all sub-cultures thereof. The term "subculture" refers to a culture of cells grown from cells of another culture (source culture), or any subculture of the source culture, regardless of the number of subculturings which have been performed between the subculture of interest and the source culture.

According to a preferred embodiment of the present invention, the heterologous protein expression system used for the production of proteolytically sensitive products utilizes the promoter derived from the methanol-regulated AOX1 gene of P. pastoris, which is very efficient and tightly regulated. This gene can be the source of the transcription terminator as well. The presently preferred expression cassette comprises, operationally associated with one another, the P. pastoris AOX1 promoter, optional DNA encoding a secretion signal sequence, a DNA sequence encoding a proteolytically sensitive product (e.g., mature IGF-1, EGF, GRF, and the like), and a transcription terminator derived from the P. pastoris AOX1 gene. Preferably, two or more of such expression cassettes are contained on one DNA fragment, in head-to-tail orientation, to yield multiple expression cassettes on a single contiguous DNA fragment.

The presently preferred host cells to be transformed with multiple expression cassettes are P. pastoris cells having at least one mutation that can be complemented with a marker gene present on a transforming DNA fragment. Preferably His4$^-$ (GS115) or Arg4$^-$ (GS190) single auxotrophic mutant P. pastoris strains are employed, or His4$^-$/Ura3$^-$ (GS4-2) or His4$^-$/Arg4$^-$ (PPF1) double auxotrophic mutant P. pastoris strains are employed.

The fragment containing one or more expression cassette(s) is inserted into a plasmid containing a marker gene complementing a metabolic defect in the host, and optionally containing additional sequences such as bacterial marker genes, yeast DNA sequences which direct vector integration, and the like.

Figure 12:
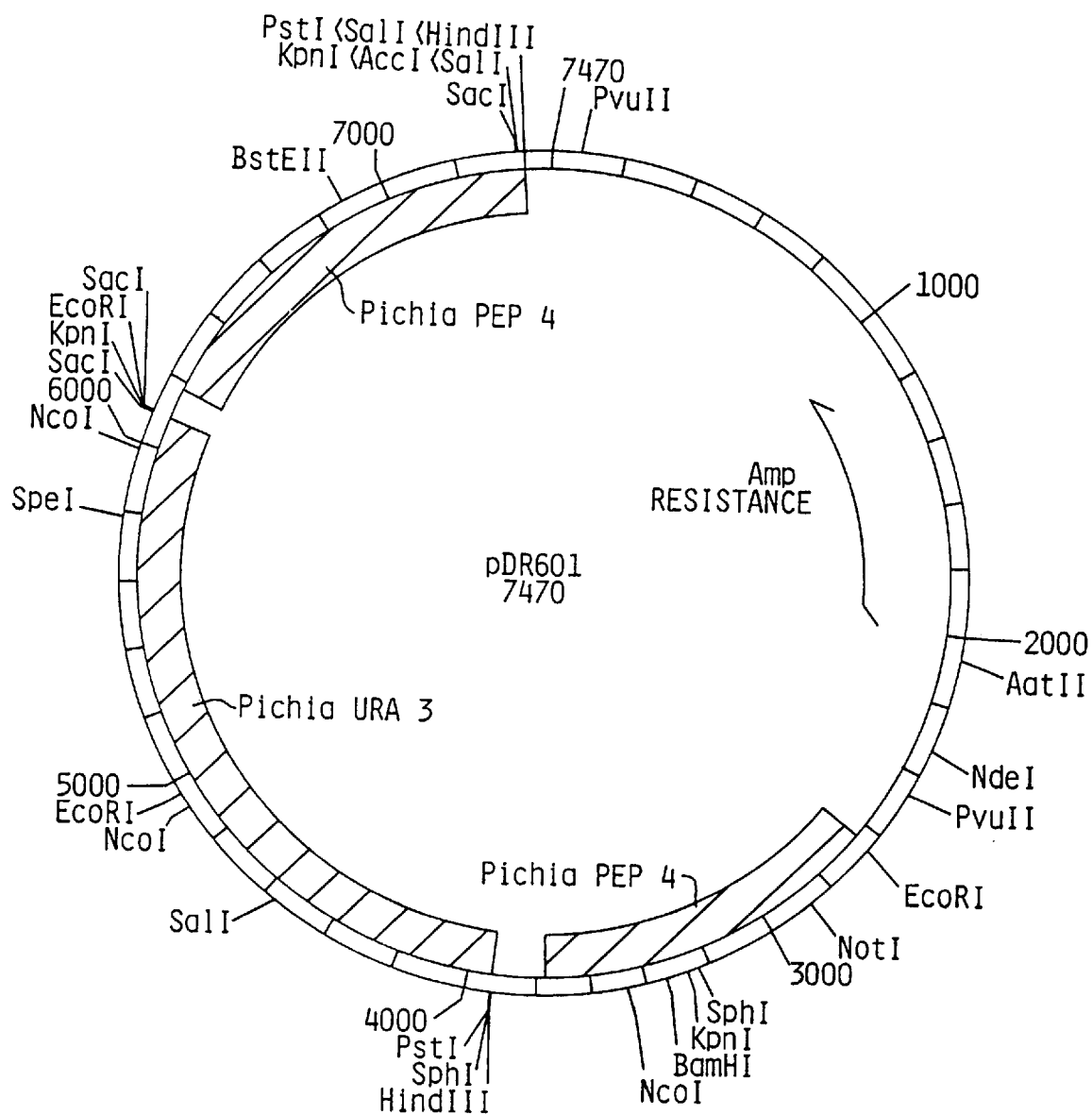
FIG. 12 is a restriction map of plasmid pDR601.

In accordance with a specific embodiment of the present invention, there is provided an isolated DNA fragment obtained from a species of the genus Pichia which comprises the orotidine-5'-phosphate decarboxylase gene. The orotidine-5'-phosphate decarboxylase gene is frequently referred to as URA3. It can be used, for example, to complement URA3-deficient strains. Another use for the novel gene is the ability to target DNA into a specific locus of the Pichia genome (i.e., into the URA3 locus). This novel gene can be characterized by reference to the restriction map shown in FIG. 12. Alternatively, this novel gene can be characterized as encoding a protein having substantially the same amino acid sequence as set forth in Sequence ID No. 4. While those of skill in the art recognize that the above-referenced amino acid sequence can be encoded by a variety of nucleotide sequences, a presently preferred nucleotide sequence encoding the above-referenced amino acid sequence is substantially the same as that set forth in Sequence ID No. 3.

In accordance with another specific embodiment of the present invention, there are provided yeast cells of the genus Pichia as a host capable of being transformed with recombinant DNA material, wherein the host is defective in the orotidine-5'-phosphate decarboxylase gene. Host strains defective in the URA3 gene can be used for transformation with DNA containing an intact form of the URA3 gene, thereby enabling a ready determination of whether the desired transformation event has occurred (by return of successfully transformed cells to uracil prototrophy).

The combination of Ura3⁻ Pichia strains and the Pichia orotidine-5'-phosphate decarboxylase marker gene provides a particularly useful selection system for use in producing recombinant strains of Pichia deficient in proteolytic activity. Such a selection system is referred to herein as a "bidirectional selection process". Application of this selection system for the generation of Pichia strains which are deficient in proteolytic activity is carried out as follows:

A Ura3⁻ host is transformed with a DNA construct containing a modified form of a gene encoding a protein involved in the Pichia proteolytic pathway, and the URA3 gene. Site-directed integration of the transforming DNA by gene addition (i.e., "pop-in") yields one functional and one non-functional gene at the locus of the gene which directly or indirectly influences proteolytic activity, as well as an intact URA3 gene. Strains which incorporate the URA3 gene are identified by positive selection (using techniques well known to those of skill in the art, e.g., by growing the strains on minimal media lacking uracil and selecting those strains capable of growth on such media). The configuration of the functional, non-functional and URA3 genes at the locus of the gene which encodes a protein which influences proteolytic activity enables recombination to occur between the functional and non-functional genes, resulting in the loss of one of these genes and the URA3 gene (i.e., "pop-out"). Thereafter, it is possible to positively select for strains lacking a functional URA3 gene by plating cells on medium containing a non-toxic analog of a uracil pathway intermediate, 5-fluoro-orotic acid (5-FOA), which, when metabolized by Ura3⁺ strains, produces a compound toxic to the cells. Because Ura3⁻ strains blocked at a specific point in the uracil pathway do not metabolize 5-FOA, they are not subjected to its toxic effects, and can thus be referred to as "5-FOA resistant". In contrast, Ura3⁺ strains metabolize 5-FOA to produce a toxic compound which will prevent growth of the Ura3⁺ cells. The resulting Ura3⁻ cells that also lack the functional target gene are deficient in proteolytic activity.

Because the Ura3⁻ phenotype is restored, the resulting cells can be transformed again using the URA3 gene as a selectable marker.

The ability to positively select strains lacking a functional URA3 gene employing a toxic analog of a uracil pathway intermediate allows the use of this very convenient "pop-out" method for imparting multiple phenotypic changes in Pichia hosts.

Ura3⁻ Pichia strains which are also deficient in proteolytic activity, relative to the proteolytic activity present in wild-type strains of the same species, are particularly useful for transformation with expression vectors which contain an intact form of the URA3 gene, and a gene encoding a proteolytically sensitive product (either as part of the same vector, or as a second vector which is transformed into the host). Those transformants which return to uracil prototrophy (which can be readily determined by simple screening procedures) should have incorporated therein the gene encoding a proteolytically sensitive product, and thus would be directly applicable to product expression.

The invention will now be described in greater detail by reference to the following non-limiting examples.

EXAMPLES

Example I

Isolation of the *P. pastoris* PEP4 Gene

The *P. pastoris* PEP4 gene was identified in a bacteriophage lambda-based EMBL3 *P. pastoris* genomic DNA library by its ability to hybridize with a radiolabeled fragment of the homologous *Saccharomyces cerevisiae* PEP4 gene. The *P. pastoris* PEP4 gene was cloned by isolating positive plaques containing the hybridizing recombinant phage DNA.

A. Construction of a *P. pastoris* EMBL3 Genomic DNA Library

Bacteriophage λ was used as a vehicle for cloning the *P. pastoris* PEP4 gene. Fragments of a partial Sau3A digest of *P. pastoris* genomic DNA were inserted into the bacteriophage λ vector EMBL3, which contains elements of the bacteriophage λ genome essential for propagation of the recombinant DNA in bacterial hosts. The *P. pastoris* DNA-containing EMBL3 vectors were packaged in vitro into infectious virions to yield a bacteriophage λ *P. pastoris* genomic DNA library. Amplification of the library was achieved by propagation of the recombinant DNA in *Escherichia coli* host cells that had been infected with the recombinant virus.

EMBL3 [Frischauf, A.-M. et al. (1983). *J. Mol. Biol.* 170:827] is a replacement vector capable of incorporating fragments of genomic DNA ranging in size from 9 to 23 kb. This vector contains a segment of nonessential bacteriophage λ DNA (stuffer fragment) that is delineated by a pair of restriction sites (RamHI/EcoRI) located at both ends of the segment in opposite orientations (i,e., 5' BamHI-EcoRI-stuffer-EcoRI-BamHI 3'). Foreign DNA fragments containing BamHI-compatible ends (e.g., Sau3A termini) are incorporated into the vector by replacement of the stuffer fragment.

*Pichia pastoris* genomic DNA (from strain NRRL Y-11430, from the Northern Regional Research Center, Peoria, Ill.) isolated using a glass rod swirl technique [Cregg et al. *Mol. Cell. Biol.* 5:3376–3385 (1985)] was digested with Sau3A at an effective concentration of 0.1 u/μg in 7, 14, 21 and 28 minute incubations conducted at 37° C. An aliquot from each incubation mixture was electrophoretically separated on a 1% agarose gel to determine the sizes of the digested DNA fragments. Digests incubated for 7 and 14 minutes appeared to consist primarily of 9–23 kb fragments. These digests were pooled and ligated to EMBL3 vector arms, prepared as described below.

EMBL3 vector arms were prepared by double digestion of the vector (obtained from EMBL3 Cloning Kit, Stratagene Cloning Systems, San Diego, Calif.; catalog #241211) with BamHI and EcoRI. The small BamHI/EcoRI linker that separates the arms from the stuffer fragment was removed from the digest by selective precipitation with ethanol. Because the arms end in BamHI termini and the stuffer sequence is contained in an EcoRI fragment, the arms were unable to relegate to the stuffer fragment. Therefore, following removal of the BamHI/EcoRI linker, it was not necessary to separate the arms from the stuffer fragment prior to ligation of the arms and the genomic DNA inserts. Ligation of the Sau3A-digested Pichia genomic DNA (0.5 $\mu$g) to 1 $\mu$g of EMBL3 pre-digested arms was accomplished by incubation of the 5-$\mu$l reaction mixture at 4° C. for two days.

The recombinant bacteriophage $\lambda$ DNA prepared by ligation of $P.$ $pastoris$ genomic DNA fragments and EMBL3 vector arms was packaged in vitro using commercial packaging extracts (stratagene EMBL3 Cloning Kit). The efficiency of packaging was determined by plating an aliquot of the packaged library and the $E.$ $coli$ lysogenic host strain VSC 257 onto NZY (5 g NaCl, 2 g MgSO$_4$.H$_2$O', 5 g yeast extract, 10 g NZ amine and 20 g agar per liter) plates. The efficiency of packaging was calculated and determined to be $1.2 \times 10^6$ plaques/$\mu$g.

The EMBL3-based $P.$ $pastoris$ genomic library was amplified by plating the recombinant phage along with the $E.$ $coli$ lysogenic host strain P2 392 (provided in Stratagene EMBL3 Cloning Kit) which contains prophage P2. Wild-type bacteriophage do not grow in $E.$ $coli$ strain P2 392. Recombinant EMBL3-based bacteriophage, created by replacing the stuffer fragment of EMBL3 with foreign DNA, lack two of the wild-type genes that confer P2 sensitivity, which were contained in the stuffer fragment. Therefore, the recombinant bacteriophage are able to grow well in this P2-containing $E.$ $coli$ strain. The use of $E.$ $coli$ P2 392 as the host strain in the amplification ensured that only recombinant phage would be reproduced in the bacterial host. All of the plates encompassing the EMBL3-based $P.$ $pastoris$ genomic DNA library were overlayed with SM buffer (5.8 g NaCl, 2 g MgSO$_4$.H$_2$O, 50 ml 1M Tris.HCl, pH 7.5, and 5 ml 2% gelatin per liter). After five hours, the supernatants were collected and pooled, and the titer and genome equivalents were calculated according to the manufacturer's instructions. The library contained approximately 10 genome equivalents, and its titer was $6 \times 10^{11}$ plaque-forming units/ml (pfu/ml).

B. Screening of the EMBL3 $P.$ $pastoris$ Genomic DNA Library Using the $S.$ $cerevisiae$ PEP4 Gene as a Probe In order to adequately screen the Pichia genome for the PEP4 gene, 50,000 recombinant phage and the $E.$ $coli$ lysogenic host strain LE 392 (provided in Stratagene EMBL3 Cloning Kit) were plated onto four large 150-mm plates. After 6–7 hours of growth, the plates were chilled to 4° C. Each plate was marked and duplicate plaque lifts of each plate were prepared by placing nitrocellulose onto each plate. The filters were denatured, neutralized, baked and probed with the $S.$ $cerevisiae$ PEP4 gene [a gel-purified, $^{32}$P-labeled 4.0 kb fragment of $S.$ $cerevisiae$ DNA containing the $S.$ $cerevisiae$ PEP4 gene obtained from the laboratory of Thomas Stevens, University of Oregon, Eugene, Oreg.; see Rothman et al., Proc. Natl. Acad. Sci. USA 83: 3248–3252 (1986)]. Hybridization was conducted at 37° C. in a solution containing 30% formamide, 6$\times$ SSC, 5$\times$ Denhardt's solution, 20 mM Tris.HCl, pH 8.0, 1 mM EDTA, 0.1% SDS and 100 $\mu$g/ml salmon sperm DNA. After hybridization, the filters were washed three times at room temperature using 2$\times$ SSC and 0.1% SDS. Following these initial washes, the filters were then washed twice at 55° C. using 2$\times$ SSC and 0.1% SDS.

Fifteen positive plaques containing DNA that hybridized to the fragment of the $S.$ $cerevisiae$ PEP4 gene were identified in duplicate from autoradiograms of the filters. The area around each of the 15 positive plaques was isolated and placed in SM buffer. Six of the isolates were plated at dilutions of $10^{-5}$ and $10^{-7}$ with $E.$ $coli$ strain LE 392 onto smaller 100-mm plates. Single plaque lifts of each plate were probed with the $S.$ $cerevisiae$ PEP4 gene fragment under the same hybridization and wash conditions used in the first plaque screening. In this second round of screening, 12 positive plaques were detected on the autoradiogram. Nine of these single plaques were isolated and placed in SM buffer. Each of these nine plaques was plated at dilutions of $10^{-5}$ and $10^{-7}$ with $E.$ $coli$ strain LE 392 onto small 100-mm plates. Again, single plaque lifts of each plate were probed with the $S.$ $cerevisiae$ PEP4 gene fragment under the same hybridization and wash conditions used in the first two screenings. Each plate contained approximately 10–20 plaques distributed evenly across the plate. Autoradiograms of the filters revealed that every plaque on each plate hybridized to the PEP4 probe.

Five separate plaques from different plates were isolated and placed in SM buffer. DNA from large-scale cultures of three of these isolates, designated 4721, 5111 and 5131, respectively, was prepared using the induction method of bacteriophage isolation [Maniatis, T., Fritsch, E. F. and Sambrook, J. *Molecular Cloning, A Laboratory Manual.* Cold Spring Harbor Laboratory Press, Cold Spring Harbor, N.Y., USA (1982)] in order to identify, characterize and subclone the PEP4 gene contained in the recombinant phage.

C. Characterization of the Insert in Isolates of the EMBL3 $P.$ $pastoris$ Genomic DNA Library that Hybridized to the $S.$ $cerevisiae$ PEP4 Gene Recombinant phage DNAs of the three isolates referred to above of the EMBL3 Pichia genomic DNA library (4721, 5111 and 5131) were digested with various restriction endonucleases, separated on a 0.8% agarose gel and visualized by ethidium bromide staining. In addition, 1 $\mu$l aliquots of these digests were separated on a second agarose gel which was blotted onto nitrocellulose and probed with the radiolabeled $S.$ $cerevisiae$ PEP4 gene fragment. Hybridization was conducted at 37° C. in a solution containing 30% formamide, 6$\times$ SSC, 5$\times$ Denhardt's solution, 20 mM Tris.HCl, pH 8.0, 1 mM EDTA, 0.1% SDS and 100 $\mu$g/ml salmon sperm DNA. The filter was then washed in three 5-minute washes at room temperature with 2$\times$ SSC and 0.1% SDS followed by two 5-minute washes at 55° C. with 2$\times$ SSC and 0.1% SDS.

Identical digests of DNA from two of the clones, 5111 and 5131, yielded the same pattern of restriction enzyme fragments, as determined by ethidium bromide staining, whereas the same digest of DNA from the third clone, 4721, yielded a different fragment pattern. Analysis of the restriction enzyme fragments of DNA from each clone by Southern blot hybridization to the $S.$ $cerevisiae$ PEP4 gene fragment revealed that the two classes of clones both contained a series of hybridizing fragments of the same size indicating that the two classes of clones had a common overlapping DNA sequence that hybridized with the probe.

D. Subcloning and Characterization of the Cloned P. pastoris PEP4 Gene

As determined by Southern blot hybridization of EcoRI-digested P. pastoris genomic DNA using the homologous S. cerevisiae PEP4 gene as a probe, the P. pastoris PEP4 gene is contained within a 10.6 kb EcoRI fragment of the P. Rastoris genome. Southern blot hybridization of EcoRI-digested DNA of clone 4721, as described in Example IC, revealed that it contained a 10.6 kb fragment that hybridized to the S. cerevisiae PEP4 gene. To facilitate manipulation of the cloned P. pastoris PEP4 gene, P. pastoris genomic DNA contained on an EcoRI fragment of DNA from isolate 4721 was subcloned into pUC19. Clone 4721 (25 μg) was digested with EcoRI (60 units) in a total volume of 300 μl. The digested DNA was separated on a 0.65% agarose gel, and the 10.6 kb EcoRI fragment was isolated with DE81 paper. The purified fragment was washed from the paper with 400 μl of 1M NaCl and extracted with phenol/chloroform. The DNA was then precipitated with ethanol and resuspended in water to a total volume of 10 μl. Approximately 50 ng of the 10.6 kb fragment were ligated with an equal amount of pUC19 which had been cut with EcoRI and dephosphorylated. The ligation mixture was used to transform E. coli strain MC1061. Ampicillin-resistant colonies were selected and screened by analysis of restriction enzyme digests of colony DNA for the presence of the diagnostic 10.6 kb EcoRI fragment. A large-scale plasmid preparation was made from a colony containing the correct plasmid, which was named pEP202. Plasmid pEP202 contains the complete P. pastoris PEP4 gene (see FIG. 1).

Figure 2:
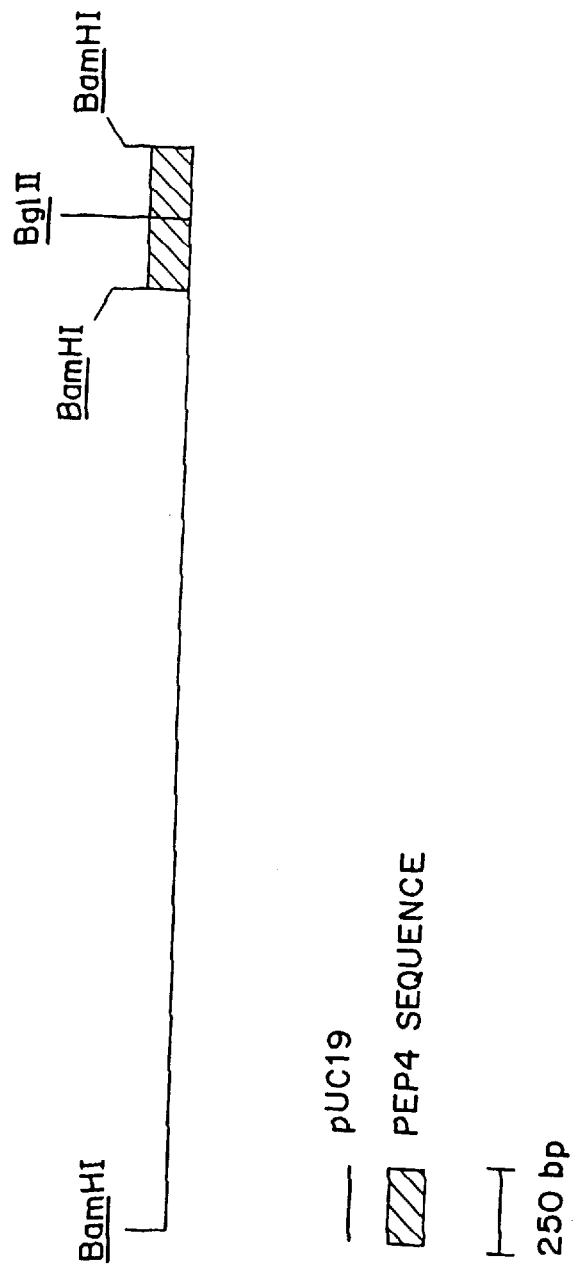
FIG. 2 is a restriction map of plasmid pEP205.

To facilitate sequence analysis of the cloned P. pastoris PEP4 gene, a portion of the P. pastoris PEP4 gene was subcloned into pUC19. Plasmid pEP202 was digested with BamHI and EcoRI. The reaction mixture was separated on a 0.7% agarose gel, and the 0.45 kb BamHI fragment of DNA (see FIG. 2) was isolated using DE81 paper. The purified fragment was ligated to pUC19 (~20 ng) that had been linearized by digestion with BamHI and dephosphorylated. The ligation mixture was used to transform E. coli strain MC1061. Transformants were selected for ampicillin resistance and screened by analysis of restriction enzyme digests of colony DNA for the presence of a single BamHI fragment. A single colony arising from this transformation was found to contain the appropriate DNA construct, and was named pEP205 (see FIG. 2).

Sequence analysis of plasmid pEP202 identified a DNA sequence with ~70% homology to the PEP4 gene of S. cerevisiae. The amino acid sequence encoded by this DNA sequence of pEP202 is 69% homologous to that encoded by the S. cerevisiae PEP4 gene.

Example II

Development of a PEP4-deficient (Pep4⁻) Strain of P. pastoris

A. Construction of the P. pastoris PEP4 Gene Disruption Vector yDR401

Figure 3:
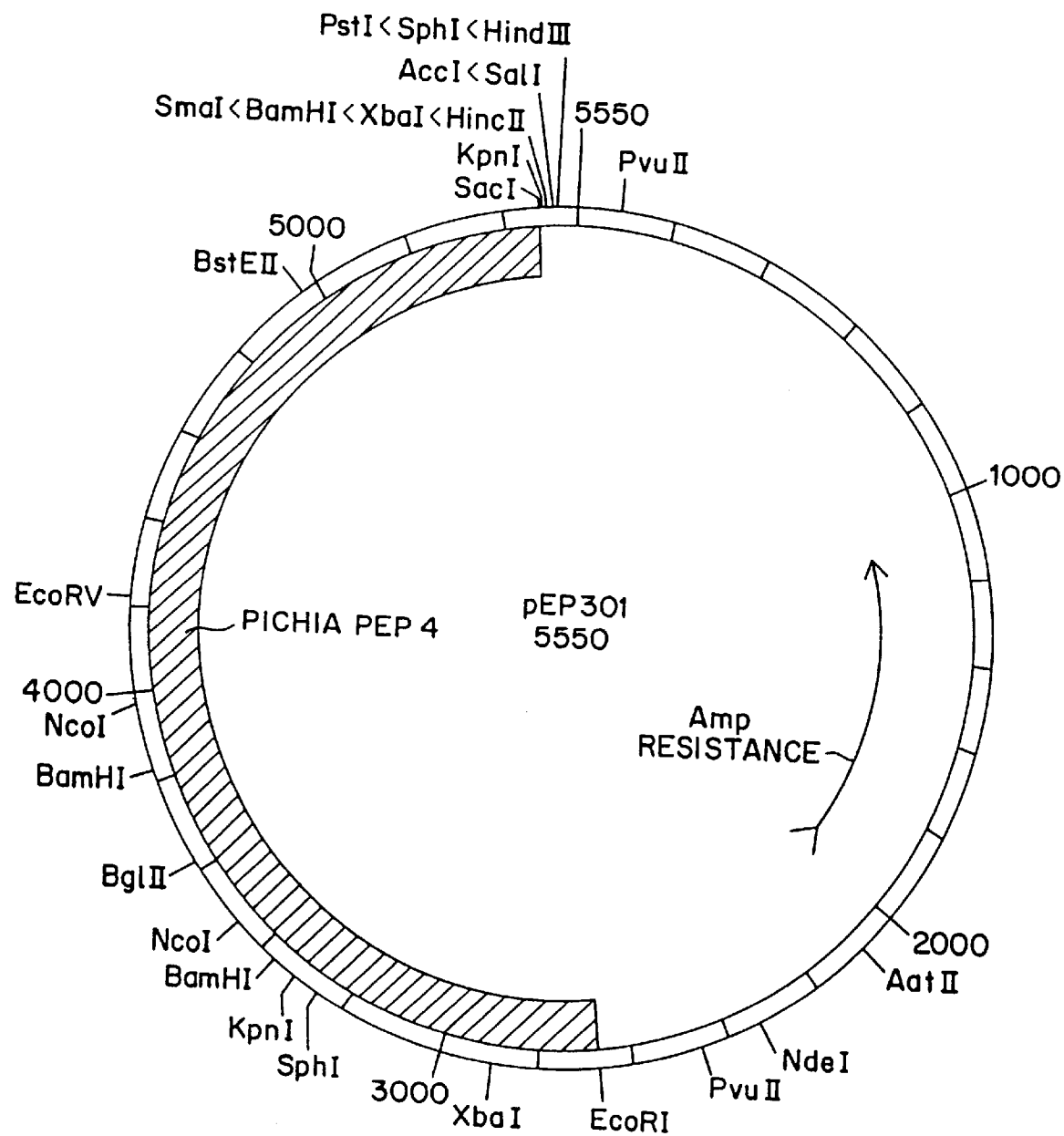
FIG. 3 is a restriction map of plasmid pEP301.

Vector pDR401 was constructed for use in developing a PEP4-deficient (Pep4⁻) strain of P. pastoris. This vector contains a defective P. pastoris PEP4 gene, which, when used to transform PEP4 strains of P. pastoris, integrates into the host genome by replacement of the wild-type PEP4 gene.

pDR401 was constructed in a two-step procedure as follows. In the first step, the base vector in the construction of pDR401, base vector pEP301, was constructed from pEP202. Vector pEP301 consists of pUC19 sequences and the cloned P. pastoris PEP4 gene from pEP202. Plasmid pEP202 (15 μg) was digested with SacI. A 5.5 kb SacI fragment (the fragment extending from the SacI linker clockwise to the SacI site at ~5:00, and containing all of the pUC19 sequence and the entire PEP4 gene; see FIG. 1) was isolated from a 0.7% agarose gel using DE81 paper. The fragment was eluted from the paper with 400 μl of 1M NaCl, extracted with 400 μl of phenol/chloroform and precipitated with ethanol. This DNA was then ligated with itself in a volume of 100 μl containing 1 μl of ligase and 1 μl (~10 ng) of DNA. The ligation mixture was incubated at room temperature for 1 hr and then used to transform E. coli strain MC1061. Ampicillin-resistant colonies were selected and screened by analysis of restriction enzyme digests of colony DNA for the presence of a single 5.5 kb BglII fragment. Plasmid DNA was prepared from a transformed colony of MC1061 that contained the correct plasmid, which was named pEP301 (FIG. 3).

Figure 4:
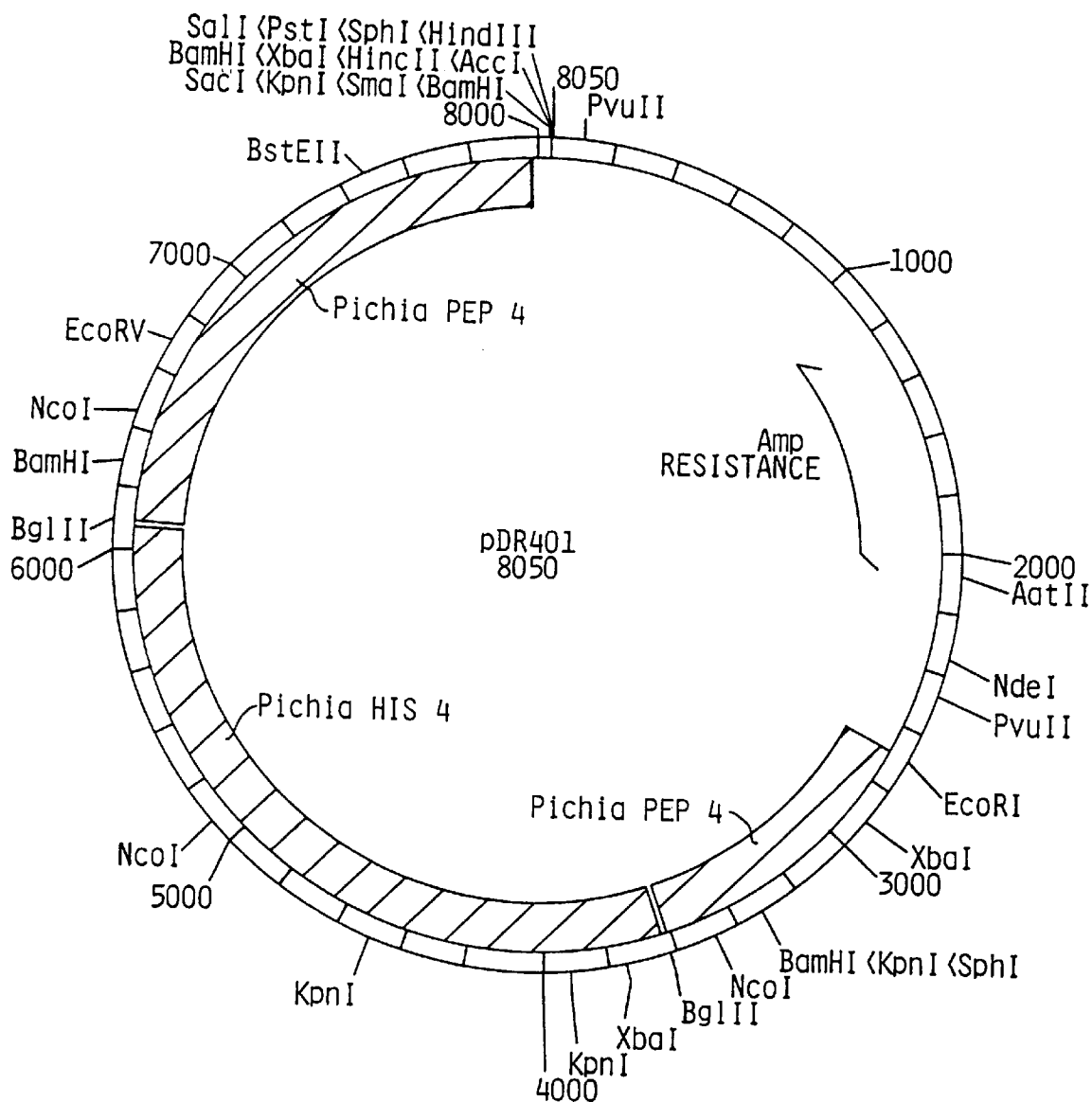
FIG. 4 is a restriction map of plasmid pDR401.

In the second step of the construction of pDR401, the P. pastoris HIS4 gene was inserted into the PEP4-containing plasmid pEP301 to yield the final vector. The P. pastoris HIS4 gene was isolated on a 2.6 kb BglII fragment derived from pYJ8ΔCla [Cregg, J. et al. Mol. Cell. Biol. 5:3376–3385 (1985)]. Plasmid pYJ8ΔCla (15 μg) was digested with BglII and the digested DNA was separated on a 0.7% agarose gel. The HIS4 gene-containing 2.6 kb fragment was isolated with DE81 paper, eluted with 400 μl of 1M NaCl, extracted with 400 μl of phenol/chloroform, precipitated with ethanol and resuspended in 10 μl of water. Prior to inserting this 2.6 kb BglII fragment into the unique BglII site of pEP301, approximately 20 μg of pEP301 were digested with BglII, dephosphorylated and extracted with phenol/chloroform. The 2.6 kb HIS4-containing fragment was then inserted into pEP301 by ligation of approximately 50 ng of the fragment to approximately 50 ng of the BglII-digested pEP301 in a total volume of 10 μl containing 1 μl of buffer, 1 μl of ligase and water. Ligation was conducted at room temperature for 3 hrs and the ligation mix was used to transform MC1061 cells. Plasmid DNA prepared from an ampicillin-resistant colony was digested with BglII, SalI, BqlII/SalI, PvuI, NcoI and KpnI to confirm the construction of pDR401. The restriction fragment pattern was consistent with that expected for the correct plasmid pDR401 (see FIG. 4). Plasmid pDR401 is pUC19 with the P. pastoris HIS4 gene inserted at the unique BglII site within the PEP4 structural gene, thus disrupting it.

B. Transformation of his4 P. pastoris strain GS115 with a Fragment of pDR401

In order to create a pep4 strain of P. pastoris, the his4 PEP4 P. pastoris strain GS115 (ATCC 20864) was transformed with 20 μg of the 5.3 kb EcoRI/SacI fragment of pDR401 according to the spheroplast method (see U.S. Pat. No. 4,879,231). This fragment of pDR401 consists of the HIS4 gene-containing defective pep4 gene. Transformant strains resulting from this type of integration are prototrophic and can be distinguished from untransformed cells on this basis. The frequency of transformation was approximately $10^3$ μg$^{-1}$ DNA.

C. Characterization of Transformants

1. Analysis of transformant carboxypeptidase Y activities

His⁺ transformants were subsequently analyzed for carboxypeptidase Y activity using a colony overlay calorimetric screening procedure [see Jones, E. in Genetics 85: 23–33 (1977)]. In this assay, the His⁺ transformant cells were released from the transformation agar plates and grown on YEPD (yeast extract, 1% peptone, 2% dextrose and 2% agar) plates at a density of ~300 colonies per plate. The plates were overlayed with 0.6% agarose containing 40% dimethylformamide (DMF) to permeabilize the cells, and 1.2 mg/ml of the substrate APNE (N-acetyl DL phenylalanine β-napthyl ester). Because the cells were permeabilized, some of the vacuolar content of the cell was accessible to the reagent APNE. After the agarose overlay had solidified, the plates were soaked in a solution of 5 mg/ml Fast garnet salt. APNE is cleaved by the esterolytic activity of carboxypeptidase Y. The products of this reaction bind the fast garnet salt to produce a red color in the colony. Colonies lacking carboxypeptidase Y activity do not bind the salt and therefore stain less intensely than do colonies that possess this activity. Pep4$^+$ colonies developed a red/pink center during the first 10–15 minutes after exposure to the garnet salt. In contrast, colonies defective at the PEP4 locus were slow to develop this color and were distinguished as pink relative to the red Pep4$^+$ colonies. Colonies that appeared to have low carboxypeptidase Y activities based on the results of this assay (i.e., colonies that failed to develop a strong red color indicative of Pep4$^+$ colonies) were isolated, transferred to a master plate, subcultured along with control colonies and re-screened using the overlay assay. Twenty colonies which again failed to develop a strong red color were selected for analysis by Southern blot hybridization to determine if the PEP4 locus of these transformants had been disrupted by integration of the fragment of vector pDR401.

2. Southern blot hybridization analysis of transformant DNA

Genomic DNA was extracted from 20 transformant strains that exhibited low carboxypeptidase activity, designated p1–p20, and digested with SacI and EcoRI. This procedure should liberate the HIS4-containing defective pep4 gene as the 5.3 kb EcoRI/SacI fragment that was used to transform the strains. Two Southern blot filters were prepared from these digested DNAs; one blot was probed with a radiolabeled 1.4 kb XbaI/EcoRV fragment from pEP301 (see FIG. 3), which contained a portion of the cloned *P. pastoris* PEP4 gene and the other blot was probed with a radiolabeled 2.6 kb BglII fragment of pDR401 containing the HIS4 gene. Control DNA from the transformation host strain GS115, which had been digested with SacI and EcoRI, was included in this analysis for comparative purposes.

Digestion of genomic DNA from GS115 with SacI and EcoRI yielded a 2.9 kb fragment that hybridized to the portion of the PEP4 gene contained in the radiolabeled XbaI/EcoRV fragment of pEP301. In contrast, this probe hybridized to fragments of a different size in SacI/EcoRI-digested DNA from 19 of the 20 transformants analyzed. Only DNA from strain p17 yielded a hybridization pattern identical to that of DNA from the parental strain. The remaining 19 strains lacked a 2.9 kb hybridizing fragment characteristic of an undisrupted PEP4 locus and contained an approximately 5.3 kb fragment and/or larger fragments that hybridized to the PEP4 gene probe. The 5.3 kb fragment was the same size as the transforming DNA released from vector pDR401 upon digestion with SacI and EcoRI.

The results of Southern blot hybridization of DNA from strains p1–p16 and p18–p20 revealed that these strains contained a defective pep4 gene with an intact HIS4 gene therein, and that the PEP4 locus of the strains had been disrupted. Strain p13 was grown in a one-liter fermentation, as described in Example III, in order to analyze the proteolytic activity of the broth of a larger culture of a pep4 strain of *P. pastoris*.

3. Analysis of the transformant proteinase A activities a. Protocol

The proteinase A activities of eight transformant strains were evaluated using an enzyme assay based on the method of Jones et al. [Genetics 102:655 (1982)]. Several control strains were also evaluated in this assay: PEP4 and pep4 strains of *S. cerevisiae* (strains DBY747 and 20B12, respectively, from the Yeast Genetic Stock Center, University of California, Berkeley, Calif.) and a PEP4 wild-type strain of *P. pastoris* (strain NRRL Y-11430 from the Northern Regional Research Center, Peoria, Ill.).

Proteinase A is a vacuolar enzyme responsible for the aspartyl protease activity encoded by the PEP4 gene in *S. cerevisiae*. The procedure used to evaluate the proteinase activities of transformant cell extracts is based on the measurement of proteinase A-mediated release of amino acids from acid-denatured hemoglobin. Transformant cell extracts were incubated with acid-denatured hemoglobin, and the proteinase A activity present in the extract was determined by estimating the difference in the amount of amino acid released at time zero and after 90 minutes of incubation.

Cultures of the *S. cerevisiae* control strains DBY747 (PEP4) and 20B12 (pep4), the PEP4 *P. pastoris* strain NRRL Y-11430 and the experimental PEP4 strains of *P. pastoris* were grown to stationary phase in YEPD medium. Cultured cells (20 OD$_{600}$ units) were washed in 10 mM sodium azide and then lysed in 400 μl of 100 mM Tris, pH 7.5, by vortexing the cells with acid-washed glass beads for one minute. The lysed cells were centrifuged in Eppendorf tubes for 10 minutes to remove cell debris. The supernatant obtained after centrifugation (crude extract) was then examined for proteinase A activity as follows. Acid-denatured 1% hemoglobin (400 μl) was added to 50 μl of crude extract and incubated for 90 minutes at 37° C. Reactions were stopped by the addition of 0.2 ml of 1N perchloric acid. Insoluble material was removed by centrifugation, and 200 μl of 0.31M NaCl was added to 200 μl of supernatant. A 40 μl aliquot of this solution was then assayed using the Pierce BCA protein assay kit (see, for example, U.S. Pat. No. 4,839,295) for free amino acids. The amount of free amino acids present in the sample that had been incubated for 90 minutes was compared to the amount present in a blank which consisted of a sample of a reaction mixture that was stopped at zero minutes. The relative difference in free amino acids between these two samples is a measure of proteinase A activity.

b. Results

The results of proteinase A assays of control and transformant strains (see Table I; ΔOD is a measure of the concentration of free amino acids in the sample) indicate that the proteinase A activity of the pep4 strain of *S. cerevisiae* represents only 10% of that of the PEP4 strain of *S. cerevisiae*. Similarly, the proteinase A activities of the pep4 transformant strains (strains p1, p2, p5, p8, p13, p16 and p20) also are only approximately one-tenth of that of the PEP4 strain of *S. cerevisiae*. The PEP4 wild-type strain of *P. pastoris* displayed approximately half of the proteinase A activity of the PEP4 strain of *S. cerevisiae*.

TABLE I

PROTEINASE A ASSAY RESULTS

| Strain | Phenotype | AOD/ug protein |
|---|---|---|
| DBY747 (S. cerevisiae) | Pep4+ | 28.1 |
| 20B12 (S. cerevisiae) | Pep4- | 2.7 |
| P. pastoris control (NRRL Y-11430) | Pep4+ | 13.1 |
| p13 | Pep4- | 3.3 |
| p20 | Pep4- | 4.2 |
| p17 | Pep4+ (?) | 7.5 |
| p16 | Pep4- | 0 |
| p16 | Pep4- | 0 |
| p13 | Pep4- | 3.3 |
| p8 | Pep4- | 3.3 |
| p5 | Pep4- | 5.0 |
| p2 | Pep4- | 6.6 |
| p1 | Pep4- | 6.0 |

The data obtained in proteinase A assays of pep4 *P. pastoris* strains generated by transformation of a PEP4 strain with a defective pep4 gene are consistent with the results of Southern blot analyses of DNA from these transformants which indicate that the PEP4 locus of the transformants was disrupted upon transformation.

Example III

Fermentation of a pep4 Strain of *P. pastoris*

A. Procedure

A Pep4 strain of *P. pastoris*, p13, generated by transformation of strain GS115 with a defective pep4 gene-containing SacI/EcoRI fragment of vector pDR401, was grown in a one-liter fermentation according to a three-phase protocol consisting of a glycerol batch growth phase, a limited glycerol fed-batch phase and a methanol fed-batch phase as follows.

A two-liter fermentor was autoclaved with 1000 ml of minimal salts medium (21 ml 85% phosphoric acid, 0.9 g calcium sulfate.2H$_2$O, 14.3 g potassium sulfate, 11.7 g magnesium sulfate and 3.2 g potassium hydroxide) and 2% glycerol. After sterilization, 4 ml PTM$_1$ trace salts solution (6 g/l cupric sulfate.5H$_2$O, 0.8 g/l sodium iodide, 3 g/l manganese sulfate.H$_2$O, 0.2 g/l sodium molybdate. 2H$_2$O, 0.02 g/l boric acid, 0.5 g/l cobalt chloride, 20 g/l zinc chloride, 65 g/l ferrous sulfate.H$_2$O, 0.2 g/l biotin and 5 ml sulfuric acid) were added to the fermentor and the pH was adjusted to 5 with concentrated NH$_4$OH. The pH of the medium was maintained at 5 by addition of 50% NH$_4$OH containing 0.1% Struktol J673 antifoam. Inocula were prepared from buffered yeast nitrogen base (YNB) glycerol plates (phosphate-buffered YNB, 2% glycerol, 2% agar) and grown overnight at 30° C. in phosphate-buffered YNB (11.5 g/L KH$_2$PO$_4$, 2.66 g/L K$_2$HPO$_4$, 0.67% yeast nitrogen base, pH 5) containing 2% glycerol. The fermentor was inoculated with 10–50 ml of the cultured cells which had grown to an OD$_{600}$ of 1–8, and the batch growth regimen was continued for approximately one day until glycerol was exhausted. At the point of glycerol exhaustion, as indicated by increased dissolved oxygen, a glycerol feed (50% glycerol plus 12 ml/L of PTM$_1$) was initiated at 10 ml/h and continued until 40 ml of glycerol feed had been added. After termination of the glycerol feed, a methanol feed (100% methanol plus 12 ml/L PTM,) was started at an initial rate of approximately 2 ml/h. After 3 hours, the methanol feed rate was increased to 6 ml/h. The methanol feed rate was maintained at 6 ml/h for 12–18 hours and was then increased to 10 ml/h and maintained at 10 ml/h for the duration of the fermentation. The vessel was harvested after 400 ml of methanol had been added to the fermentor.

B. Sample Preparation

Samples (15 ml aliquots) of the fermentor culture were removed from the fermentor at various time intervals throughout the course of the fermentation. Aliquots of each sample were centrifuged at 6500×g for 5 minutes to separate broth and cells. The levels of the NH$_4$OH, antifoam, glycerol, and methanol reservoirs were recorded at these time points. Methanol and ethanol concentrations in the supernatant were determined by gas chromatography using a PorapakQ column (Alltech).

In addition, the wet weight of the culture was determined as an indicator of cell growth in the fermentor. For this purpose, a one ml aliquot of the fermentor culture was centrifuged for four minutes in a microfuge, the supernatant was decanted, and the wet pellet was weighed.

C. Results

Growth of the pep4 strain of *P. pastoris* p13 in a one-liter fermentation was monitored by determining the wet cell weight of the fermentor culture (in g/l) at various times during the fermentation. A time course of the growth of strain p13 during the methanol fed-batch phase of the fermentation, when compared with the time course of the growth of the HIS4 PEP4 strain G+PA0804H2 (generated by transformation of the his4 PEP4 *P. pastoris* strain GS115 with an expression vector containing the wild-type HIS4 gene) during a similar one liter fermentation, demonstrates that the growth capabilities of the pep4 strain of *P. pastoris* are comparable to those of a PEP4 strain.

Example IV

Analysis of the Proteolytic Activity of the Broth of a pep4 Strain of *P. pastoris* Grown in a One-liter Fermentation To determine if disruption of the *P. pastoris* PEP4 gene was associated with a change in the proteolytic activity of the broth of *P. pastoris*, the proteolytic activities of the broths from one-liter fermentations of a pep4 strain, strain p13, and a PEP4 strain were compared. In this study, two different peptides, epidermal growth factor (EGF; a recombinantly synthesized molecule consisting of the first 52 amino acids of the authentic 53 amino acid EGF molecule, as described in U.S. patent application Ser. No. 323,964) and growth hormone releasing factor (GRF; recombinantly synthesized as described in EP 206783) were separately incubated at room temperature in cell-free broth from the one-liter fermentation of the pep4 *P. pastoris* strain p13, and in the cell-free broth from a similar one-liter fermentation of the HIS4 PEP4 *P. pastoris* strain G+PA0804H2. After incubation for a specified period, aliquots of each incubation mixture were examined by reverse phase high performance liquid chromatography (HPLC) (details of the HPLC protocol are provided below) to determine the amount of intact peptide remaining in each sample (i.e., to determine the extent of proteolytic degradation of the peptide).

A. Reverse-Phase High-Performance Liquid Chromatography (HPLC)

A Waters 600 (Bedford, Mass.) solvent delivery system, Waters Model 481 Lambda Max variable wavelength detector, Wisp 710B autoinjector and a Shimadzu Chrom-Pac integrator (Cole Scientific, Moorepark, Calif.) constituted the reverse-phase HPLC system utilized in the analysis of EGF and GRF peptides contained in buffer and broth from fermentations of *P. pastoris* strains. Samples of broth from the fermentations of the pep4 *P. pastoris* strain p13 and the HIS4 PEP4 P. pastoris strain G+PA0804H2 were diluted 1:10 in 0.1M sodium phosphate, pH 5.0. Fifteen microliters of concentrated GRF stock was added to 285 µl of diluted broth and incubated for four hours. A similar dilution of GRF stock in the phosphate buffer was also incubated for four hours as a control. Sixty microliters of EGF stock were added to 240 µl of diluted broth or buffer and incubated for eight hours. Samples of each incubation mixture were separately injected into a Waters µ Bondapak C18 reverse phase column. The peptides were eluted from the column in a 20-minute linear gradient of 20–60% mobile phase B (95% acetonitrile, 5% water, 0.1% trifluoroacetic acid). Mobile phase A (0.1% trifluoroacetic acid) was used to dilute mobile phase B in preparing the elution gradient.

B. Results

The amount of intact peptide (of the EGF or GRF molecules that were incubated in the fermentation broth of the pep4 P. pastoris strain p13 and the broth of the PEP4 P. pastoris strain G+PA0804H2) was evaluated by comparing chromatograms obtained in HPLC analyses of intact EGF or GRF contained in 0.1M sodium phosphate buffer, pH 5.0, and of EGF or GRF contained in broth. Chromatograms from HPLC analyses of the standard intact peptides consist of a major peak reflecting the amount of the standard peptide present in the sample and the retention time characteristic of the peptide. In contrast, proteolytic fragments of either peptide are retained on the HPLC column for varying lengths of time that differ from the retention time associated with the intact peptide. Therefore, chromatograms from HPLC analysis of proteolytic fragments of either peptide (EGF or GRF) differ from chromatograms generated in HPLC analyses of intact peptides in terms of the number and sizes of the peaks and the retention times associated with the fragmented species. Based on these differences, it was possible to estimate the amount of intact EGF or GRF peptide in the broth incubation samples.

Based on HPLC analyses of GRF and EGF samples incubated in PEP4 P. pastoris control broth, it has been determined that less than 10% of each of the two peptides remains intact after incubation in broth from the fermentation of the PEP4 strain G+PA0804H2. In contrast, the level of proteolytic degradation of these peptides in the broth of the pep4 P. pastoris strain is significantly less than that in the broth of the PEP4 strain (GRF remained>60% intact, even after 4 hr incubation; EGF remained>90% intact, even after 8 hr incubation). These data demonstrate that disruption of the PEP4 gene of P. pastoris results in a substantial reduction of the proteolytic activity in the broth of the strain.

Example V

Isolation of the P. pastoris URA3 Gene

The P. pastoris URA3 gene was identified in a plasmid (YEp13)-based Pichia genomic library by its ability to complement the pyrF mutation (corresponding to a defect in the orotidine monophosphate decarboxylase activity) in E. coli strain CSH-28. The P. pastoris URA3 gene was cloned by isolating colonies of E. coli strain CSH-28 that had been transformed with library DNA and were capable of growth on media lacking uracil.

A. P. pastoris YEp13 Genomic DNA Library

Plasmid YEp13 [Broach et al., Gene 8: 121–133 (1979)] is a convenient shuttle vector that contains an origin of replication for both S. cerevisiae (2µ replicon) and E. coli (pBR ori). In addition, YEp13 contains the Amp$^R$ (ampicillin resistance) gene for use as a selectable marker for transformation of E. coli and the LEU2 gene (a leucine biosynthetic pathway gene) for use as a selectable marker in S. cerevisiae. A P. pastoris (strain NRRL Y-11430) genomic DNA library has been prepared using plasmid YEp13, as described by Cregg et al. [Mol. Cell. Biol. 5: 3376–3385 (1985)].

B. Screening of the P. pastoris YEp13 Genomic DNA Library for the URA3 Gene

The pyrF E. coli strain CSH-28 [see Miller, J. H., in Experiments in Molecular Genetics, Cold Spring Harbor Laboratory Press, Cold Spring Harbor, N.Y. (1972)] is defective for orotidine-5'-phosphate decarboxylase activity and requires uracil when grown on defined medium. It has been demonstrated that the S. cervisiae URA3 gene can complement the pyrF mutation in E. coli [Rose, M., Grisafi, P. and Botstein, D. Gene 29:113–124 (1984)]. Therefore, E. coli strain CSH-28 was transformed with DNA from the P. pastoris YEp13 genomic DNA library in order to screen the library for the P. pastoris URA3 gene capable of complementing the pyrF mutation of the strain.

Transformed CSH-28 cells were plated onto a semi-defined medium which did not contain uracil. Untransformed cells would not grow on this medium. CSH-28 transformants (transformed with P. pastoris genomic library DNA) capable of growing on plates lacking uracil arose at a frequency of ~10/µg of transforming DNA. Plasmid DNA was isolated from 10 of the transformants that did not require uracil for growth. These plasmids were used to transform E. coli strain CSH-28, and 10 out of 10 plasmids complemented the uracil auxotrophy of this strain at high frequency. One of the selected transformants generated by transformation of CSH-28 with P. pastoris genomic library DNA harbored a 9.0 kb insert that contained a 6.6 kb SphI fragment. The 6.6 kb SphI fragment was subcloned into the SphI site of pUC19 for further analysis.

Plasmid DNA from this transformant was digested with SphI and subjected to electrophoresis on a 0.6% agarose gel. The 6.6 kb fragment was isolated using DE81 paper and was eluted from the paper with 400 µl of 1M NaCl. DNA was extracted with 400 µl of phenol/chloroform and precipitated with ethanol. The 6.6 kb fragment was then ligated with 10 ng of alkaline phosphatase-treated, SphI-digested pUC19. The ligation mixture was used to transform E. coli MC1061 cells. Ampicillin-resistant transformants were screened by analysis of restriction enzyme-digested colony DNA for the presence of a 6.6 kb SphI fragment. The correct plasmid was called pPU201. Plasmid pPU201 was used to transform CSH-28 and was able to complement the uracil auxotrophy of this strain.

C. Characterization of the Insert in Plasmid pPU201

Figure 5:
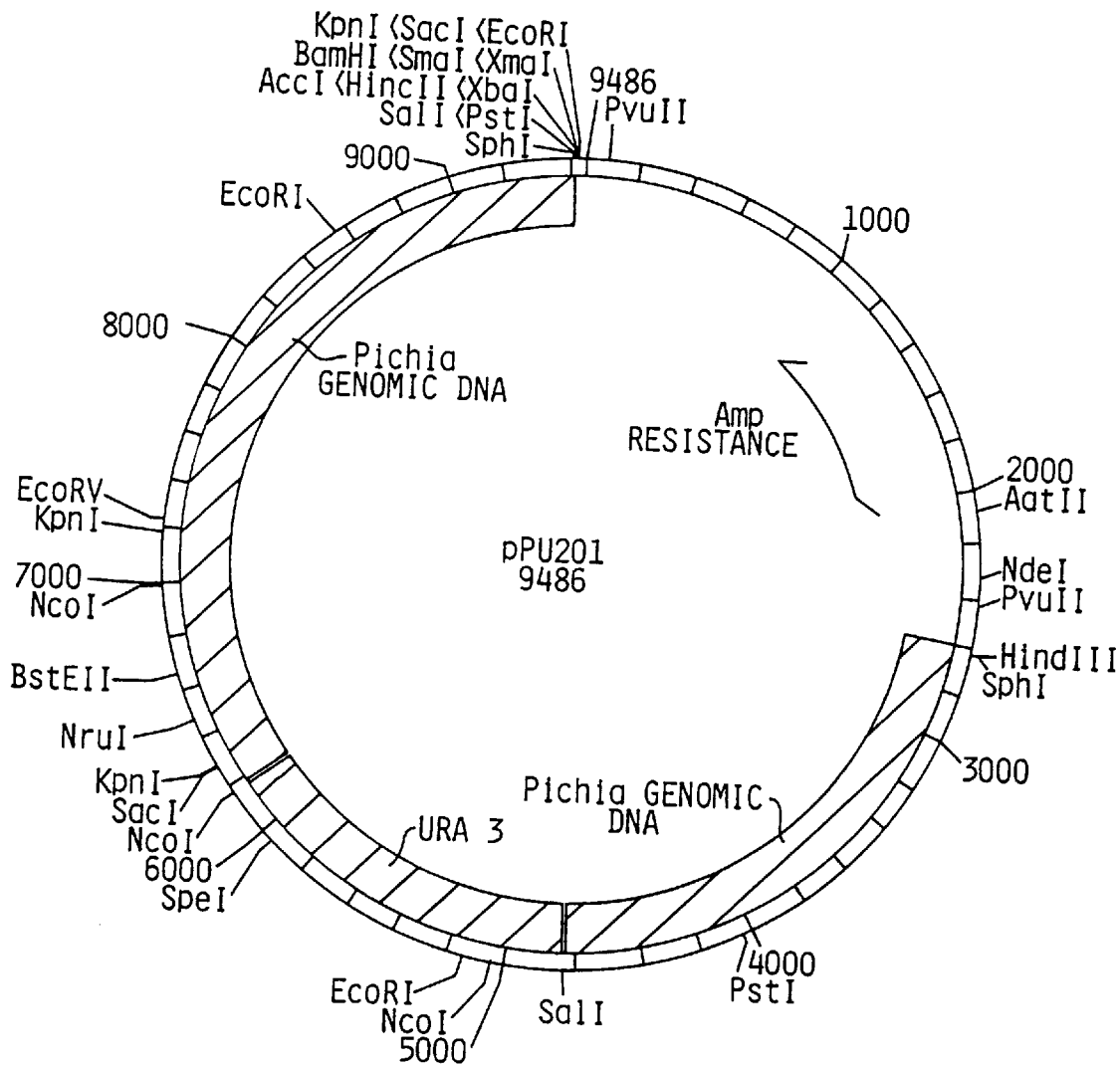
FIG. 5 is a restriction map of plasmid pPU201.

A map of the restriction enzyme recognition sites of the 6.6 kb insert of P. pastoris DNA in plasmid pPU201 (FIG. 5) was prepared by digesting pPU201 with a variety of enzymes and analyzing the resulting fragments using a DNA length computer program (MapSort; University of Wisconsin Genetics, Madison, Wis.) to determine the approximate sizes of the fragments. In order to delineate the URA3 gene contained in the 6.6 kb insert of pPU201, a 5 ng aliquot of each restriction enzyme digest of pPU201 was separated by electrophoresis on a 1% agarose gel, transferred to nitrocellulose, and probed with a radiolabeled 1.3 kb BqlII fragment of the C. tropicalis URA3A gene (see PCT Publication No. WO 90/09449). The filters were hybridized to the probe at 27° C. using a solution containing 25% formamide, 6× SSC, 5× Denhardt's solution, 20 mM Tris.HCl, pH 8.0, 1 mM EDTA, 0.1% sodium dodecyl sulfate (SDS) and 100 µg/ml salmon sperm DNA. After hybridization, the filters were washed three times at room temperature using 1× SSC and 1% SDS for 5–10 minutes per wash, and then washed twice with 0.5× SSC and 0.5% SDS at 45° C. for 10 minutes per wash. These low stringency conditions permitted hybridization between divergent URA3 gene sequences. Additional samples of each digest of pPU201 were separated on an identical 1% agarose gel and stained with ethidium bromide for comparison of hybridizing and non-hybridizing fragments. Comparison of the hybridizing fragments and the restriction map of pPU201 made it possible to localize the URA3 gene in pPU201 to the approximately 1.3 kb NcoI-SalI fragment as shown in FIG. 5. With this knowledge, it was then possible to construct subclones suitable for sequencing and further characterization of the P. pastoris URA3 gene.

Figure 6:
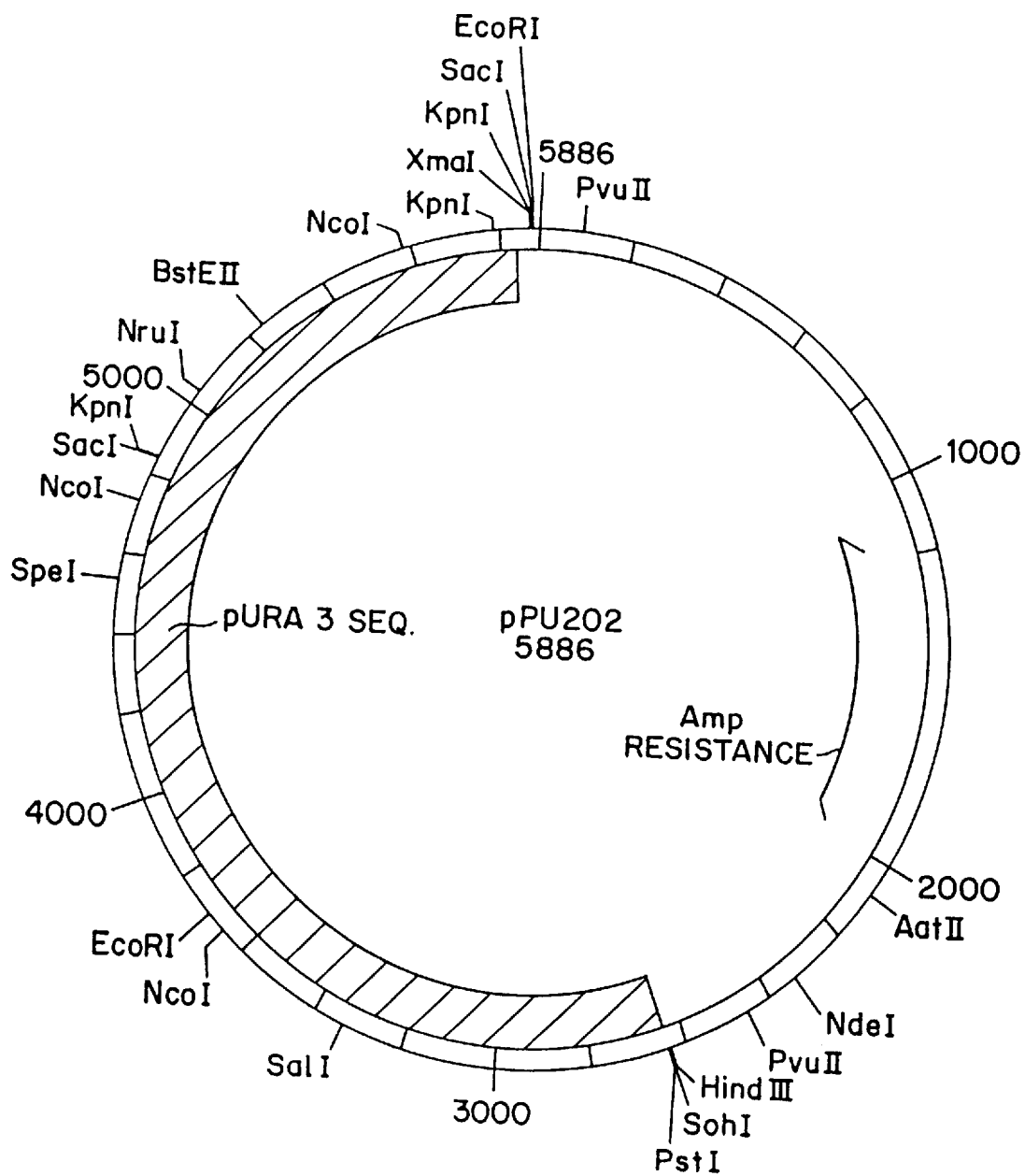
FIG. 6 is a restriction map of plasmid pPU202.
Figure 8:
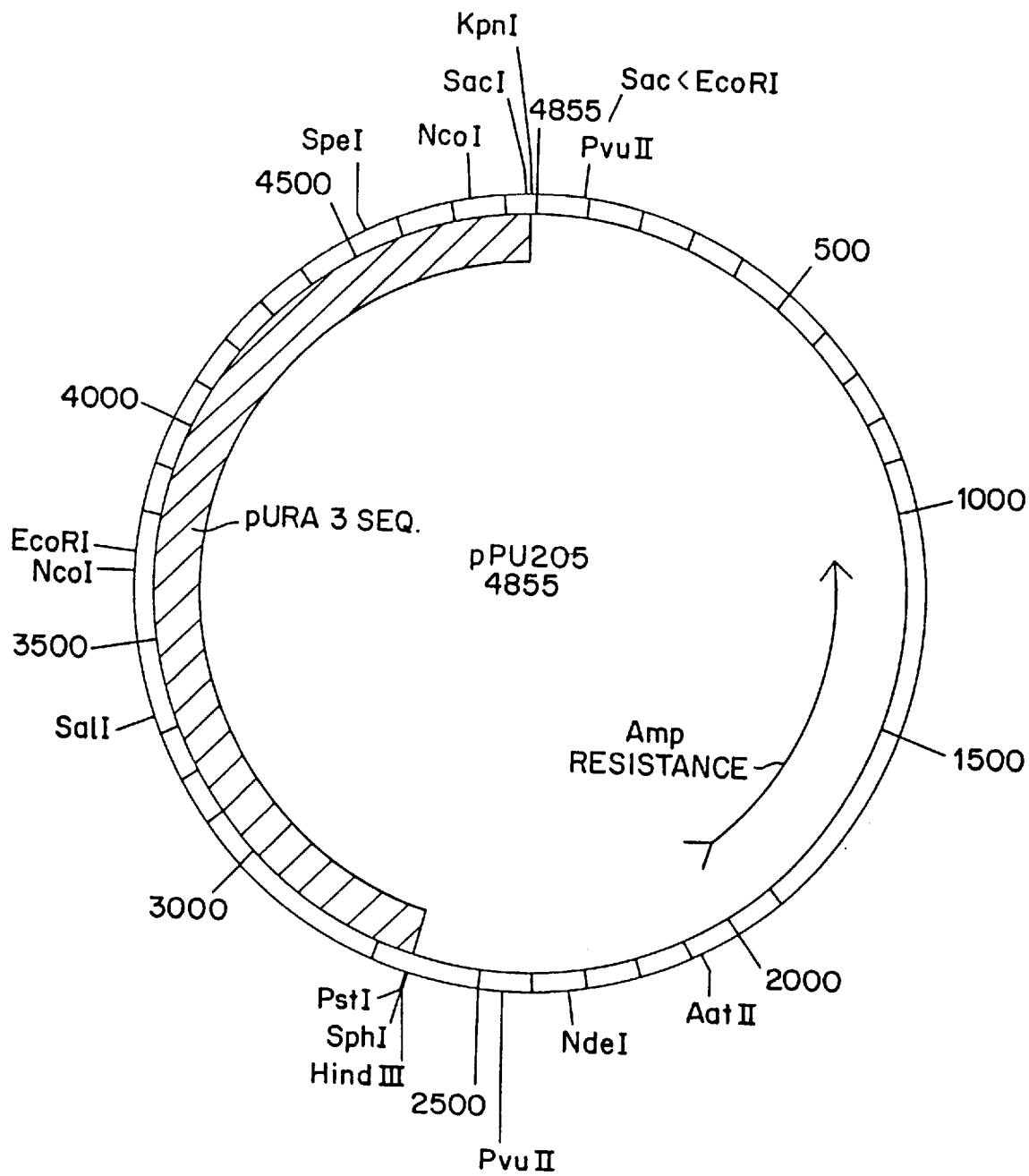
FIG. 8 is a restriction map of plasmid pPU205.
Figure 9:
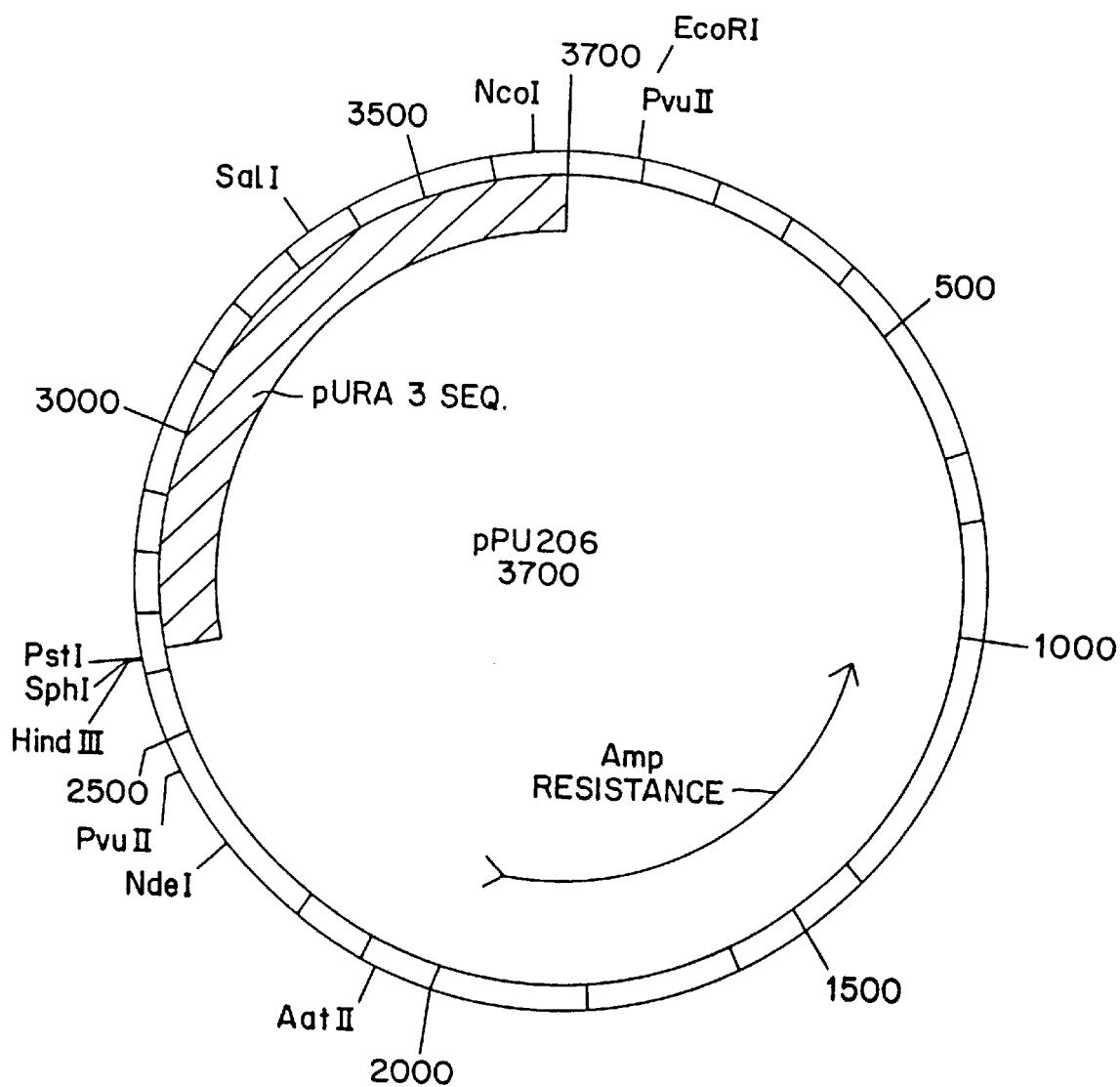
FIG. 9 is a restriction map of plasmid pPU206.

Plasmid pPU202 (FIG. 6) was constructed by digesting pPU201 with EcoRV and PstI, isolating the approximately 4.0 kb fragment containing the URA3 gene, and ligating it into pUC19 at the SmaI and PstI sites. Plasmids pPU203, pPU205 and pPU206 (FIGS. 7–9) were constructed by digesting pPU202 with SacI, KpnI and EcoRI, respectively, and then relegating in a large volume (200 μl). Because there is a recognition site for each of these enzymes in the cloned P. pastoris genomic insert DNA fragment as well as the pUC19 polylinker of pPU202, this strategy allowed for the convenient removal of DNA between these sites in pPU202. The resulting plasmids were then used to transform E. coli strain CSH-28 to determine whether or not each deletion construct could complement the pyrF mutation. The results indicated that pPU203 and pPU205, but not pPU206, contained a functional URA3 gene allowing growth of the PyrF strain on defined medium lacking uracil. These findings are consistent with the mapped position of the P. pastoris URA3 gene in pPU201.

The subclones of the P. pastoris genomic DNA fragment carrying the putative URA3 gene were sequenced using the Sanger dideoxy method [see Sanger et al., Proc. Natl. Acad. Sci. USA 74: 5463–5467 (1977)]. The sequence for the structural gene and approximately 100 bp of flanking sequence was determined in both directions and is presented in Sequence ID No. 3. The amino acid sequence deduced from the cloned P. pastoris URA3 gene (see Sequence ID No. 4) has 73% homology with the amino acid sequence deduced from the S. cerevisiae URA3 gene, 71% homology with the amino acid sequence deduced from the URA3A and URA3B genes of C. tropicalis and 72% homology with the amino acid sequence deduced from the URA3 gene of Kleuveromyces lactis.

Example VI

Development of IGF-1-expressing PEP4-deficient (Pep4$^-$) Strains of Pichia

A. Generation of IGF-1-Expressing Pep4$^-$ Strains by Gene Addition

1. Construction of the P. pastoris PEP4 gene disruption vector RDR421

Plasmid pDR421 was constructed for use in the development of PEP4-deficient (Pep4$^-$) strains of Pichia Rastoris by disruption of a host PEP4 gene through addition of an incomplete PEP4 gene to the endogenous PEP4 locus. This vector contains an internal portion of the PEP4 gene, which, when used to transform PEP4 strains of P. pastoris, integrates into the host genome at the PEP4 locus to generate two incomplete and nonfunctional copies of the PEP4 gene.

Figure 10:
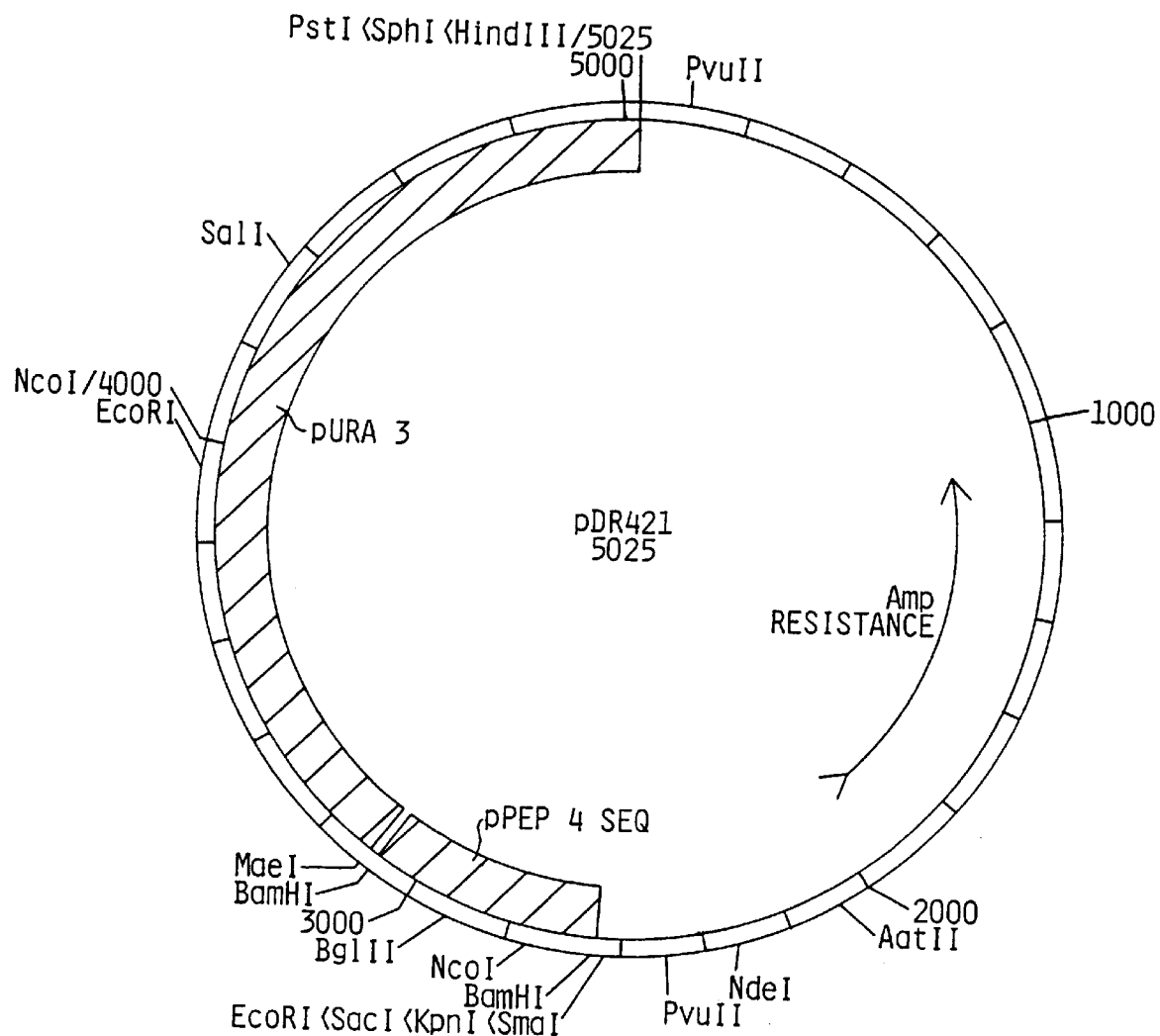
FIG. 10 is a restriction map of plasmid pDR421.

In order to generate the disruption vector pDR421, the URA3 gene of Pichia was cloned into vector pEP205 (consisting of pUC19 sequences and the portion of the PEP4 gene contained in the ~450 bp BamHI fragment derived from pEP202). This was achieved by subcloning the URA3 gene from pPU205 (see FIG. 8) as a 2 kb SpeI-SphI DNA fragment into the XbaI-SphI sites of pEP205 (see FIG. 2) as follows:

Plasmid pPU205 was digested with SpeI and SphI and the reaction mixture was separated on a 0.8% agarose gel. The 2 kb DNA fragment containing the URA3 gene was isolated from the gel using DE81 paper, eluted and purified. Plasmid pEP205 was digested with XbaI and SphI. The 2 kb URA3 gene-containing SpeI-SphI fragment isolated from pPU205 was ligated to XbaI/SphI-digested pEP205 and the mixture was used to transform E. coli strain MC1061 to ampicillin resistance. Ampicillin-resistant colonies were screened by analysis of BamHI/SphI restriction enzyme-digested colony DNA for the presence of 2.7 kb, 0.4 kb and 1.9 kb diagnostic fragments. A transformant was found to harbor a plasmid with the correct DNA construct called pDR421 (FIG. 10).

2. Transformation of an IGF-1-expressing ura3 P. pastoris strain (IGF-U) with RDR421

The ura3 IGF-1-expressing strain of P. pastoris, IGF-U, was transformed with pDR421 to generate Pep4$^-$, IFG-1-expressing strains of P. pastoris.

a. Generation of IGF-U

5-Fluorotic acid (5-FOA) is an analog of a uracil biosynthetic pathway intermediate that, when metabolized by Ura$^+$ strains, yields a toxic compound. Because the uracil biosynthetic pathway of Ura$^-$ strains is blocked at certain steps, these strains do not metabolize 5-FOA (to produce a compound toxic to the cells) and are therefore unaffected by its toxic effects (i.e., the strains are 5-FOA resistant). In contrast, Ura$^+$ strains metabolize 5-FOA and cannot survive on 5-FOA-containing medium. Therefore, plating cells on 5-FOA-containing medium can be used as a method to generate Ura$^-$ strains by spontaneous mutation [see, for example, Boeke et al., Mol. Gen. Genet. 197: 345–346 (1984)].

A Ura3$^-$ derivative of the IFG-1-producing strain G+IMB206S1 [see U.S. application Ser. No. 578,728] was generated by direct plating of ~5×10$^7$ cells of strain G+IMB206S1 into 5-FOA-containing medium supplemented with uracil (0.67% yeast nitrogen base, 2% agar, 2% glucose, 750 mg/l of 5-FOA and 48 mg/l of uracil). After one week of incubation at 30° C., a colony growing on the plate was isolated. This colony, which required uracil in order to grow, was unable to complement a ura3 strain of Pichia pastoris. This strain was named IGF-U.

b. Transformation of IGF-U

Approximately 20 μg of pDR421 was digested with BglII. This DNA was then used to transform IGF-U using the standard spheroplast transformation procedure. Transformants were selected by their ability to grow in the absence of uracil over a 6 day period.

3. Characterization of transformants a. Analysis of transformant carboxypeptidase Y activities Ura$^+$ transformants were subsequently analyzed for carboxypeptidase Y activity using a colony overlay colorimetric screening procedure, as described in Example II. Colonies of Ura$^+$ transformants that appeared to have low carboxypeptidase Y activities based on the results of this assay (i.e., colonies that failed to develop a strong red color indicative of Pep4$^+$ colonies) were isolated, transferred to a master place, subcultured along with control colonies and rescreened using the overlay assay. One colony which again failed to develop a strong red color was called M+IMB206S1.

b. Analysis of intact IGF-1 expression levels of an IGF-1-expressing pep4 strain of P. pastoris grown in one- and ten-liter fermentations i. Fermentation of an IGF-1-expressing pep4 strain of *P. pastoris*

An IFG-1-expressing pep4 strain of *P. pastoris*, M+IMB206S1, generated as described in Example VI.A.2.b., was grown in one- and ten-liter fermentations according to a three-phase protocol consisting of a glycerol batch growth phase, a limited glycerol fed-batch phase and a methanol fed-batch phase. In order to compare the intact IGF-1 expression levels of pep4 and PEP4 IFG-1-expressing strains of *P. pastoris*, two PEP4 strains of *P. pastoris*, G+IMB204S14 and G+IMB206S1, containing four and six copies of an IGF-1 gene expression cassette, respectively (see commonly assigned U.S. patent application Ser. No. 578,728, filed Sep. 4, 1990, for a description of this strain; the above-cited application is hereby incorporated by reference herein in its entirety), were also grown in comparable fermentations as follows.

One-liter fermentation protocol

A two-liter fermentor (Biolafitte, Princeton, N.J.) was autoclaved with 900 ml of minimal salts medium (21 ml 85% phosphoric acid, 0.9 g calcium sulfate, $2H_2O$, 14.3 g potassium sulfate, 11.7 g magnesium sulfate, and 3.2 g potassium hydroxide) and 30 g of glycerol. After sterilization, 4 ml $PTM_1$ trace salts solution (6 g/l cupric sulfate.$5H_2O$, 0.08 g/l sodium iodide, 3 g/l manganese sulfate.$H_2O$, 0.2 g/l sodium molybdate.$2H_2O$, 0.02 g/l boric acid, 0.5 g/l cobalt chloride, 20 g/l zinc chloride, 65 g/l ferrous sulfate.$H_2O$, 0.2 g/l biotin and 5 ml sulfuric acid) were added to the fermentor and the pH was adjusted to 5 with concentrated $NH_4OH$. The pH was controlled by addition of 50% $NH_4OH$ containing 0.1% Struktol J673 antifoam (added to control foaming). The temperature was maintained at 30° C., and dissolved oxygen was maintained above 20% of saturation by increasing agitation, aeration, or the supplementation of the air feed with oxygen.

Inocula were prepared from cells grown overnight at 308° C. in buffered YNB containing 2% glycerol. The fermentor was inoculated with 40–70 ml of the cultured cells which had grown to an $OD_{600}$ of 2–8, and the batch growth regimen was continued for 18–24 hours until glycerol was exhausted. At the point of glycerol exhaustion, indicated by an increase in dissolved oxygen concentration, a glycerol feed (50% w/v glycerol plus 12 ml/L $PTM_1$) was initiated at 10 ml/hr. In pH 5.0 fermentations, the pH of the culture was maintained at 5 throughout the fermentation. In low pH fermentations (i.e., pH 2.8 or pH 3.5), the set point of the pH controller was adjusted to the desired pH after initiation of the glycerol feed. After four hours, the pH of the culture decreased to the set point value as a result of cellular metabolism. This lower pH was then maintained throughout the remainder of the fermentation. The glycerol feed was then terminated and a methanol feed (100% methanol plus 12 ml/L $PTM_1$) was initiated at a rate of 2 ml/hr. After three hours of methanol feeding, the feed rate was increased to 6 ml/hr and maintained at this rate for the remainder of the fermentation. The vessel was harvested 72 hours after initiation of the methanol feed.

The fermentation was monitored in terms of $NH_4OH$, antifoam, glycerol, methanol, ethanol, and wet cell weight levels as described in Example III. Broth and cell samples were collected throughout the fermentation as also described in Example III.

Ten-liter fermentation protocol

A 15-liter fermentor containing 3.5 liters of 10X basal salts (42 ml 85% phosphoric acid/l, 1.8 g calcium sulfate.$2H_2O$/l, 28.6 g potassium sulfate/l, 23.4 g magnesium sulfate/l, 6.5 g potassium hydroxide/l) and 220 g glycerol in a total volume of 5.5 liters was sterilized. After the fermentor had cooled, 24 ml $PTM_1$ trace salts were added and the pH was adjusted to 5.0 with the addition of 28% ammonium hydroxide. The pH was controlled by the addition of the same solution. Foaming was controlled with the addition of a 5% solution of Struktol J673. Temperature was maintained at 30° C., and dissolved oxygen was maintained above 20% of saturation by increasing agitation, aeration, reactor pressure or by supplementation of the air feed with oxygen. Inocula were prepared from *P. pastoris* cells grown overnight in buffered yeast nitrogen base (YNB; 11.5 g/L $KH_2PO4$, 2.66 g/L $K_2HPO_4$, 6.7 g/L yeast nitrogen base, pH 6) containing 2% glycerol. The fermentor was inoculated with 500–700 ml of the cultured cells which had grown to an $OD_{600}$ of 2–8, and the batch growth regime was continued for 18–24 hours. At the point of glycerol exhaustion, indicated by an increase in dissolved oxygen concentration, a glycerol feed (50% w/v glycerol plus 12 ml/L $PTM_1$) was initiated at 100 ml/hour and continued for 4 hours. The glycerol feed was then terminated and a methanol feed (100% methanol plus 12 ml/L $PTM_1$) was initiated at 20 ml/hr. With the initiation of the methanol feed, the set point of the pH controller was adjusted to 2.8. The pH then gradually decreased to the set point value as a result of cellular metabolism. After 4 hours of methanol feeding, the methanol feed rate was increased to 60 ml/hour and maintained at this rate for a total of approximately 72 hours, at which point the vessel was harvested.

ii. IGF-1 expression levels of pep4 and PEP4 IGF-1-expressing strains

One of the several forms of IGF-1 produced in fermentations of recombinant IFG-1-secreting strains of *P. pastoris* is a nicked species consisting of two or more fragments of the IGF-1 molecule held together by disulfide bonds. The fragments are generated by proteolytic cleavage of one or more peptide bonds of the amino acid backbone of the IGF-1 molecule. Although nicked and intact IGF-1 molecules are indistinguishable on the basis of apparent molecular weight [under non-reducing conditions, as determined by SDS-polyacrylamide gel electrophoresis (SDS-PAGE)], these species can be resolved by reverse phase HPLC under non-reducing conditions and by SDS-PAGE under reducing conditions (i.e., in the presence of a reducing agent such as dithiothreitol). Reduction of the disulfide bonds holding the fragments of nicked IGF-1 together results in liberation of the individual proteolytically generated IGF-1 fragments which have smaller molecular weights than the intact molecule.

Quantitation of IGF-1 expression levels

The yields of nicked and authentic (intact, correctly folded, monomeric) IGF-1 in the cell-free broth were determined by quantitative reverse phase HPLC. The HPLC system that was used was the same as that described in Example IV, except a Vydac C4 column (0.46×5 cm) was employed instead of a C18 column. A 1%/minute gradient of 25–42% mobile phase B was passed through the column during a period of 17 minutes at a flow rate of 1 ml/minute to elute samples from the column. The detector was set at 0.05 absorbance units full scale (AUFS), and a wavelength of 215 nm was used for maximum sensitivity.

To distinguish the authentic and nicked IGF-1 species in *P. pastoris* broth by HPLC, it was necessary to clean-up the broth by removing some endogenous *P. pastoris* contaminants from the broth prior to loading broth samples onto the HPLC column. This was accomplished by passing the broth through a sulphopropyl-based cation exchange resin contained in a 0.25 ml column. The resin was first washed with 2 ml of 0.2M acetic acid, then equilibrated with 2 ml of 0.02M acetic acid. A volume of crude cell-free broth (1 ml) was loaded onto the column which was then washed with 1 ml of 0.02M acetic acid. The IGF-1 was eluted with 2 ml of 0.02M sodium acetate, pH 5.5, plus 1M NaCl. The first 1 ml of eluate contained 75–80% of the total IGF-1 and was usually the only elution volume collected. The column was then regenerated by washing with 2 ml of 100% methanol and thereby available for re-use.

In order to quantitate the levels of Pichia-produced IGF-1, known amounts of standard IGF-1 (Amgen, Thousand Oaks, Calif.) were injected into the HPLC column and the area under the corresponding peaks in the chromatograms was measured. A standard curve was generated by plotting area versus μg of IGF-1 loaded onto the HPLC column. A correlation coefficient for use in converting the area under HPLC chromatogram peaks to IGF-1 concentration was calculated from the standard curve. When the detector was set at 0.05 AUFS and a wavelength of 215 nm, the correlation coefficient was 350 units/μg of IGF-1 injected onto the column. Using this information, it was possible to determine the concentration of correctly folded, intact monomeric IGF-1 present in a cleaned-up broth sample by measuring the area under the corresponding peak on the chromatogram from HPLC analysis of the sample. This correlation coefficient was also used to estimate the approximate concentration of the nicked IGF-1 species as well. However, the absolute concentrations of the nicked species may vary depending on differences in the specific correlation coefficients of intact and nicked IGF-1.

Results of one-liter fermentations

One-liter low pH (pH 2.8) fermentations of the pep4 IFG-1-expressing strain consistently yielded greater amounts of total monomeric (authentic plus nicked) IGF-1 (~200–250 mg/l) than one-liter low pH fermentations of the PEP4 IFG-1-expressing strains (~160–190 mg/L). Furthermore, the percentage of authentic IGF-1 in the broth of the pep4 strain was somewhat higher (77%) than that in the broth of the PEP4 strains (65%). However, a much more dramatic difference in the monomeric IGF-1 production levels of the pep4 and PEP4 strains was detected in pH 5.0 fermentations of these strains. Essentially no IGF-1 was detected in one-liter pH 5.0 fermentations of the PEP4 IFG-1-expressing strains G+IMB204S14 and G+IMB206S1. This result indicates that the authentic IGF-1 produced in fermentations of PEP4 strains is subjected to extensive proteolysis at pH 5.0, but to only limited proteolysis at lower pH. In contrast, one-liter pH 5.0 fermentations of the pep4 IGF-1-expressing strain M+IMB206S1 yielded at least 200 mg of monomeric IGF-1/l, approximately 80% of which was authentic IGF-1. The pep4 IFG-1-expressing strain thus appears to be significantly improved relative to the PEP4 IFG-1-expressing strains for production of authentic IGF-1 at pH 5.0 and somewhat improved for production of authentic IGF-1 at pH 2.8.

Results of ten-liter fermentations

Ten-liter fermentations of the Dep4 IGF-1-expressing strain of *P. Pastoris* yielded greater amounts of total monomeric IGF-1 (~200 mg/l) than did ten-liter fermentations of the PEP4 IGF-1-expressing strains (~170 mg/l).

The compositions of the total monomeric IGF-1 produced in 10-liter fermentations of the PEP4 and pep4 strains also differed. Greater than 75% (164 mg/1) of the total monomeric IGF-1 in the 10-liter fermentation of the pep4 strain M+IMB206S1 was authentic IGF-1, whereas only about 50% (88 mg/l) of the total monomeric IGF-1 in the 10-liter fermentation of the PEP4 strain G+IMB204S14 was authentic IGF-1.

Furthermore, because the cell yield in the fermentation of the pep4 strain was ~30% less than the cell yield in the fermentation of the PEP4 strain, the per cell yield of authentic IGF-1 was greatly enhanced in the fermentation of the pep4 strain. As a consequence of lower cell yield in the fermentation of the pep4 strain, a greater volume of cell-free broth was recovered from the fermentation of the pep4 strain (relative to the volume of cell-free broth recovered from the fermentation of the PEP4 strain). This results in the recovery of higher levels of secreted IGF-1 from the fermentation of the pep4 strains (relative to the amount of secreted IGF-1 recovered from the fermentation of the PEP4 strain).

The results presented above demonstrate that the pep4 IFG-1-expressing strain is improved, relative to the PEP4 IFG-1-expressing strain, for production of authentic IGF-1 on a large scale.

B. Generation of an IFG-1-Expressing Pep4⁻ Strain by Gene Replacement

1. Construction of the *P. pastoris* gene disruption vectors pDR601 and pDR602

Figure 11:
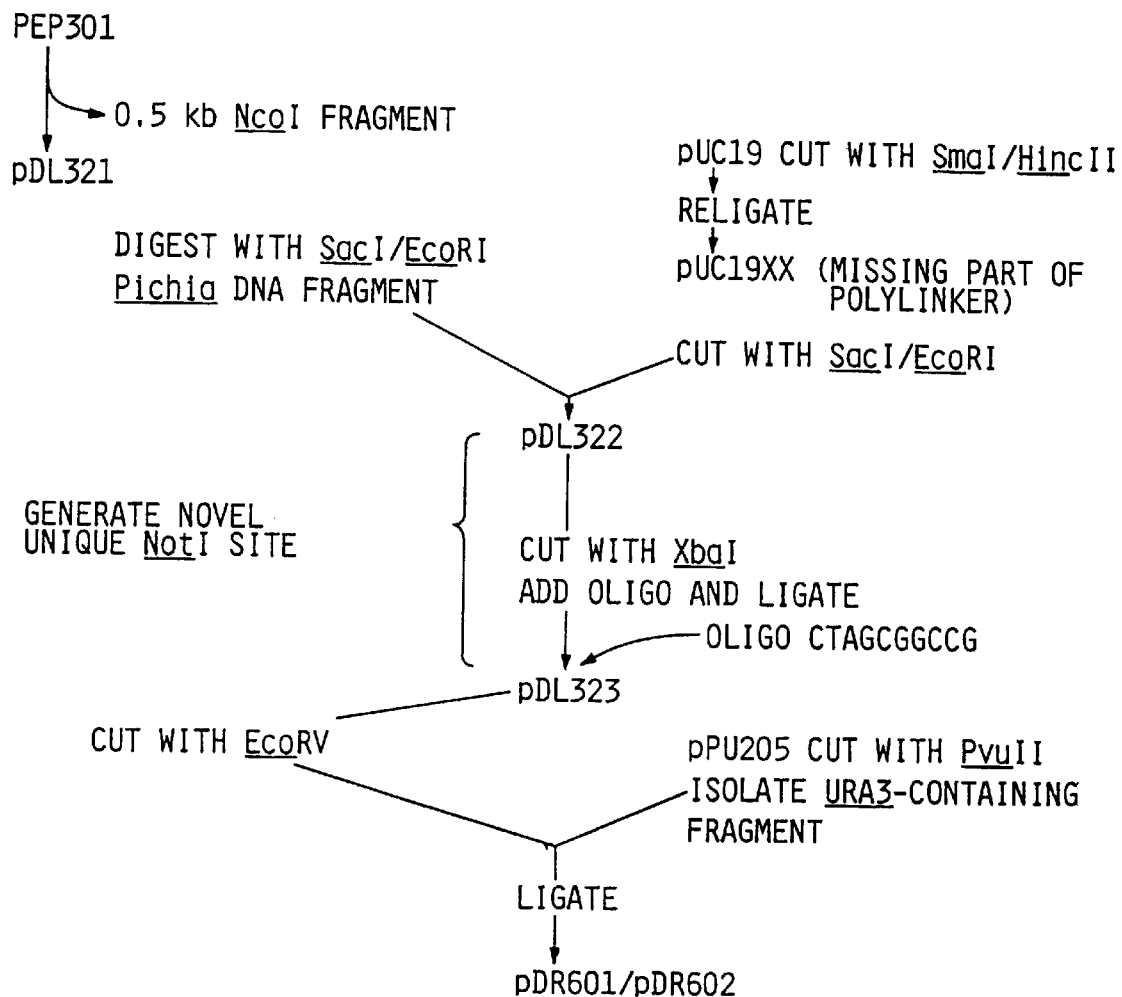
FIG. 11 summarizes the steps employed in the construction of pDR601 and pDR602.

Vectors pDR601 and pDR602 were used in the development of PEP4-deficient (Pep4⁻) strains of *P. pastoris* by disruption of a host PEP4 gene through replacement of the endogenous PEP4 gene with a defective pep4 gene. This vector was constructed in several steps as follows (see also diagram in FIG. 11).

Plasmid pEP301 (see FIG. 3), consisting of pUC19 sequences and the cloned *P. pastoris* PEP4 gene from pEP202, was cleaved with NcoI, and the DNA was then precipitated with ethanol, harvested, resuspended and ligated in ligation reaction mixture. This digestion and ligation effectively removed an internal portion of the PEP4 gene contained in an ~0.5 kb NcoI fragment. After ligation, the DNA was digested with BglII to linearize any remaining parental plasmid, and the DNA was used to transform *E. coli* strain MC1061. Ampicillin-resistant colonies were selected and screened by analysis of restriction enzyme digests of colony DNA for the presence of a 0.5 kb NcoI fragment. The correct plasmid, containing the defective PEP4 gene lacking an ~0.5 kb NcoI fragment, was named pDL321. A second plasmid, pUC19XX, was generated by cleaving pUC19 with SmaI and HincII and relegating, effectively removing a portion of the polylinker containing the BamHI and XbaI sites. Plasmid pUC19XX was then cut with SacI and EcoRI and ~10 ng was ligated with ~50 ng of the SacI/EcoRI 2.2 kb fragment of pDL321, which had been gel-purified and isolated with DE81 paper. The ligation mix was used to transform MC1061 cells, and ampicillin-resistant colonies were screened by analysis of BstEII/XbaI-digested colony DNA. Plasmid showing the correct digest pattern was designated pDL322.

pDL322 was then cut with XbaI and 10 ng were ligated with 10 ng of an oligonucleotide linker of the sequence 5'-CTAGCGGCCG-3', which destroyed the XbaI site and generated a unique NotI site when ligated into the XbaI site. The ligation mix was used to transform MC1061 cells. Ampicillin-resistant colonies were screened by analysis of NotI-digested colony DNA. The correct plasmid was called pDL323.

Figure 13:
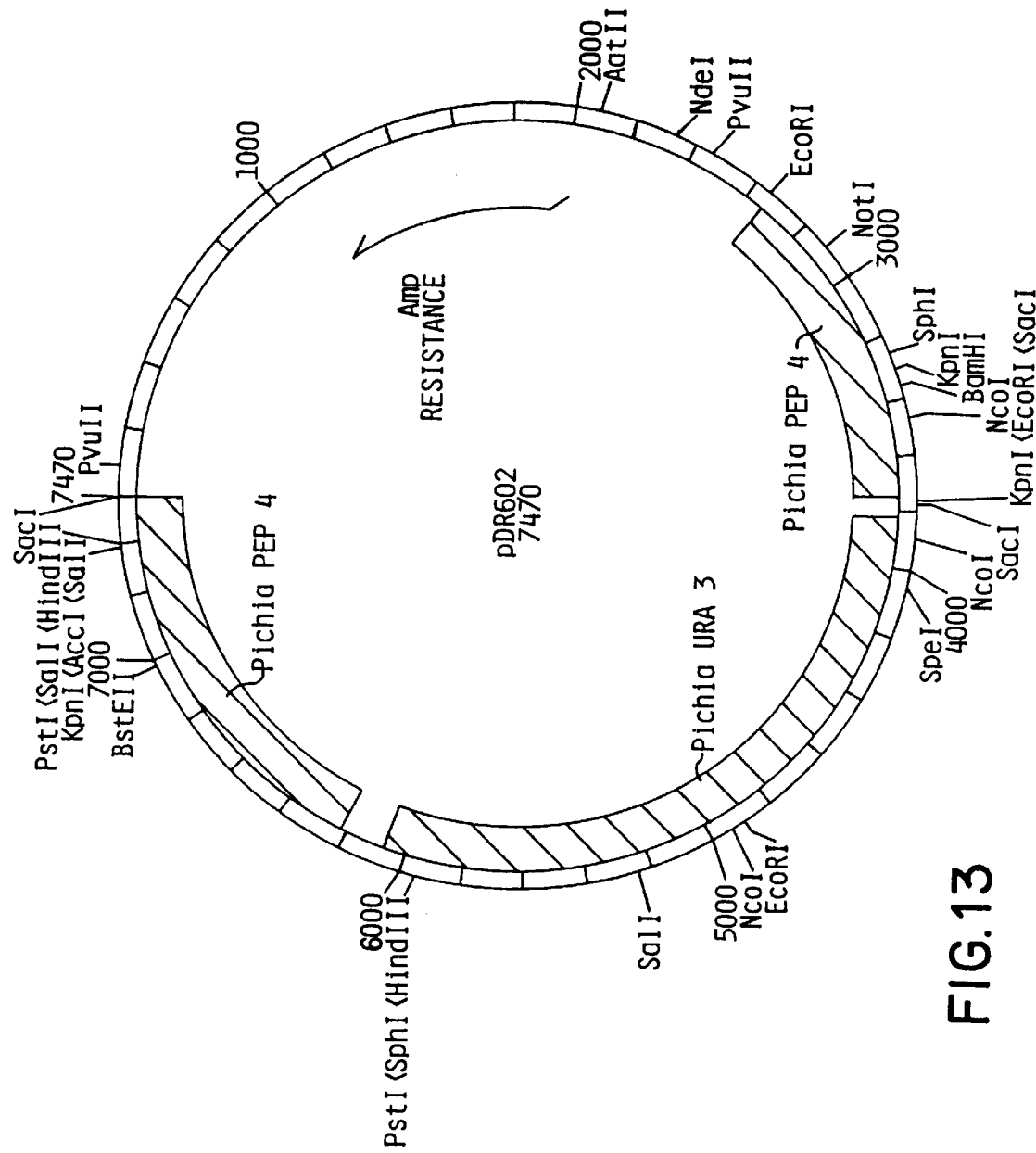
FIG. 13 is a restriction map of plasmid pDR602.

To generate vectors pDR601 and pDR602, the Pichia URA3 gene was inserted into pDL323 as follows. Plasmid pPU205 (see FIG. 8) was digested with PvuII and AatI to liberate the URA3 gene on an approximately 2.5 kb PvuII fragment. The digest was separated on a 0.8% agarose gel. The ~2.5 kb fragment was isolated from the gel using DE81 paper, eluted and purified. pDL323 was linearized by cutting it with EcoRV. This linearized plasmid (~10 ng) was ligated with the URA3-bearing PvuII fragment of pPU205 to generate pDR601 and pDR602 (see FIGS. 12 and 13, respectively), depending upon the orientation of the inserted URA3 gene.

2. Transformation of IGF-U with VDR601 and RDR602

The ura3 IFG-1-expressing *P. pastoris* strain IGF-U (see Example VI.A.2.a.) was transformed with linear fragments of DNA derived from pDR601 and pDR602. The linear fragments contained the URA3 gene flanked on each side with DNA coding for a portion of the PEP4 gene. Homology between the ends of the fragments and the PEP4 gene stimulated integration of the fragments at the PEP4 locus resulting in a gene replacement event. Stable integration of either fragment into the host genome yielded prototrophic transformants due to the stable presence of the URA3 gene contained in the fragments. The transformation was conducted as follows:

Linear DNA fragments (~4.0 kb in length), consisting of the URA3 gene flanked on each side with DNA coding for a portion of the PEP4 gene, were obtained by digesting both pDR601 and pDR602 with NotI and BstEII. The digested DNA (20 μg) was used to transform strain IGF-U using the standard spheroplast procedure. Ura$^+$ colonies isolated from transformants growing on regeneration medium and subcultured onto YEPD medium were screened for carboxypeptidase Y activity using the overlay procedure described in Example II. Colonies that did not develop a red color relative to control colonies were selected for analysis by Southern blot hybridization.

3. Southern blot hybridization of transformant DNA

Genomic DNA was isolated from the selected transformants using the method of Hoffman and Winston [Gene 57: 267–272 (1987)]. Genomic DNA from each strain was digested with BstEII. This procedure liberates a portion of the PEP4 locus containing the region of integration of fragments of pDR601 or pDR602. Therefore, the size of this region is diagnostic for correct integration of the transforming DNA into the genome of IGF-U. The digested DNA was subjected to electrophoresis on a 0.8% agarose gel and blotted to a nitrocellulose filter. The filter was hybridized with a radiolabeled 1.4 kb XbaI/EcoRV fragment of pEP301 which contains part of the *P. pastoris* PEP4 gene using standard procedures [Maniatis, T., Fritsch, E. F. and Sambrook, J. *Molecular Cloning, A Laboratory Manual*, pp 385–388, Cold Spring Harbor Laboratory Press, Cold Spring Harbor, N.Y., USA. (1982)]. Hybridization was conducted at 37° C. in a solution containing 50% formamide, 6× SSC, 5× Denhardt's solution, 20 mM Tris HCl, pH 8.0, 1 mM EDTA, 0.1% SDS and 100 μg/ml salmon sperm DNA. The filter was then washed three times in 1× SSC, 0.1% SDS (10 min per wash) and then in 0.5× SSC, 0.1% SDS at 65° C. for 1 hr. As a comparative control, genomic DNA from *P. pastoris* strain GS115, a PEP4 strain, was included in this analysis.

Digestion of genomic DNA from GS115 with BstEII yielded a 4.4 kb fragment that hybridized to the portion of the PEP4 gene contained in the probe. In contrast, this probe hybridized to a 6.9 kb fragment in DNA from at least two of the transformants, IGFU2601-5 and IGFU2602-5. The larger size of the transformant PEP4 locus as compared to the control PEP4 locus (6.9 vs. 4.4 kb) is consistent with replacement of the host PEP4 gene with a nonfunctional pep4 gene carrying the URA3 gene within its structural region.

From these results, it was concluded that strains IGFU2601-5 and IGFU2602-5 were examples of the several pep4 strains generated by disruption of the PEP4 gene of host strain IGF-U through gene replacement.

Example VII

Generation of a pep4$^-$ Pichia Strain Using "Popout" Vectors

The pop-in-pop-out gene disruption technology is based on the addition of a DNA fragment containing a defective gene to the genome of a host organism, with subsequent removal of portions of the DNA fragment and endogenous sequences from the host through homologous recombination between the endogenous target gene sequence and the integrated vector sequence. Initially, transformants are selected for incorporation of the disruption vector which contains a marker gene such as URA3 (i.e., the "pop-in" step). Next, the selected transformants must be screened to identify strains in which a recombination event between endogenous gene sequences and integrated vector sequences has occurred thereby excising portions of the vector, including the marker gene, and endogenous sequences of the host (i.e., the "pop-out" step). An innovative double selection system based on the URA3 gene and Ura3$^-$ hosts enables the sequential identification of the desired strains.

This type of gene disruption is typically conducted in Ura$^-$ strains. Ura$^-$ strains are easily identified by resistance to 5-fluoroorotic acid (5-FOA). Disruption vectors contain a defective copy of the target gene to be disrupted and a functional URA3 gene. Integration of the disruption vector into the genome of the Ura$^-$ host cells generates Ura$^+$ transformants containing one functional target gene and one non-functional (i.e., defective) target gene. Ura$^+$ transformants are easily identified by their ability to grow in the absence of uracil.

In order to isolate strains in which a recombination event has resulted in the elimination of the functional target gene, leaving only a defective gene, the Ura$^+$ transformants are screened for restoration of 5-FOA resistance resulting from the loss ("pop-out") of the URA3 gene which accompanies recombination. The regeneration of the ura3 genotype enables repetition of the "pop-in-pop-out" process for the subsequent disruption of other genes in the genome.

1. Construction of *P. pastoris* gene disruption vector pDL521

Figure 14:
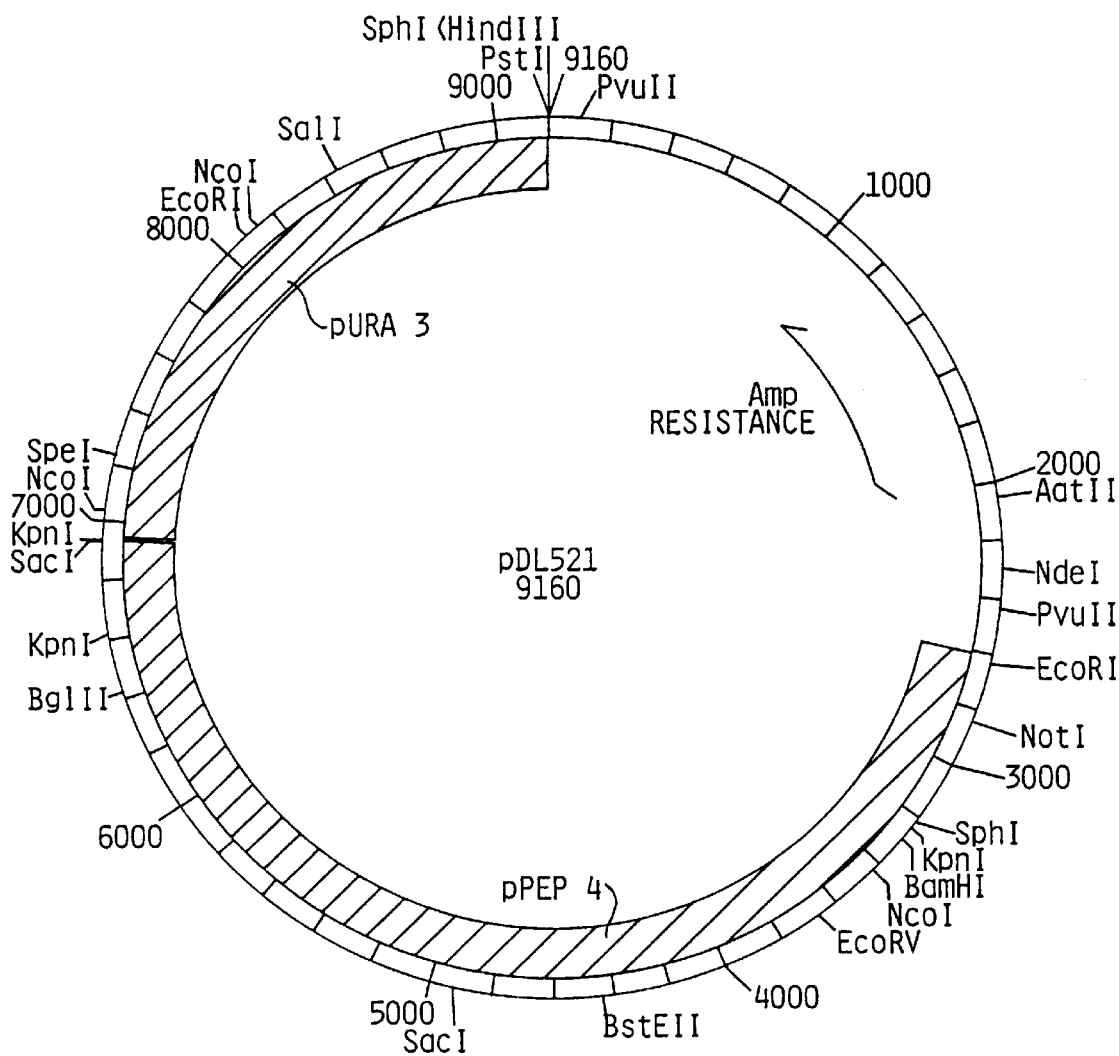
FIG. 14 is a restriction map of plasmid pDL521.
Figure 15:
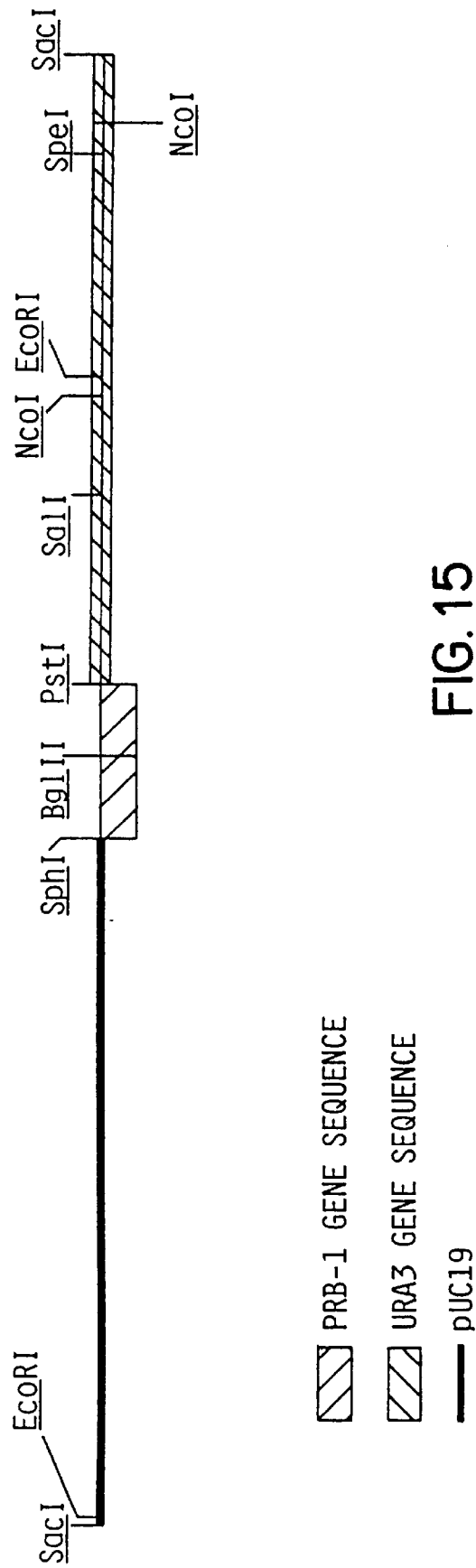
FIG. 15 is a restriction map of plasmid pDR911.

Vector pDL521 was used in the development of PEP4-deficient (Pep4$^-$) strains of *P. pastoris* by disruption of a host PEP4 gene through "pop-in/pop-out" methods. In this method, a defective pep4 gene containing a small deletion is added to a host PEP4 locus, and a functional PEP4 gene is removed from the PEP4 locus (i.e., pop-in/pop-out).

pDL521 was constructed in two steps. First, an intermediate plasmid, pDL501, was constructed by ligation of the 2.2 kb EcoRI/SacI fragment of pDL323, the 2.2 kb SacI/PstI fragment of pPU205 and the 2.7 kb EcoRI/PstI fragment of pUC19 in a three-way ligation. These three fragments were obtained as follows. pPU205, which contains the *P. pastoris* URA3 gene (FIG. 8), was digested with PstI and SacI. A 2.2 kb PstI-SacI fragment containing the URA3 gene was gel isolated and purified using DE81 paper. Plasmid pDL323, harboring a defective pep4 gene which lacks a 0.5 kb NcoI fragment present in an intact PEP4 gene (see FIG. 11), was digested with EcoRI and SacI. A 2.2 kb fragment containing the defective pep4 gene was gel isolated and purified using DE81 paper. pUC19 was digested with EcoRI and PstI. The three fragments (0.02 μg of the EcoRI/PstI-digested pUC19, 0.02 μg of the 2.2 kb PstI/SacI fragment of pPU205 and 0.02 μg of the 2.2 kb EcoRI/SacI fragment of pDL323) were ligated in a three-way ligation. The ligation mix was used to transform *E. coli* strain MC1061. Ampicillin-resistant colonies were screened by analysis of NcoI-digested colony DNA. Plasmid containing the correctly ligated fragments was called pDL501. pDL501 was then cut with SacI, treated with calf alkaline phosphatase and 0.02 μg were ligated with 0.02 μg of a 1.9 kb SacI fragment isolated from SacI-digested pEP202 and purified using DE81 paper. This added more PEP4 flanking sequence to the 3' end of the defective pep4 gene in pDL501 and ensured a greater amount of homologous sequence for recombination with the endogenous PEP4 gene during transformation of P. pastoris host IGF-U. The ligation mix was used to transform E. coli strain MC1061. DNA from ampicillin-resistant colonies was digested with BglII and SpeI and screened for the presence of the diagnostic 0.8 kb fragment indicative of the presence of the added SacI fragment from pEP202. Correct plasmid was called pDL521 (see FIG. 14).

2. Transformation of GS4-2 with pDL521 a. Generation of GS4-2

A ura3 strain of P. pastoris was required as a host in the generation of a pep4 strain by the pop-out process. A ura3 strain was developed by direct plating of $10^6$ cells of the general his4 P. pastoris host strain GS115 in 5-fluoroorotic acid medium supplemented with uracil (0.67% yeast nitrogen base, 2% agar, 2% glucose, 750 ng 5-FOA/l and 48 mg uracil/l). After one week of incubation at 30° C., a colony growing on the plate was isolated. This His$^-$Ura$^-$ strain was named GS4-2.

b. Transformation of GB4-2 and generation of a Pep4$^-$ strain pDL521 was linearized by digestion with NotI. The NotI site is located immediately 5' of the site at which sequence had been deleted from the PEP4 gene to make it defective. The ends of the NotI fragment are homologous to sequences in the endogenous PEP4 gene of GS4-2, which promotes integration of the fragment by homologous recombination at the PEP4 locus.

The His$^-$ Ura$^-$ strain GS4-2 was transformed according to the spheroplast method with 20 μg of pDL521 which had been linearized by digestion with NotI. Transformants were selected by their ability to grow on media lacking uracil. Twelve of these transformants were picked and colony purified. Genomic DNA was isolated from these transformants (as described in Example VI.B.3.), cut with SalI and subjected to electrophoresis on a 0.8% agarose gel. The DNA was transferred to a nitrocellulose filter and probed with a radiolabeled 1.2 kb EcoRV/XbaI fragment of the PEP4 gene. Two strains, GS4-2521-3 and GS4-2521-4, which appeared to have integrated pDL521 into the PEP4 locus, based on the Southern blot hybridization pattern of genomic DNA, were chosen for further selection. These strains contained the URA3 marker gene with an intact complete PEP4 gene on one side and a defective PEP4 gene (lacking ~0.5 kb of sequence) on the other side of the marker gene. This configuration of the PEP4 locus permits recombination between the two copies of the PEP4 gene that would result in elimination of one of the PEP4 genes and the URA3 gene (i.e., pop-out). Either one of the two PEP4 genes could be evicted in this recombination event. To identify if, and when, recombination between the two PEP4 genes occurred, strains GS4-2521-3 and GS4-2521-4 were plated onto YPD medium containing 5-FOA in a serial 10-fold dilution manner. Only Ura$^-$ strains will grow in the presence of 5-FOA, and thus growth in such medium indicates the occurrence of the desired recombination event. Strains able to grow on 5-FOA-containing medium were uracil auxotrophs generated by recombination between the two copies of the PEP4 gene. Ura$^-$ colonies appeared on the 5-FOA-containing plate after 1 week of culture at 30° C.: 10 of these colonies were derived from GS4-2521-3, and 14 of these colonies were derived from GS4-2521-4.

3. Characterization of selected transformants

Fourteen of the Ura$^-$ transformant colonies were purified, and genomic DNA was prepared from each. Each DNA was digested with EcoRI and EcoRV, subjected to electrophoresis on a 0.8% agarose gel, blotted to nitrocellulose and hybridized with a radiolabeled 1.2 kb XbaI/EcoRV fragment of the P. pastoris PEP4 gene. DNA from 7 of the 14 isolates analyzed in this way had a hybridization profile consistent with a PEP4 locus consisting of only a defective pep4 gene lacking ~0.5 kb of sequence present in an intact PEP4 gene. Two of these strains are GS4-2521-3/7 and GS4-2521-4/1.

EXAMPLE VIII

Cloning of a Portion of the PRB-1 Gene of P. Pastoris

The proteinase B gene, PRB-1, encodes a vacuolar serine endoprotease in S. cerevisiae [Moehle et al., Mol. Cell Bio. 7: 4390–4399 (1987)]. A portion of the equivalent gene was cloned from P. pastoris using polymerase chain reaction (PCR) gene amplification techniques [see, for example, Gould et al., in Proc. Natl. Acad. Sci. USA 86: 1934–1938 (1989)]. Degenerate oligonucleotides were synthesized for use in priming cDNA synthesis in the PCR amplification of P. pastoris PRB-1 DNA. These oligonucleotides had homology to sequences of the PRB-1 gene that encode regions of the proteinase B protein which are conserved across species (Moehle et al. supra) The oligonucleotides had the following sequences:

Each oligonucleotide also contained one or more restriction endonuclease recognition sites on its 5' end: a SphI site for oligonucleotide 2 and both PstI and EcoRI sites for oligonucleotide 1. These sites, which are incorporated into the fragments amplified during PCR, were included to facilitate subcloning of the amplified DNA fragments into shuttle plasmids.

The PCR reaction medium consisted of 100 ng of P. pastoris (Strain NRRL Y-11430) genomic DNA in 2 μl of T.E. (10 mM Tris.HCl 1 mM EDTA), 10 μl of oligonucleotide 1 and 10 μl of oligonucleotide 2, 16 μl of a 1.25 mM solution of dGTP, dCTP, DATP, and dTTP, 10 μl of 10× buffer (500 mM KCl, 100 mM Tris.HCl, pH 8.3, 15 mM MgCl$_2$), 0.1% gelatin, 70 μl of water and 0.5 μl of 5 units/μl Taq DNA polymerase. The solution was heated at 94° C. for 2 minutes. The PCR cycling reaction consisted of denaturation for 2 minutes at 96° C., annealing for 1 minute at 50° C. and polymerization for 3.5 minutes at 72° C. The cycle was repeated 31 times.

The product of this PCR was subjected to electrophoresis on an agarose gel, and a fragment of the size predicted (~500 bp) for the product of amplification of the PRB-1 gene between positions corresponding to oligonucleotides 1 and 2 was isolated on DE81 paper. This DNA was digested with EcoRI and SphI and the digest was subjected to electrophoresis on an agarose gel. The 500 bp fragment was isolated using DE81 paper and was ligated into 10 ng of pUC19, which had been linearized by cutting with EcoRI and SphI in the polylinker. The ligation mix was used to transform *E. coli* MC1061 cells. Restriction enzyme-digested plasmid DNA from ampicillin-resistant transformants was analyzed for the presence of the correct 500 bp EcoRI-SphI fragment. One colony contained the correct plasmid which was named pPRBPP.

The sequence of the cloned portion of the *P. pastoris* PRB-1 gene contained in pPRBPP was generated using the Sanger dideoxy method (see Sanger et al., supra) and is shown in Sequence ID No. 5. This sequence of the *P. pastoris* PRB-1 gene has approximately 74% homology to the sequence of the *S. cerevisiae* PRB-1 gene.

Example IX

Development of a prb-1 Strain of *P. pastoris*

Plasmid pDR911 was constructed for use in developing prb-1 strains of *P. pastoris*. This vector contains an internal portion of the *P. pastoris* PRB-1 gene, which, when used to transform PRB-1 strains of *P. pastoris*, integrates into the host genome at the PRB-1 locus to generate two incomplete and non-functional copies of the PRB-1 gene. Vector pDR911 also contains a complete functional *P. pastoris* URA3 gene for use as a selectable marker in ura3 host strains of *P. pastoris*.

A. Construction of PDR911

The PRB1 gene fragment of *P. pastoris* in pPRBPP was isolated by restriction digestion of PPRBPP with PstI and SphI. The reaction mixture was loaded onto a 0.8% agarose gel and the 0.5 kb fragment was purified with DE81 paper.

Figure 7:
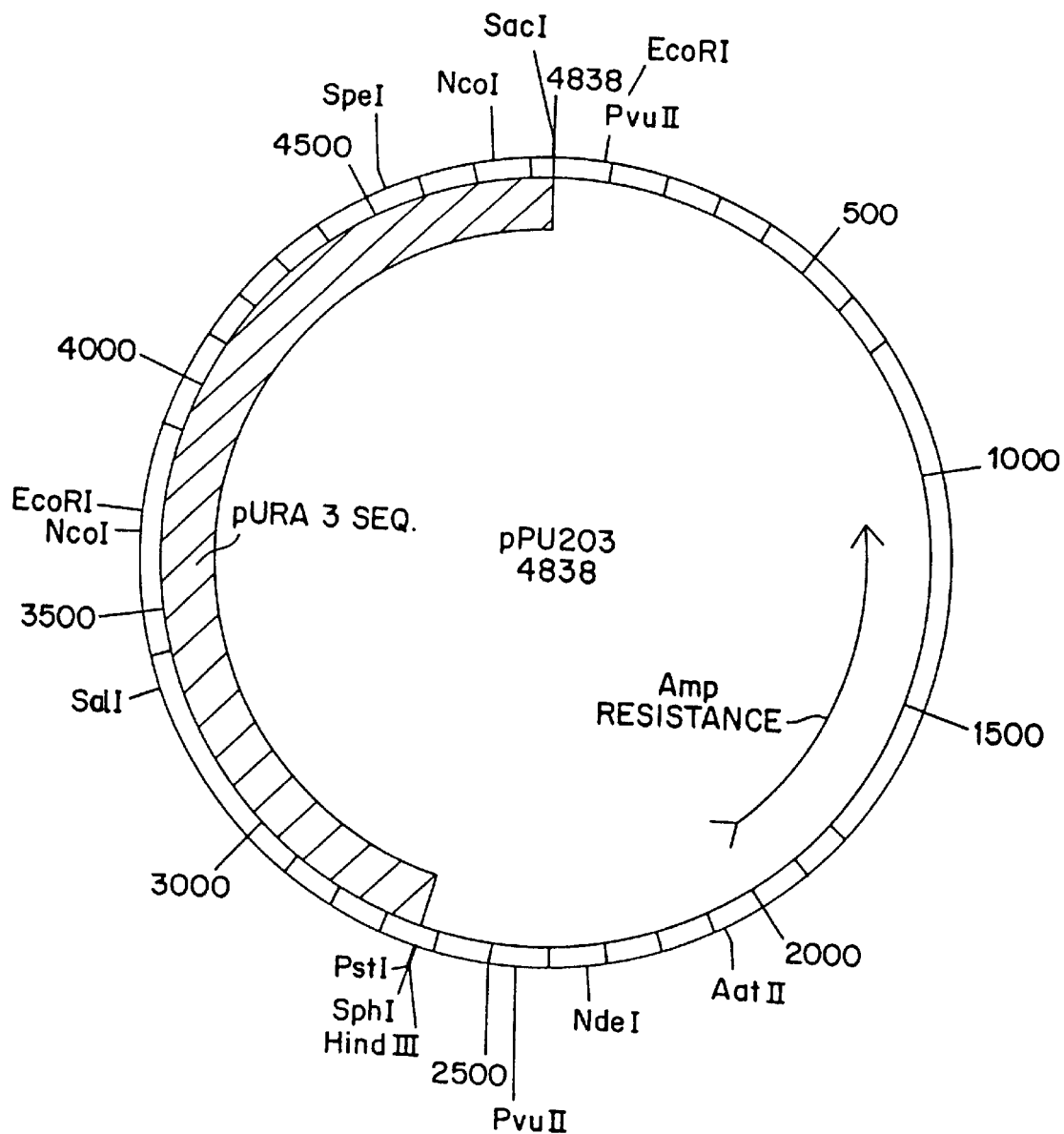
FIG. 7 is a restriction map of plasmid pPU203.

This 0.5 kb fragment was ligated into a linear form of plasmid pPU203, a *P. pastoris* URA3-containing pUC-based plasmid (see FIG. 7). Plasmid pPU203 was linearized by cleavage with SphI and PstI, and ~10 ng was ligated with ~100 ng of the Pichia DNA fragment. The ligation mixture was used to transform *E. coli* strain MC1061 to ampicillin resistance. Ampicillin-resistant colonies were screened by analysis of PstI/SphI-digested colony DNA for the diagnostic fragment. Correct plasmid was named pDR911 (see FIG. 16).

B. Transformation of GS4-2 with pDR911

To generate prb-1 strains of *P. pastoris*, one could transform GS4-2 by standard spheroplast transformation with pDR911 that had been linearized by digestion with BglII. Southern blot hybridization of DNA from Ura$^+$ transformants would enable confirmation of prb-1 strains created by disruption of the PRB-1 locus. Proteinase B activity assays [see, for example, Jones et al., in Genetics 102: 665–677 (1982)] of transformants would further confirm the proteinase B deficiency of the strains.

While the invention has been described in detail with reference to certain preferred embodiments thereof, it will be understood that modifications and variations are within the spirit and scope of that which is described and claimed.

Summary of Sequences

Sequence ID No. 1 is the nucleic acid sequence and deduced amino acid sequence of a *Pichia pastoris* PEP4 gene.

Sequence ID No. 2 is the deduced amino acid sequence for the above gene.

Sequence ID No. 3 is the nucleic acid sequence and deduced amino acid sequence of a *Pichia pastoris* orotodine-5'-phosphate decarboxylase gene.

Sequence ID No. 4 is the deduced amino acid sequence for the above-referenced gene.

Sequence ID No. 5 is a nucleic acid sequence and deduced amino acid sequence of a portion of a *Pichia pastoris* proteinase B gene.

Sequence ID No. 6 is the deduced amino acid sequence for the above partial gene sequence.

That which is claimed is:

1. An isolated DNA fragment obtained from a species of the genus Pichia, comprising a sequence of nucleotides that encodes the orotidine-5'-phosphate decarboxylase gene.

2. The DNA fragment of claim 1, wherein the orotidine-5' phosphate decarboxylase gene encodes the amino acid sequence as set forth in Sequence ID No. 4.

3. The DNA fragment of claim 1, wherein the orotidine-5' phosphate decarboxylase gene, wherein said gene has the nucleic acid sequence as set forth in Sequence ID No. 3.

* * * * *

UNITED STATES PATENT AND TRADEMARK OFFICE
CERTIFICATE OF CORRECTION

PATENT NO. : 5,831,053
DATED : November 3, 1998
INVENTOR(S) : Gleeson, M. et al.

It is certified that error appears in the above-identified patent and that said Letters Patent is hereby corrected as shown below:

At column 1, lines 5-10, replace "This is a divisional of application Ser. No. 08/245,756, filed May 16, 1994 now U. S. Pat. No. 5,541,112, which is a divisional of Ser. No. 08/088,633, filed Jul. 6, 1993, U.S. Pat. No. 5,324,660 which in turn is a continuation of application Ser. No. 07/678,916, filed Apr. 1, 1991, now abandoned." with --This is a divisional of application Ser. No. 08/245,756, filed May 16, 1994, now U.S. Pat. No. 5,541,112, which is a divisional of U. S. application Ser. No. 08/088,633, filed Jul. 6, 1993, now U.S. Pat. No. 5,324,660, which in turn is a continuation of application Ser. No. 07/678,916, filed Apr. 1, 1991, now abandoned.--.

At column 1, line 53, replace "affect" with --effect--.
At column 11, lines 9-10, replace "can be characterized by reference to the restriction map shown in Figure 12" with --has the amino acid sequence set forth in Sequence ID No. 4--.

Signed and Sealed this

Eleventh Day of May, 1999

Attest:

Q. TODD DICKINSON

*Attesting Officer*   Acting Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2032 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 239..1468

( i x ) FEATURE:
        ( A ) NAME/KEY: mat_peptide
        ( B ) LOCATION: 239..1468

( x i ) SEQUENCE DESCRIPTION: SEQ ID NO:1:

| | | | | | | | | | | | | |
|---|---|---|---|---|---|---|---|---|---|---|---|---|
| GAATTCATAA | TGGTGAGATT | AGGTAATCGT | CCGGAATAGG | AATAGTGGTT | TGGGGCGATT | | | | | | | 60 |
| AATCGCACCT | GCCTTATATG | GTAAGTACCT | TGACCGATAA | GGTGGCAACT | ATTTAGAACA | | | | | | | 120 |
| AAGCAAGCCA | CCTTTCTTTA | TCTGTAACTC | TGTCGAAGCA | AGCATCTTTA | CTAGAGAACA | | | | | | | 180 |
| TCTAAACCAT | TTTACATTCT | AGAGTTCCAT | TTCTCAATTA | CTGATAATCA | ATTTAAAG | | | | | | | 238 |

```
ATG  ATA  TTT  GAC  GGT  ACT  ACG  ATG  TCA  ATT  GCC  ATT  GGT  TTG  CTC  TCT        286
Met  Ile  Phe  Asp  Gly  Thr  Thr  Met  Ser  Ile  Ala  Ile  Gly  Leu  Leu  Ser
 1              5                        10                       15

ACT  CTA  GGT  ATT  GGT  GCT  GAA  GCC  AAA  GTT  CAT  TCT  GCT  AAG  ATA  CAC        334
Thr  Leu  Gly  Ile  Gly  Ala  Glu  Ala  Lys  Val  His  Ser  Ala  Lys  Ile  His
                20                       25                       30

AAG  CAT  CCA  GTC  TCA  GAA  ACT  TTA  AAA  GAG  GCC  AAT  TTT  GGG  CAG  TAT        382
Lys  His  Pro  Val  Ser  Glu  Thr  Leu  Lys  Glu  Ala  Asn  Phe  Gly  Gln  Tyr
          35                       40                       45

GTC  TCT  GCT  CTG  GAA  CAT  AAA  TAT  GTT  TCT  CTG  TTC  AAC  GAA  CAA  AAT        430
Val  Ser  Ala  Leu  Glu  His  Lys  Tyr  Val  Ser  Leu  Phe  Asn  Glu  Gln  Asn
     50                       55                       60

GCT  TTG  TCC  AAG  TCG  AAT  TTT  ATG  TCT  CAG  CAA  GAT  GGT  TTT  GCC  GTT        478
Ala  Leu  Ser  Lys  Ser  Asn  Phe  Met  Ser  Gln  Gln  Asp  Gly  Phe  Ala  Val
65                       70                       75                       80

GAA  GCT  TCG  CAT  GAT  GCT  CCA  CTT  ACA  AAC  TAT  CTT  AAC  GCT  CAG  TAT        526
Glu  Ala  Ser  His  Asp  Ala  Pro  Leu  Thr  Asn  Tyr  Leu  Asn  Ala  Gln  Tyr
                85                       90                       95

TTT  ACT  GAG  GTA  TCA  TTA  GGT  ACC  CCT  CCA  CAA  TCG  TTC  AAG  GTG  ATT        574
Phe  Thr  Glu  Val  Ser  Leu  Gly  Thr  Pro  Pro  Gln  Ser  Phe  Lys  Val  Ile
               100                      105                      110

CTT  GAC  ACA  GGA  TCC  TCC  AAT  TTA  TGG  GTT  CCT  AGC  AAA  GAT  TGT  GGA        622
Leu  Asp  Thr  Gly  Ser  Ser  Asn  Leu  Trp  Val  Pro  Ser  Lys  Asp  Cys  Gly
         115                      120                      125

TCA  TTA  GCT  TGC  TTC  TTG  CAT  GCT  AAG  TAT  GAC  CAT  GAT  GAG  TCT  TCT        670
Ser  Leu  Ala  Cys  Phe  Leu  His  Ala  Lys  Tyr  Asp  His  Asp  Glu  Ser  Ser
    130                      135                      140

ACT  TAT  AAG  AAG  AAT  GGT  AGT  AGC  TTT  GAA  ATT  AGG  TAT  GGA  TCC  GGT        718
Thr  Tyr  Lys  Lys  Asn  Gly  Ser  Ser  Phe  Glu  Ile  Arg  Tyr  Gly  Ser  Gly
145                      150                      155                      160

TCC  ATG  GAA  GGG  TAT  GTT  TCT  CAG  GAT  GTG  TTG  CAA  ATT  GGG  GAT  TTG        766
Ser  Met  Glu  Gly  Tyr  Val  Ser  Gln  Asp  Val  Leu  Gln  Ile  Gly  Asp  Leu
               165                      170                      175

ACC  ATT  CCC  AAA  GTT  GAT  TTT  GCT  GAG  GCC  ACA  TCG  GAG  CCG  GGG  TTG        814
Thr  Ile  Pro  Lys  Val  Asp  Phe  Ala  Glu  Ala  Thr  Ser  Glu  Pro  Gly  Leu
         180                      185                      190

GCC  TTC  GCT  TTT  GGC  AAA  TTT  GAC  GGA  ATT  TTG  GGG  CTT  GCT  TAT  GAT        862
Ala  Phe  Ala  Phe  Gly  Lys  Phe  Asp  Gly  Ile  Leu  Gly  Leu  Ala  Tyr  Asp
              195                      200                      205

TCA  ATA  TCA  GTA  AAT  AAG  ATT  GTT  CCT  CCA  ATT  TAC  AAG  GCT  TTG  GAA        910
Ser  Ile  Ser  Val  Asn  Lys  Ile  Val  Pro  Pro  Ile  Tyr  Lys  Ala  Leu  Glu
    210                      215                      220

TTA  GAT  CTC  CTT  GAC  GAA  CCA  AAA  TTT  GCC  TTC  TAC  TTG  GGG  GAT  ACG        958
Leu  Asp  Leu  Leu  Asp  Glu  Pro  Lys  Phe  Ala  Phe  Tyr  Leu  Gly  Asp  Thr
225                      230                      235                      240

GAC  AAA  GAT  GAA  TCC  GAT  GGC  GGT  TTG  GCC  ACA  TTT  GGT  GGT  GTG  GAC       1006
Asp  Lys  Asp  Glu  Ser  Asp  Gly  Gly  Leu  Ala  Thr  Phe  Gly  Gly  Val  Asp
               245                      250                      255

AAA  TCT  AAG  TAT  GAA  GGA  AAG  ATC  ACC  TGG  TTG  CCT  GTC  AGA  AGA  AAG       1054
Lys  Ser  Lys  Tyr  Glu  Gly  Lys  Ile  Thr  Trp  Leu  Pro  Val  Arg  Arg  Lys
         260                      265                      270

GCT  TAC  TGG  GAG  GTC  TCT  TTT  GAT  GGT  GTA  GGT  TTG  GGA  TCC  GAA  TAT       1102
```

| | | | | | | | | | | | | | | | | |
|---|---|---|---|---|---|---|---|---|---|---|---|---|---|---|---|---|
| Ala | Tyr | Trp | Glu | Val | Ser | Phe | Asp | Gly | Val | Gly | Leu | Gly | Ser | Glu | Tyr | |
| | | 275 | | | | | 280 | | | | | 285 | | | | |
| GCT | GAA | TTG | CAA | AAA | ACT | GGT | GCA | GCC | ATC | GAC | ACT | GGA | ACC | TCA | TTG | 1150 |
| Ala | Glu | Leu | Gln | Lys | Thr | Gly | Ala | Ala | Ile | Asp | Thr | Gly | Thr | Ser | Leu | |
| | | 290 | | | | | 295 | | | | | 300 | | | | |
| ATT | GCT | TTG | CCC | AGT | GGC | CTA | GCT | GAA | ATT | CTC | AAT | GCA | GAA | ATT | GGT | 1198 |
| Ile | Ala | Leu | Pro | Ser | Gly | Leu | Ala | Glu | Ile | Leu | Asn | Ala | Glu | Ile | Gly | |
| 305 | | | | | 310 | | | | | 315 | | | | | 320 | |
| GCT | ACC | AAG | GGT | TGG | TCT | GGT | CAA | TAC | GCT | GTG | GAC | TGT | GAC | ACT | AGA | 1246 |
| Ala | Thr | Lys | Gly | Trp | Ser | Gly | Gln | Tyr | Ala | Val | Asp | Cys | Asp | Thr | Arg | |
| | | | | 325 | | | | | 330 | | | | | 335 | | |
| GAC | TCT | TTG | CCA | GAC | TTA | ACT | TTA | ACC | TTC | GCC | GGT | TAC | AAC | TTT | ACC | 1294 |
| Asp | Ser | Leu | Pro | Asp | Leu | Thr | Leu | Thr | Phe | Ala | Gly | Tyr | Asn | Phe | Thr | |
| | | | 340 | | | | | 345 | | | | | 350 | | | |
| ATT | ACT | CCA | TAT | GAC | TAT | ACT | TTG | GAG | GTT | TCT | GGG | TCA | TGT | ATT | AGT | 1342 |
| Ile | Thr | Pro | Tyr | Asp | Tyr | Thr | Leu | Glu | Val | Ser | Gly | Ser | Cys | Ile | Ser | |
| | | 355 | | | | | 360 | | | | | 365 | | | | |
| GCT | TTC | ACC | CCC | ATG | GAC | TTT | CCT | GAA | CCA | ATA | GGT | CCT | TTG | GCA | ATC | 1390 |
| Ala | Phe | Thr | Pro | Met | Asp | Phe | Pro | Glu | Pro | Ile | Gly | Pro | Leu | Ala | Ile | |
| | | 370 | | | | | 375 | | | | | 380 | | | | |
| ATT | GGT | GAC | TCG | TTC | TTG | AGA | AAA | TAT | TAC | TCA | GTT | TAT | GAC | CTA | GGC | 1438 |
| Ile | Gly | Asp | Ser | Phe | Leu | Arg | Lys | Tyr | Tyr | Ser | Val | Tyr | Asp | Leu | Gly | |
| 385 | | | | | 390 | | | | | 395 | | | | | 400 | |
| AAA | GAT | GCA | GTA | GGT | TTA | GCC | AAG | TCT | ATT | TAGGCAAGAA | | TAAAAGTTGC | | | | 1488 |
| Lys | Asp | Ala | Val | Gly | Leu | Ala | Lys | Ser | Ile | | | | | | | |
| | | | | 405 | | | | | 410 | | | | | | | |

```
TCAGCTGAAC TTATTTGGTT ACTTATCAGG TAGTGAAGAT GTAGAGAATA TATGTTTAGG    1548

TATTTTTTTT TAGTTTTTCT CCTATAACTC ATCTTCAGTA CGTGATTGCT TGTCAGCTAC    1608

CTTGACAGGG GCGCATAAGT GATATCGTGT ACTGCTCAAT CAAGATTTGC CTGCTCCATT    1668

GATAAGGGTA TAAGAGACCC ACCTGCTCCT CTTTAAAATT CTCTCTTAAC TGTTGTGAAA    1728

ATCATCTTCG AAGCAAATTC GAGTTTAAAT CTATGCGGTT GGTAACTAAA GGTATGTCAT    1788

GGTGGTATAT AGTTTTTCAT TTTACCTTTT ACTAATCAGT TTTACAGAAG AGGAACGTCT    1848

TTCTCAAGAT CGAAATAGGA CTAAATACTG GAGACGATGG GGTCCTTATT TGGGTGAAAG    1908

GCAGTGGGCT ACAGTAAGGG AAGACTATTC CGATGATGGA GATGCTTGGT CTGCTTTTCC    1968

TTTTGAGCAA TCTCATTTGA GAACTTATCG CTGGGGAGAG GATGGACTAG CTGGAGTCTC    2028

AGAC                                                                 2032
```

( 2 ) INFORMATION FOR SEQ ID NO:2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ile | Phe | Asp | Gly | Thr | Thr | Met | Ser | Ile | Ala | Ile | Gly | Leu | Leu | Ser |
| 1 | | | | 5 | | | | 10 | | | | | | 15 | |
| Thr | Leu | Gly | Ile | Gly | Ala | Glu | Ala | Lys | Val | His | Ser | Ala | Lys | Ile | His |
| | | | 20 | | | | 25 | | | | | 30 | | | |
| Lys | His | Pro | Val | Ser | Glu | Thr | Leu | Lys | Glu | Ala | Asn | Phe | Gly | Gln | Tyr |
| | | 35 | | | | | 40 | | | | | 45 | | | |
| Val | Ser | Ala | Leu | Glu | His | Lys | Tyr | Val | Ser | Leu | Phe | Asn | Glu | Gln | Asn |
| | 50 | | | | | 55 | | | | | 60 | | | | |
| Ala | Leu | Ser | Lys | Ser | Asn | Phe | Met | Ser | Gln | Gln | Asp | Gly | Phe | Ala | Val |

```
              65                      70                      75                      80
Glu  Ala  Ser  His  Asp  Ala  Pro  Leu  Thr  Asn  Tyr  Leu  Asn  Ala  Gln  Tyr
                    85                      90                      95

Phe  Thr  Glu  Val  Ser  Leu  Gly  Thr  Pro  Pro  Gln  Ser  Phe  Lys  Val  Ile
               100                     105                     110

Leu  Asp  Thr  Gly  Ser  Ser  Asn  Leu  Trp  Val  Pro  Ser  Lys  Asp  Cys  Gly
               115                     120                     125

Ser  Leu  Ala  Cys  Phe  Leu  His  Ala  Lys  Tyr  Asp  His  Asp  Glu  Ser  Ser
          130                     135                     140

Thr  Tyr  Lys  Lys  Asn  Gly  Ser  Ser  Phe  Glu  Ile  Arg  Tyr  Gly  Ser  Gly
145                     150                     155                     160

Ser  Met  Glu  Gly  Tyr  Val  Ser  Gln  Asp  Val  Leu  Gln  Ile  Gly  Asp  Leu
               165                     170                     175

Thr  Ile  Pro  Lys  Val  Asp  Phe  Ala  Glu  Ala  Thr  Ser  Glu  Pro  Gly  Leu
               180                     185                     190

Ala  Phe  Ala  Phe  Gly  Lys  Phe  Asp  Gly  Ile  Leu  Gly  Leu  Ala  Tyr  Asp
          195                     200                     205

Ser  Ile  Ser  Val  Asn  Lys  Ile  Val  Pro  Pro  Ile  Tyr  Lys  Ala  Leu  Glu
     210                     215                     220

Leu  Asp  Leu  Leu  Asp  Glu  Pro  Lys  Phe  Ala  Phe  Tyr  Leu  Gly  Asp  Thr
225                     230                     235                     240

Asp  Lys  Asp  Glu  Ser  Asp  Gly  Gly  Leu  Ala  Thr  Phe  Gly  Gly  Val  Asp
               245                     250                     255

Lys  Ser  Lys  Tyr  Glu  Gly  Lys  Ile  Thr  Trp  Leu  Pro  Val  Arg  Arg  Lys
               260                     265                     270

Ala  Tyr  Trp  Glu  Val  Ser  Phe  Asp  Gly  Val  Gly  Leu  Gly  Ser  Glu  Tyr
          275                     280                     285

Ala  Glu  Leu  Gln  Lys  Thr  Gly  Ala  Ala  Ile  Asp  Thr  Gly  Thr  Ser  Leu
     290                     295                     300

Ile  Ala  Leu  Pro  Ser  Gly  Leu  Ala  Glu  Ile  Leu  Asn  Ala  Glu  Ile  Gly
305                     310                     315                     320

Ala  Thr  Lys  Gly  Trp  Ser  Gly  Gln  Tyr  Ala  Val  Asp  Cys  Asp  Thr  Arg
               325                     330                     335

Asp  Ser  Leu  Pro  Asp  Leu  Thr  Leu  Thr  Phe  Ala  Gly  Tyr  Asn  Phe  Thr
               340                     345                     350

Ile  Thr  Pro  Tyr  Asp  Tyr  Thr  Leu  Glu  Val  Ser  Gly  Ser  Cys  Ile  Ser
          355                     360                     365

Ala  Phe  Thr  Pro  Met  Asp  Phe  Pro  Glu  Pro  Ile  Gly  Pro  Leu  Ala  Ile
     370                     375                     380

Ile  Gly  Asp  Ser  Phe  Leu  Arg  Lys  Tyr  Tyr  Ser  Val  Tyr  Asp  Leu  Gly
385                     390                     395                     400

Lys  Asp  Ala  Val  Gly  Leu  Ala  Lys  Ser  Ile
               405                     410
```

( 2 ) INFORMATION FOR SEQ ID NO:3:

( i ) SEQUENCE CHARACTERISTICS:
        ( A ) LENGTH: 2688 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 643..1431

( i x ) FEATURE:
    ( A ) NAME/KEY: mat_peptide
    ( B ) LOCATION: 643..1431

( x i ) SEQUENCE DESCRIPTION: SEQ ID NO:3:

```
CTGCAGAAAT  GGGGAGATAA  CCACCTTTGA  CGAATTGACT  AAAGTTCTAC  AGATCATGTT        60

TACAAATGCC  ATCATCTATA  ACGATGAAGA  CAGTGATGTT  TCGAAGCTAA  CGATTGAAAT       120

GATGGAAGAA  ACTACTAAGA  TTATAGAGCT  GTTCAGAGAA  AGTCTGGATT  AGTCCTGGAC       180

AATGAACTTT  ATGTACAAAA  ATATGGGGTT  AACGTCTTAG  CTGTTGCATC  ATAAGTTGGT       240

TTTGTTCTTG  GAAACGTTGA  CCAACTCTCT  CACTGTGCTT  GAGGAACTTT  TCTGCACACT       300

TGTTGATGCA  GCCTTCCTCC  TTAGAAGTCA  ACTTGTTAGA  TGTAAAATCA  TTGACACAGT       360

CTGTAAAACA  TTTGCTAACC  AAATCGGAGT  AAAGACGCAT  GAAGTCTTTC  ATTTGTTTTT       420

GTTCAACGAG  TTTCTGGAAC  TCTTGTTGTT  CTTTAGCGTT  CAATGCGTCC  ATTTTGTGAT       480

GTACTTGGTT  GGGGTAGAGT  TAGCACTTGC  TCTCTCTGTT  ACCAGTTTTT  GTCAAGATTG       540

AAGAAAAAAG  TTTTTGGAC   GGTACACGTC  GCACCTATCC  TTCGCATTGA  TCCACTCTAA       600

TGAGTTAACA  TCAACCTGAT  CAAAGGGATA  GATACCTAGA  CA ATG GCT CGC AGT           654
                                                  Met Ala Arg Ser
                                                   1
```

```
TAT GCC GAG AGA GCA AAT ACT CAT CAA TCA CCT GTG GCA CGA CGA CTG              702
Tyr Ala Glu Arg Ala Asn Thr His Gln Ser Pro Val Ala Arg Arg Leu
 5           10                  15                  20

TTT GCG CTT ATG GAA CAG AAA CAG AGT AAC CTA TGC GCA TCA GTC GAC              750
Phe Ala Leu Met Glu Gln Lys Gln Ser Asn Leu Cys Ala Ser Val Asp
             25                  30                  35

GTG AGA ACA ACT AAA GAA TTA TTG GAG CTT CTA GAT AAA TTG GGC CCA              798
Val Arg Thr Thr Lys Glu Leu Leu Glu Leu Leu Asp Lys Leu Gly Pro
         40                  45                  50

TTT ATC TGT TTG GCC AAG ACT CAT ATC GAC ATA ATT GAT GAC TTC ACG              846
Phe Ile Cys Leu Ala Lys Thr His Ile Asp Ile Ile Asp Asp Phe Thr
     55                  60                  65

TAT GAT GGA ACT ATT CTG CCT TTA TTG GAA CTA TCA AAG AAA CAC AAG              894
Tyr Asp Gly Thr Ile Leu Pro Leu Leu Glu Leu Ser Lys Lys His Lys
 70                  75                  80

TTT TTA ATT TTT GAG GAC AGA AAG TTT GCT GAT ATA GGC AAC ACT GTC              942
Phe Leu Ile Phe Glu Asp Arg Lys Phe Ala Asp Ile Gly Asn Thr Val
 85                  90                  95                 100

AAG CAT CAA TAT CAA GGA GGT GTC TAC AAG ATT GCA CAA TGG GCA GAT              990
Lys His Gln Tyr Gln Gly Gly Val Tyr Lys Ile Ala Gln Trp Ala Asp
                105                 110                 115

ATT ACA AAT GCT CAT GGT GTC ATT GGT AGT GGA ATT GTA AAG GGT CTA             1038
Ile Thr Asn Ala His Gly Val Ile Gly Ser Gly Ile Val Lys Gly Leu
            120                 125                 130

AAG GAG GCA GCC ACT GAG ACA ACA GAT CAA CCA AGG GGA CTA TTG ATG             1086
Lys Glu Ala Ala Thr Glu Thr Thr Asp Gln Pro Arg Gly Leu Leu Met
        135                 140                 145

TTG GCT GAA CTG TCG TCA AAG GGA TCA ATT GCC CAT GGT AAG TAC ACC             1134
Leu Ala Glu Leu Ser Ser Lys Gly Ser Ile Ala His Gly Lys Tyr Thr
    150                 155                 160

GAA GAA ACT GTA GAA ATT GCA AAA TCA GAC AAG GAA TTC GTC ATT GGG             1182
Glu Glu Thr Val Glu Ile Ala Lys Ser Asp Lys Glu Phe Val Ile Gly
165                 170                 175                 180

TTT ATT GCT CAA AAT TCT ATG GGA GGA CAA GAT GAA GGG TTC GAT TGG             1230
Phe Ile Ala Gln Asn Ser Met Gly Gly Gln Asp Glu Gly Phe Asp Trp
                185                 190                 195

ATT ATT ATG ACA CCA GGT GTT GGT TTG GAT GAC ACT GGT GAT GCT CTA             1278
Ile Ile Met Thr Pro Gly Val Gly Leu Asp Asp Thr Gly Asp Ala Leu
```

-continued

|  |  |  | 200 |  |  |  |  | 205 |  |  |  |  | 210 |  |  |  |
|---|---|---|---|---|---|---|---|---|---|---|---|---|---|---|---|---|
| GGC | CAA | CAA | TAT | CGA | ACA | GTG | AGT | CAA | GTA | TTT | TCC | ACT | GGC | ACT | GAC | 1326 |
| Gly | Gln | Gln | Tyr | Arg | Thr | Val | Ser | Gln | Val | Phe | Ser | Thr | Gly | Thr | Asp |  |
|  |  | 215 |  |  |  |  | 220 |  |  |  |  | 225 |  |  |  |  |
| ATC | ATA | ATC | GTA | GGT | CGT | GGT | TTG | TTT | GGC | AAG | GGC | AGA | GAT | CCC | TTA | 1374 |
| Ile | Ile | Ile | Val | Gly | Arg | Gly | Leu | Phe | Gly | Lys | Gly | Arg | Asp | Pro | Leu |  |
|  |  | 230 |  |  |  |  | 235 |  |  |  |  | 240 |  |  |  |  |
| AAA | GAA | GGT | GAA | CGG | TAT | AGA | AAA | GCT | GGG | TGG | GAA | GCT | TAC | CAA | AAT | 1422 |
| Lys | Glu | Gly | Glu | Arg | Tyr | Arg | Lys | Ala | Gly | Trp | Glu | Ala | Tyr | Gln | Asn |  |
| 245 |  |  |  |  | 250 |  |  |  |  | 255 |  |  |  |  | 260 |  |
| ATT | CTG | AGG | TAAATTACAA | GTATGTACAG | GGGATCAATT | GTTTCGGGCG |  |  |  |  |  |  |  |  |  | 1471 |
| Ile | Leu | Arg |  |  |  |  |  |  |  |  |  |  |  |  |  |  |

```
ATTCAACTGA ATCGATCTTC AATTTCATCG CTCAATTTTT GACGCAGTAT TTCAAACACC    1531
AGAAGCCCCA CGGATGTTGC TGGAATGGTA GTTAACGCAT TCCTAACGAA CCCTTTATAA    1591
AACCAGCGGG TCCAAGATAG TTTAGACTTC TCATGTAAGC TCACCAACTG GTGGAATGTA    1651
TCTAAGTATG ATCGGTAATA TAGACGGAAT TTACTTTTCT TATCCCAGGA GTTCTCGTTG    1711
AAAATATCCA ACGCTTCCAA CCTTGCTAAA TGTATTGACT GAACTTTAGA AAATGGGTAT    1771
TGAACGGCTA GTAACGAACA TGCAGCGCTA GCACCAGCCA AAAGAATAAA AGTCGTCCTC    1831
AGGATATTTT CACTTTTCGT TTTCACTGTG TCACCTTGGG GCCTTCCAAG AAGACTATTT    1891
TTCATCCTAT CAATTCTCTC CATAGTGTTC TCGGTTATCC TGTAACCTCT ATTCTTAATG    1951
GCTTCGAATG TTGTGAAATA TATAGCAAAG GATGTGCTTT CTTTGACCAG ACTCAAGGAG    2011
TAGCCAGCAA ATACCCCAG AAAACCACTA GTTTTTAGTT TATGAAGACC GTAAATCCAT    2071
AAGTTGTCAT TCTTGCCCCC AATAATCTCG GAGGCATTAG ATCGGGCATA TATTGCATCA    2131
ATTGGGGCAG CTACCAATGA CTGCGCAGCT CCAGCTAGAA ACCCAGCTCG AAATACATCC    2191
ACTAGTCTTG GATTTGCTAT CGATCTGCCC TCTTGACCGT CAGTATATGA CTGCAAACAT    2251
GATAAATACG TTGTGTAAAG TACAATTCCC ATCACAGAAT TGGCTACCAA TGGTGGCAGG    2311
ACCTTGTTTG GTATCAACTC CCAACCATGG GTTTTGACGG CTCGTAACAA TAGAGCTGGA    2371
TTTGAGTGGA AAATGGGCTG TAAGGTTTAC CTTTCAAATG AGCTCCAAAG AAGATGCGTA    2431
TTGGTGCCAT GTAGTCAAAA CGAGTGGGAC GAAACAGTTT GGCTGGTGTC CTCAGGTACA    2491
GTGAACTAAA TTGGACTAGA ACAGCTCTGA TCCCAGCTGT CGAAGCAGAC ACCACTTGAG    2551
TGTTTTTGTT GCTAAGAGTA GCCTTTTTAG AATCATCGTT GTCTTCCATA GGTTTCTGGA    2611
ACACAATGCC AGAGTTCATA GAGGATCAGA GGGGAATTGA GGTGTGTGTA TATGTATTTA    2671
TAGGGGTACC GAGCTCG                                                   2688
```

(2) INFORMATION FOR SEQ ID NO:4:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO:4:

| Met | Ala | Arg | Ser | Tyr | Ala | Glu | Arg | Ala | Asn | Thr | His | Gln | Ser | Pro | Val |
|---|---|---|---|---|---|---|---|---|---|---|---|---|---|---|---|
| 1 |  |  |  | 5 |  |  |  |  | 10 |  |  |  |  | 15 |  |

| Ala | Arg | Arg | Leu | Phe | Ala | Leu | Met | Glu | Gln | Lys | Gln | Ser | Asn | Leu | Cys |
|---|---|---|---|---|---|---|---|---|---|---|---|---|---|---|---|
|  |  |  | 20 |  |  |  |  | 25 |  |  |  |  | 30 |  |  |

| Ala | Ser | Val | Asp | Val | Arg | Thr | Thr | Lys | Glu | Leu | Leu | Glu | Leu | Leu | Asp |
|---|---|---|---|---|---|---|---|---|---|---|---|---|---|---|---|
|  |  | 35 |  |  |  |  | 40 |  |  |  |  | 45 |  |  |  |

```
Lys Leu Gly Pro Phe Ile Cys Leu Ala Lys Thr His Ile Asp Ile Ile
         50                  55                  60
Asp Asp Phe Thr Tyr Asp Gly Thr Ile Leu Pro Leu Leu Glu Leu Ser
 65                  70                  75                  80
Lys Lys His Lys Phe Leu Ile Phe Glu Asp Arg Lys Phe Ala Asp Ile
                 85                  90                  95
Gly Asn Thr Val Lys His Gln Tyr Gln Gly Gly Val Tyr Lys Ile Ala
                100                 105                 110
Gln Trp Ala Asp Ile Thr Asn Ala His Gly Val Ile Gly Ser Gly Ile
             115                 120                 125
Val Lys Gly Leu Lys Glu Ala Ala Thr Glu Thr Thr Asp Gln Pro Arg
    130                 135                 140
Gly Leu Leu Met Leu Ala Glu Leu Ser Ser Lys Gly Ser Ile Ala His
145                 150                 155                 160
Gly Lys Tyr Thr Glu Glu Thr Val Glu Ile Ala Lys Ser Asp Lys Glu
                165                 170                 175
Phe Val Ile Gly Phe Ile Ala Gln Asn Ser Met Gly Gly Gln Asp Glu
                180                 185                 190
Gly Phe Asp Trp Ile Ile Met Thr Pro Gly Val Gly Leu Asp Asp Thr
             195                 200                 205
Gly Asp Ala Leu Gly Gln Gln Tyr Arg Thr Val Ser Gln Val Phe Ser
    210                 215                 220
Thr Gly Thr Asp Ile Ile Ile Val Gly Arg Gly Leu Phe Gly Lys Gly
225                 230                 235                 240
Arg Asp Pro Leu Lys Glu Gly Glu Arg Tyr Arg Lys Ala Gly Trp Glu
                245                 250                 255
Ala Tyr Gln Asn Ile Leu Arg
                260
```

( 2 ) INFORMATION FOR SEQ ID NO:5:

( i ) SEQUENCE CHARACTERISTICS:
        ( A ) LENGTH: 555 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 3..554

( i x ) FEATURE:
        ( A ) NAME/KEY: mat_peptide
        ( B ) LOCATION: 3..554

( x i ) SEQUENCE DESCRIPTION: SEQ ID NO:5:

```
GA ATT CTG CAG GGA AAC GGC CAC GGT ACA CAT TGT GCT GGT ACC ATT    47
   Ile Leu Gln Gly Asn Gly His Gly Thr His Cys Ala Gly Thr Ile
    1               5                  10                  15

GCT TCT GAA AGC TAC GGT GTT GCC AAG AAG GCT AAT GTT GTT GCC ATC    95
Ala Ser Glu Ser Tyr Gly Val Ala Lys Lys Ala Asn Val Val Ala Ile
                 20                  25                  30

AAG GTC TTG AGA TCT AAT GGT TCT GGT TCG ATG TCA GAT GTT CTG AAG   143
Lys Val Leu Arg Ser Asn Gly Ser Gly Ser Met Ser Asp Val Leu Lys
             35                  40                  45

GGT GTT GAG TAT GCC ACC CAA TCC CAC TTG GAT GCT GTT AAA AAG GGC   191
Gly Val Glu Tyr Ala Thr Gln Ser His Leu Asp Ala Val Lys Lys Gly
        50                  55                  60

AAC AAG AAA TTT AAG GGC TCT ACC GCT AAC ATG TCA CTG GGT GGT GGT   239
```

|   |   |   |   |   |   |   |   |   |   |   |   |   |   |   |
|---|---|---|---|---|---|---|---|---|---|---|---|---|---|---|
| Asn | Lys | Lys | Phe | Lys | Gly | Ser | Thr | Ala | Asn | Met | Ser | Leu | Gly | Gly | Gly |
|  | 65 |  |  |  |  | 70 |  |  |  | 75 |  |  |  |  |

| AAA | TCT | CCT | GCT | TTG | GAC | CTT | GCA | GTC | AAT | GCT | GCT | GTT | AAG | AAT | GGT | 287 |
|-----|-----|-----|-----|-----|-----|-----|-----|-----|-----|-----|-----|-----|-----|-----|-----|-----|
| Lys | Ser | Pro | Ala | Leu | Asp | Leu | Ala | Val | Asn | Ala | Ala | Val | Lys | Asn | Gly |  |
| 80  |     |     |     |     | 85  |     |     |     |     | 90  |     |     |     |     | 95  |  |

| ATT | CAC | TTT | GCC | GTT | GCA | GCA | GGT | AAC | GAA | AAC | CAA | GAT | GCT | TGT | AAC | 335 |
| Ile | His | Phe | Ala | Val | Ala | Ala | Gly | Asn | Glu | Asn | Gln | Asp | Ala | Cys | Asn |  |
|     |     |     |     | 100 |     |     |     |     | 105 |     |     |     |     | 110 |     |  |

| ACC | TCG | CCA | GCA | GCT | GCT | GAG | AAT | GCC | ATC | ACC | GTC | GGT | GCA | TCA | ACC | 383 |
| Thr | Ser | Pro | Ala | Ala | Ala | Glu | Asn | Ala | Ile | Thr | Val | Gly | Ala | Ser | Thr |  |
|     |     |     | 115 |     |     |     |     | 120 |     |     |     |     | 125 |     |     |  |

| TTA | TCA | GAC | GCT | AGA | GCT | TAC | TTT | TCT | AAC | TAC | GGT | AAA | TGT | GTT | GAC | 431 |
| Leu | Ser | Asp | Ala | Arg | Ala | Tyr | Phe | Ser | Asn | Tyr | Gly | Lys | Cys | Val | Asp |  |
|     |     | 130 |     |     |     |     | 135 |     |     |     |     | 140 |     |     |     |  |

| ATT | TTC | GCT | CCA | GGT | TTA | AAC | ATT | CTT | TCT | ACC | TAC | ACT | GGT | TCG | GAT | 479 |
| Ile | Phe | Ala | Pro | Gly | Leu | Asn | Ile | Leu | Ser | Thr | Tyr | Thr | Gly | Ser | Asp |  |
|     | 145 |     |     |     |     | 150 |     |     |     |     | 155 |     |     |     |     |  |

| GAC | GCA | ACT | GCT | ACC | TTG | TCT | GGT | ACT | TCA | ATG | GCC | AGC | CCT | CAT | GTT | 527 |
| Asp | Ala | Thr | Ala | Thr | Leu | Ser | Gly | Thr | Ser | Met | Ala | Ser | Pro | His | Val |  |
| 160 |     |     |     |     | 165 |     |     |     |     | 170 |     |     |     |     | 175 |  |

| GCA | GGC | TTG | CAT | GCA | AGC | TTG | GCA | CTG | G |  |  |  |  |  |  | 555 |
| Ala | Gly | Leu | His | Ala | Ser | Leu | Ala | Leu |   |  |  |  |  |  |  |  |
|     |     |     |     | 180 |     |     |     |     |   |  |  |  |  |  |  |  |

( 2 ) INFORMATION FOR SEQ ID NO:6:

( i ) SEQUENCE CHARACTERISTICS:
        ( A ) LENGTH: 184 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Ile | Leu | Gln | Gly | Asn | Gly | His | Gly | Thr | His | Cys | Ala | Gly | Thr | Ile | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Glu | Ser | Tyr | Gly | Val | Ala | Lys | Lys | Ala | Asn | Val | Val | Ala | Ile | Lys |
|     |     |     | 20  |     |     |     |     | 25  |     |     |     |     | 30  |     |     |

| Val | Leu | Arg | Ser | Asn | Gly | Ser | Gly | Ser | Met | Ser | Asp | Val | Leu | Lys | Gly |
|     |     | 35  |     |     |     |     | 40  |     |     |     |     | 45  |     |     |     |

| Val | Glu | Tyr | Ala | Thr | Gln | Ser | His | Leu | Asp | Ala | Val | Lys | Lys | Gly | Asn |
|     | 50  |     |     |     |     | 55  |     |     |     |     | 60  |     |     |     |     |

| Lys | Lys | Phe | Lys | Gly | Ser | Thr | Ala | Asn | Met | Ser | Leu | Gly | Gly | Gly | Lys |
| 65  |     |     |     |     | 70  |     |     |     |     | 75  |     |     |     |     | 80  |

| Ser | Pro | Ala | Leu | Asp | Leu | Ala | Val | Asn | Ala | Ala | Val | Lys | Asn | Gly | Ile |
|     |     |     |     | 85  |     |     |     |     | 90  |     |     |     |     | 95  |     |

| His | Phe | Ala | Val | Ala | Ala | Gly | Asn | Glu | Asn | Gln | Asp | Ala | Cys | Asn | Thr |
|     |     |     | 100 |     |     |     |     | 105 |     |     |     |     | 110 |     |     |

| Ser | Pro | Ala | Ala | Ala | Glu | Asn | Ala | Ile | Thr | Val | Gly | Ala | Ser | Thr | Leu |
|     |     | 115 |     |     |     |     | 120 |     |     |     |     | 125 |     |     |     |

| Ser | Asp | Ala | Arg | Ala | Tyr | Phe | Ser | Asn | Tyr | Gly | Lys | Cys | Val | Asp | Ile |
|     | 130 |     |     |     |     | 135 |     |     |     |     | 140 |     |     |     |     |

| Phe | Ala | Pro | Gly | Leu | Asn | Ile | Leu | Ser | Thr | Tyr | Thr | Gly | Ser | Asp | Asp |
| 145 |     |     |     |     | 150 |     |     |     |     | 155 |     |     |     |     | 160 |

| Ala | Thr | Ala | Thr | Leu | Ser | Gly | Thr | Ser | Met | Ala | Ser | Pro | His | Val | Ala |
|     |     |     |     | 165 |     |     |     |     | 170 |     |     |     |     | 175 |     |

| Gly | Leu | His | Ala | Ser | Leu | Ala | Leu |
|     |     |     | 180 |     |     |     |     |